US011224635B2

(12) United States Patent
Gardner et al.

(10) Patent No.: US 11,224,635 B2
(45) Date of Patent: Jan. 18, 2022

(54) THERAPEUTIC ANGIOGENESIS FOR TREATMENT OF THE SPINE AND OTHER TISSUES

(71) Applicant: Venturis Therapeutics, Inc., Dallas, TX (US)

(72) Inventors: Vance Gardner, Irvine, CA (US); Hon Yu, Irvine, CA (US); Kenneth A. Thomas, Chatham, NJ (US); Thomas J. Stegmann, Petersberg (DE); John W. Jacobs, Berkeley, CA (US); Tugan Muftuler, Aliso Viejo, CA (US); Shadfar Bahri, Irvine, CA (US); Edwin Anderson, Westminster, CO (US)

(73) Assignees: Venturis Thereuptics, Inc., Dallas, TX (US); Vance Gardner, Irvine, CA (US); Kenneth A. Thomas, Chatham, NJ (US); Thomas J. Stegmann, Petersberg (DE); John W. Jacobs, Berkley, CA (US); Shadfar Bahri, Irvine, CA (US); Edwin Anderson, Westminster, CO (US)

( * ) Notice: Subject to any disclaimer, the term of this patent is extended or adjusted under 35 U.S.C. 154(b) by 758 days.

(21) Appl. No.: 13/831,954

(22) Filed: Mar. 15, 2013

(65) Prior Publication Data

US 2013/0230454 A1    Sep. 5, 2013

Related U.S. Application Data

(63) Continuation-in-part of application No. 12/076,846, filed on Mar. 24, 2008, now Pat. No. 8,983,570.

(60) Provisional application No. 61/022,266, filed on Jan. 18, 2008, provisional application No. 60/920,254, filed on Mar. 27, 2007.

(51) Int. Cl.
| | |
|---|---|
| *A61K 38/18* | (2006.01) |
| *A61K 49/06* | (2006.01) |
| *A61K 49/04* | (2006.01) |
| *A61K 51/00* | (2006.01) |
| *A61K 49/22* | (2006.01) |

(52) U.S. Cl.
CPC .......... *A61K 38/1825* (2013.01); *A61K 38/18* (2013.01); *A61K 49/04* (2013.01); *A61K 49/06* (2013.01); *A61K 49/22* (2013.01); *A61K 51/00* (2013.01)

(58) Field of Classification Search
CPC .... A61K 38/1825; A61K 38/18; A61K 49/04; A61K 49/06; A61K 49/22; A61K 51/00
See application file for complete search history.

(56) References Cited

U.S. PATENT DOCUMENTS

| | | | |
|---|---|---|---|
| 5,671,741 A * | 9/1997 | Lang ................ G01R 33/56341 324/307 |
| 6,506,398 B1 * | 1/2003 | Tu .......................... A61F 2/062 424/423 |
| 6,933,286 B2 | 8/2005 | Emanuele et al. |
| 2002/0072667 A1 | 6/2002 | Kucharczyk et al. |
| 2002/0122792 A1 | 9/2002 | Stegmann |
| 2002/0155532 A1 | 10/2002 | Stegmann et al. |
| 2003/0103943 A1 | 6/2003 | Rosengart et al. |
| 2003/0139333 A1 | 7/2003 | Pawliuk et al. |
| 2003/0143207 A1 * | 7/2003 | Livesey ................ A61K 35/36 424/93.7 |
| 2003/0165473 A1 | 9/2003 | Masuda et al. |
| 2004/0052829 A1 | 3/2004 | Shrimp |
| 2004/0191215 A1 | 9/2004 | Froix et al. |
| 2004/0215334 A1 * | 10/2004 | Fernandes ................ A61F 2/07 623/1.41 |
| 2005/0239897 A1 * | 10/2005 | Pittenger ................ A61K 35/28 514/569 |
| 2007/0014773 A1 * | 1/2007 | Matheny ............. A61L 27/3633 424/93.21 |
| 2007/0053963 A1 | 3/2007 | Hotchkiss et al. |
| 2007/0059288 A1 * | 3/2007 | Dinsmore .......... A01K 67/0271 424/93.2 |
| 2007/0092492 A1 | 4/2007 | Matsuda et al. |
| 2007/0227547 A1 | 10/2007 | Trieu |
| 2007/0255130 A1 | 11/2007 | Du |
| 2009/0076481 A1 | 3/2009 | Stegmann et al. |
| 2009/0162287 A1 | 6/2009 | Lerche et al. |
| 2009/0317482 A1 | 12/2009 | Siani-Rose et al. |
| 2011/0223128 A1 | 9/2011 | Grutzendler et al. |

FOREIGN PATENT DOCUMENTS

| | | | | |
|---|---|---|---|---|
| CA | 2434058 A1 * | 7/2002 | ....... | A61B 17/12109 |
| WO | WO 2007011644 A2 * | 1/2007 | ......... | A61L 27/3633 |
| WO | 2007149548 A2 | 12/2007 | | |

(Continued)

OTHER PUBLICATIONS

Slavin, Cell Biology International, 19(50): 431-444, 1995.*

(Continued)

*Primary Examiner* — Titilayo Moloye

(74) *Attorney, Agent, or Firm* — Edwin S. Flores; Daniel J. Chalker; Chalker Flores, LLP

(57) ABSTRACT

Methods for the diagnosis and treatment of ischemic spinal conditions, degenerative disc disease, back pain and/or other tissue pathologies. Patients with ischemic spine disease can be categorized into subsets that are deemed to have potential to respond to therapy. In particular, therapies are disclosed which involve stimulation of neovascularization so as to increase perfusion of spinal and other anatomies.

15 Claims, 25 Drawing Sheets

(10 of 25 Drawing Sheet(s) Filed in Color)

(56) References Cited

FOREIGN PATENT DOCUMENTS

| WO | 2008109653 A2 | 9/2008 |
|---|---|---|
| WO | 2012121971 A2 | 9/2012 |

OTHER PUBLICATIONS

Aigner, T. et al., "SOX9 Expression Does Not Correlate with Type II Collagen Expression in Adult Articular Chondrocytes," Matrix Biology, (2003), 22:63-372.

Bernatchez et al., "Vascular Endothelial Growth Factor Effect on Endothelial Cell Proliferation, Migration, and Platelet-activating Factor Synthesis Is Flk-1-dependent," The Journal of Biological Chemistry, (1999), 274(43):31047-31054.

Bibby, S. R. et al., "Effect of Nutrient Deprivation on the Viability of Intervertebral Disc Cells," Eur. Spine J.,(2004), 13:695-701.

Boggild, H., "Ischemia and low-back pain—is it time to include lumbar angina as a cardiovascular disease?" Scand. J. Work Environ. Health, (2006). 32(1):20-21 (2006).

Boos, N. et al., "Classification of Age-Related Changes in Lumbar Intervertebral Discs: 2002 Volvo Award in Basic Science," Spine, (2002), 27:2631-2644.

Bydder, G.M. "New Approaches to Magnetic Resonance Imaging of Intervertebral Discs, Tendons, Ligaments and Menisci" 2002, Spine, vol. 27, No. 12, pp. 1264-1268.

Ceradini, D.J. et al., "Homing to Hypoxia: HIF-1 as a Mediator of Progenitor Cell Recruitment to Injured Tissue," Trends Cardiovasc. Med., (2005), 15(2):57-63.

Chang, S.C. et al., "Cartilage-derived morphogenetic proteins. New members of the transforming growth factor-beta superfamily predominantly expressed in long bones during human embryonic development," The Journal of Biological Chemistry, (1994), 269(45):28227-28234.

Chen, W et al., "Vertebral Bone Marrow Perfusion Evaluated with Dynamic Contrast-enhanced MR Imaging: Significance of Aging and Sex," Radiology, (2001), 220(1):213-218.

Cluroe, A.D. et al., "Combined Pathological and Radiological Study of the Effect of Atherosclerosis on the Ostia of Segmental Branches of the Abdominal Aorta" Pathology, (1992), 24:140-145.

Conway, E. M., "Angiogenesis: A link to Thrombosis in Atherothrombotic Disease," Pathophysiol. Haemost. Thromb., (2003) 33:241-248.

Crock, H.V., "Chapter 2: Internal Disc Disruption," The Practice of Spinal Surgery, Springer-Vienna, (1983), pp. 35-92.

Dvorak, H.F., "Angiogenesis: update 2005," Journal of Thrombosis & Hemostasis, (2005) 3:1835-1842.

Extended European Search Report for EP 14765582.3 dated Nov. 7, 2016, 7 pp.

Fingl, E. et al., "Chapter 1: General Principles," The Pharmacological Basis of Therapeutics, (1975), pp. 1-46.

Folkman, J., "Role of angiogenesis in tumor growth and metastasis," Semin, Oncol., (2002), 29(16):15-18.

Frymoyer, J.W. et al., "Chapter 8: The Economics of Spinal Disorders," The Adult Spine: Principles and Practice, Lippincott-Raven, (2nd ed. 1997), pp. 143-150.

Gray, M.J. et al., "HIF-1α, STAT3, CBP/p300 and Ref-1/APE are components of a transcriptional complex that regulates Src-dependent hypoxia-induced expression of VEGF in pancreatic and prostate carcinomas," Oncogene, (2005) 24:3110-3120.

Griffith, J.F. et al., "Vertebral Bone Mineral Density, Marrow Perfusion, and Fat Content in Healthy Men and Men with Osteoporosis: Dynamic Contrast-enhanced MR Imaging and MR Spectroscopy," Radiology, (2005), 236(3):945-951.

Gruber, H.E. et al., "Immunolocalization of MMP-19 in the human intervertebral disc: implications for disc aging and degeneration," Biotech. Histochem. (2005), 80(3-4):157-162.

Hart, L. et al., "Physician office visits for low back pain. Frequency, clinical evaluation, and treatment patterns from a U.S. national survey," Spine, (1995), 20(1):11-19.

Hatakeyama, Y. et al., "Smad Signaling in Mesenchymal and Chondroprogenitor Cells," J. Bone Joint Surg. A., (2003), 85A(3):13-18.

Haughton, V., "Imaging Intervertebral Disc Degeneration," J. Bone Joint Surg. Am., (2006), 88-A(2):15-20.

Heldin, C.H. et al., "TGF-β signalling from cell membrane to nucleus through SMAD proteins," Nature, (1997), 390, pp. 465-471.

Horner, H. A., et al., "2001 Volvo Award Winner in Basic Science Studies: Effect of Nutrient Supply on the Viability of Cells from the Nucleus Pulposus of the Intervertebral Disc," Spine, (2003), 26(23):2543-2549.

Hunter, C.J. et al., "The Functional Significance of Cell Clusters in the Notochordal Nucleus Pulposus: Survival and Signaling in the Canine Intervertebral Disc," Spine, (2004), 29(14):1099-1104.

Israel, D. I. et al., "Heterodimeric Bone Morphogenetic Proteins Show Enhanced Activity In Vitro and In Vivo," Growth Factors, (1996), V13:291-300.

Ivan, M. et al., "HIF-α Targeted for VHL-Mediated Destruction by Proline Hydroxylation: Implications for 02 Sensing," Science, (2001), 292:464-468.

Iwabuchi, M. et al., "Effects of Anulus Fibrosus and Experimentally Degenerated Nucleus Pulposus on Nerve Root Conduction Velocity: Relevance of Previous Experimental Investigations Using Normal Nucleus Pulposus," Spine, (2001),26(15):1651-1655.

Iwahashi, M. et al., "Mechanism of Intervertebral Disc Degeneration Caused by Nicotine in Rabbits to Explicate Intervertebral Disc Disorders Caused by Smoking," Spine, (2002), 27(13):1396-1401.

Kauppila, L.I. et al, "Postmortem Angiographic Findings for Arteries Supplying the Lumbar Spine: Their Relationship to Low-Back Symptoms," J. Spinal Disord., (1993), 6(2):124-129.

Kauppila, L.I. et al., "Lumbar Disc Degeneration and Atherosclerosis of the Abdominal Aorta," Spine, (1994), 19(8):923-929.

Kauppila, L.I., "Blood Supply of the Lower Thoracic and Lumbosacral Regions: Postmortem Aortagraphy in 38 Young Adults," Acta Radiol., (1994), 35:541-544.

Kauppila, L.I. et al., "Can Low-Back Pain Be Due to Lumbar-Artery Disease?," Lancet, (1995), 346:888-889.

Kauppila, L. et al., "Disc Degeneration/Back Pain and Calcification of the Abdominal Aorta: A 25-Year Follow-Up Study in Framingham," Spine, (1997), 22(14):1642-1649.

Kim, K.S. et al., "Inhibition of Proteoglycan and Type II Collagen Synthesis of Disc Nucleus Cells by Nicotine," Journal Neurosurg., (2003), 99(3):291-297.

Konttinen, Y. T. et al., "Transforming and Epidermal Growth Factors in Degenerated Intervertebral Discs," J. Bone Joint Surg. [Br], (1999), 81-B:1058-1063.

Kroll, P. et al. "Which Treatment is Best for Which AMP Patient?" Br. J. Opthalmol., (2006), 90:128-130.

Kurunlahti, M. et al., "Association of Atherosclerosis with Low Back Pain and the Degree of Disc Degeneration," Spine, (1999), 24(20):2080-2084.

Kurunlahti, M. et al., "Correlation of Diffusion in Lumbar Intervertebral Disks with Occlusion of Lumbar Arteries: A Study in Adult Volunteers," Radiology, (2001), vol. 221:779-186.

Laroche, M. et al., "Comparison of the Bone Mineral Content of the Lower Limbs in Men With Ischaemic Atherosclerotic Disease," Clin. Rheumatol., (1994), 13:61-614.

Larsson, H.B.W. et al., "Myocardial Perfusion Modeling Using MRI," MRM, (1996), 35:716-726.

Levicoff, E.A. et al., "Gene Therapy for Disc Repair," The Spine Journal, (2005), 5:287S-296S.

Li, J. et al., "Increased Responsiveness of Hypoxic Endothelial Cells to FGF2 is Mediated by HIF-1α-Dependent Regulation of Enzymes Involved in Synthesis of Heparin Sulfate FGF2-Binding Sites," Journal of Cell Science, (2002), 115:1951-1959.

Li, Y. et al., "Transduction of Passaged Human Articular Chondrocytes with Adenoviral, Retroviral, and Lentiviral Vectors and the Effects of Enhanced Expression of SOX9," Tissue Engineering, (2004), 10(3/4):575-584.

Lindstedt et al., "Blood Flow Changes in Normal and Ischemic Myocardium During Topically Applied Negative Pressure," Ann. Thor. Surg, (2006), 84: 568-573.

(56) References Cited

OTHER PUBLICATIONS

Liu, L. et al., "Regulation of Transcription and Translation by Hypoxia," Cancer Biology & Therapy, (2004), 3(6):492-497.
Lively, N.M., "Sports Medicine Approach to Low Back Pain," South Med. J., (2002), 95(6):642-646.
Maruotti, N. et al., "Angiogenesis in Rheumatoid Arthritis," Histology and Histopathology, (2006), 21:557-566.
Masuda, K. et al., "Recombinant Osteogenic Protein-1 Upregulates Extracellular Matrix Metabolism by Rabbit Annulus Fibrosus and Nucleus Pulposus Cells Cultured in Alginate Beads," J. Orthop Res., (2003), 21:922-930.
Masuda, K. et al., "Growth Factors and Treatment of Intervertebral Disc Degeneration," Spine, (2004), 29:2757-2769.
Mitchell, J.R. et al. "Aortic Size and Aortic Calcification: A Necropsy Study," Atherosclerosis, (1977), 27:437-446.
Mizukami, Y. et al., "Hypoxic Regulation of Vascular Endothelial Growth Factor Through the Induction of Phosphatidylinositol 3-Kinase/Rho/ROCK and c-Myc," J. Biol. Chem., (2006), 281(20):13957-13963.
Nagase, et al. "Matrix Metalloproteinases," The Journal of Biological Chemistry, (1999), 274(31):2191-21494.
Naves, L.A. et al., "An Acid-Sensing Ion Channel that Detects Ischemic Pain," Braz. J. Med. & Biol. Research, (2005), 38:1561-1569.
Nohe, A. et al., "Signal Transduction of Bone Morphogenetic Protein Receptors," Cellular Signalling, (2004), 16:291-299.
Ohshima, H. et al., "The Effect of Lactate and pH on Proteoglycan and Protein Synthesis Rates in the Intervertebral Disc," Spine, (1992), 17(9):1079-1082.
Omlor, G.W. et al., "Changes in Gene Expression and Protein Distribution at Different Stages of Mechanically Induced Disc Degeneration—An In Vivo Study on the New Zealand White Rabbit," J. Orthop. Res., (2006), 24:385-392.
Paul, R. et al., "Potential Use of Sox9 Gene Therapy for Intervertebral Degenerative Disc Disease," Spine, (2003), 28(8), phs. 755-769.
Pear, W.S. et al., "Lasting Longer Without Oxygen: The Influence of Hypoxia on Notch Signaling," Cancer Cell, (2005), 8:435-437.
Pfirrmann, C. et al., "Magnetic Resonance Classification of Lumbar Intervertebral Disc Degeneration," Spine, (2001), 26(17)1873-1878.
Rajasekaran, S. et al., "ISSLS Prize Winner: A Study of Diffusion in Human Lumbar Discs: A Serial Magnetic Resonance Imaging Study Documenting the Influence of the Endplate on Diffusion in Normal and Degenerate Discs," Spine, (2004),29:2654-2667.
Razaq, S. et al., "The Effect of Extracellular pH on Matrix Turnover by Cells of the Bovine Nucleus Pulposus," Eur. Spine J., (2003), 12:341-349.
Robbers, et al., "Magnetic Resonance Imaging-defined Areas of Microvascular Obstruction After Acute Myocardial Infarction Represent Microvascular Destruction and Haemorrhage," European Heart Journal, (2013), 34: 2346-2353.
Roberts, S. et al., "Matrix Metalloproteinases and Aggrecanase: Their Role in Disorders of the Human Intervertebral Disc," Spine, (2000), 25(23):3005-3013.
Ross, R., "Chapter 50: Atherosclerosis," Cecil's Textbook of Medicine, W.B. Saunders Company, Canada/U.S. Publication, (1998), vol. 1, 18th ed., p. 318-323.
Roughley, P.J., "Biology of Intervertebral Disc Aging and Degeneration," Spine, (2004), 29(23) pp. 2691-2699.
Sampath, T.K. et al., "In Vitro Transformation of Mesenchymal Cells Derived From Embryonic Muscle into Cartilage in Response to Extracellular Matrix Components of Bone," Proc. Nat'l Acad. Sci. USA, (1984), 81:3419-3423.

Seguin, C.A. et al., "Tumor Necrosis Factor-$\alpha$ Modulates Matrix Production and Catabolism in Nucleus Pupolsus Tissue," Spine, (2005), 30(17):1941-1948.
Setton, L.A. et al., "Cell Mechanics and Mechanobiology in the Intervertebral Disc," Spine, (2004), 29(23):2710-2723.
Sharkey, A.M. et al., "Novel Antiangiogenic Agents for Use in Contraception," Contraception, (2005), 71:263-271.
Shih, T. et al. "Correlation of MR Lumbar Spine Bone Marrow Perfusion With Bone Mineral Density in Female Subjects," Radiology, (2004), 233(1):121-128.
Shimer, A. L. et al. "Gene Therapy Approaches for Intervertebral Disc Degeneration," Spine, (2004), 29(23):2770-2778.
Simons, M., "Angiogenesis: Where Do We Stand Now?" Circulation, (2005), 111:1556-1566.
Soukane, M.D. et al., "Computation of Coupled Diffusion of Oxygen, Glucose and Lactic Acid in an Intervertebral Disc," Journal of Biomechanics, (2007), 40:2645-2654.
Takegami, K. et al., "Osteogenic Protein-1 Enhances Matrix Replenishment by Intervertebral Disc Cells Previously Exposed to Interleukin-1," Spine, (2002), 27(12):1318-1325.
Thompson, J.P. et al., "Stimulation of Mature Canine Intervertebral Disc by Growth Factors," Spine, (1991), 16(3)253-260.
Urban, J. P., et al., "Nutrition of the Intervertebral Disc," Spine, (2004), 29(23):2700-2709.
Urban, J. P., et al., "Pathophysiology of the Intervertebral Disc and the Challenges for MRI," J Magn Reson Imaging (2007), 25:429-432.
Voros, G. et al. "Modulation of Angiogenesis During Adipose Tissue Development in Murine Models of Obesity," Endocrinology, (2005), 146(10):4545-4554.
Walker, M.H. et al., "Molecular Basis of Intervertebral Disc Degeneration," The Spine Journal, (2004), 4:158S-166S.
Wallach, C.J. et al., "Gene Transfer of the Catabolic Inhibitor TIMP-1 Increases Measured Proteoglycans in Cells from Degeneration Human Intervertebral Discs," Spine, (2003), 28(20):2331-233.
Workie, D.W. et al., "Quantification of Dynamic Contrast-Enhanced MR Imaging of the Knee in Children With Juvenile Rheumatoid Arthritis Based on Pharmacokinetic Modeling," MRI, (2004), 22:1201-1210.
Yamamoto, Y. et al., "Upregulation of the Viability of Nucleus Pulposus Cells by Bone Marrow-Derived Stromal Cells," Spine, (2004), 29(14), pp. 1508-1514.
Yoon, S.T. et al., "ISSLS Prize Winner: LMP-1 Upregulates Intervertebral Disc Cell Production of Proteoglycans and BMPs In Vitro and In Vivo," Spine, (2004), 29(23):2603-2611.
Yoon, S.T., "Molecular Therapy of the Intervertebral Disc," The Spine Journal, (2005), 5:280S-286S.
Zhang, Y. et al., "Growth Factor Osteogenic Protein-1: Differing Effects of Cells from Three Distinct Zones in the Bovine Intervertebral Disc," Am. J. Phys. Med. Rehavil., (2004), 85:515-521.
Xue Xia et al: "Pharmacokinetic Properties of 2nd-Generation FibroblastGrowth Factor-1 Mutants for Therapeutic Application", PLoS One, Nov. 1, 2012 (Nov. 1, 2012 ).
Badami et al. "Ischemic index as a predictor of response to antivegf therapy." Investigative Ophthalmology & Visual Science Sep. 2016, vol. 57, 2092. (Year: 2016).
Hartig SM "Basic image analysis and manipulation in ImageJ." Curr Protoc Mol Bioi. 2013;Chapter 14:Unit14.15. (Year: 2013).
Emory University. "Anatomy Manual: The Vertebral Column and Spinal Cord." Accessed from http://www.emory.edu/ANATOMY/AnatomyManual/back.html on Apr. 2, 2019. (Year: 2019).
International Searching Authority, United States Patent and Trademark Office, Forms PCT/ISA/210/220/237 for IA Application No. PCT/US2014/027866, International Search Report, Written Opinion and Examiner's Search Strategy, dated Sep. 22, 2014.

\* cited by examiner

A

B

A

B

A

B

525

THERAPEUTIC ANGIOGENESIS FOR TREATMENT OF THE SPINE AND OTHER TISSUES

CROSS REFERENCE TO RELATED APPLICATIONS

This application is a continuation-in-part of U.S. patent application Ser. No. 12/076,846 entitled "Therapeutic Angiogenesis for Treatment of the Spine" to Stegmann et al, filed Mar. 24, 2008, which claims priority to U.S. Provisional Patent Application Nos. 60/920,254, filed Mar. 27, 2007 and 61/022,266, filed Jan. 18, 2008. Each of these applications is expressly incorporated herein by reference in its entirety.

BACKGROUND OF THE INVENTION

Field of the Invention

The various embodiments herein pertain to the field of diagnosing and treating spinal disorders and/or other tissue disorders, which may including disorders that present with lower back or other pathology. Embodiments relate to methods for diagnosing and/or treating disorders causative, or being precursors to, degeneration of spinal and/or other anatomy. In particular embodiments, treatments include methods of increasing angiogenesis in response to specifically diagnosed conditions.

Description of the Related Art

Musculoskeletal disorders of the spine are an extremely common occurrence associated with debilitating back pain, leading to enormous psychosocial and economic ramifications. Lower-back pain is the leading source of disability in people under 45 years of age, and it results in significant economic losses. Eighty percent of people in the United States will experience back pain at some point in their lifetime, and it is the second most common reason for symptomatic physician visits. Causes of back pain range from injury induced, which often presents as a minor problem, accelerating to a chronic disorder, as well as degenerative spine diseases that lead to degenerative spondylolisthesis and spinal stenosis. The vast majority of chronic back pain is associated with degeneration of the intervertebral disc, which can manifest in many different clinical conditions including spinal stenosis and instability, radiculopathy, myelopathy, and disc herniation.

The human spine is composed of bony structures called vertebrae, separated by intervertebral discs. One of the main functions of the vertebrae is to provide structural support and protection for the spinal cord. Each vertebra is comprised of a spinous process, a bony prominence behind the spinal cord, which shields the cord's nervous tissue on the back side, two bony protrusions on the sides called transverse processes, and a "body" in front of the spinal cord which provides a structural support for weight bearing. The average adult has 24 vertebrae, although at birth 33 are present. Reduction in the number of vertebrae is primarily due to fusion during normal development. The vertebrae are divided by anatomical locations with 7 in the neck, also called the cervical vertebrae, 12 in the middle back, called the thoracic vertebrae, 5 in the lower back, called the lumbar vertebrae, and the sacrum, which is actually formed from five fused vertebrae. The tailbone, called the coccyx is made of three fused vertebrae. Of these, the lumbar vertebrae are the largest, in part since they are responsible for carrying the majority of body weight. In general, the lumbar area is associated with the highest level of degeneration and is believed causative for a wide variety of pain-inducing syndromes.

Separating the vertebrae are soft intervertebral discs that, together with the two facet joints, allow for movement of the vertebrae and therefore provide the ability of the spine to move in various directions. The complex of two facet joints posteriorly and the disc anteriorly is referred to as a spinal segment. The intervertebral disc includes the annulus fibrosus, the nucleus pulposus, and the cartilage endplates. The nucleus pulposus includes anionic proteoglycans, such as aggracan, that have high affinity for water, and provide a cushioning and shock-absorbing function. The annulus fibrosus encapsulates the nucleus pulposus, and includes concentrically organized layers of collagen fibrils (lamellae). The composition of the nucleus pulposus is distinctly different than the annulus fibrosus since the former primarily includes a jelly-like substance and high collagen type I, whereas the latter is made of a solid, fibrotic-like texture, primarily containing collagen type II. In an adult, the cartilage endplate is composed primarily of hyaline cartilage and serves to separate the nucleus pulposus and annulus fibrosus from the adjacent vertebral bone. Discogenic pain often arises from areas of the annulus fibrosus. As a matter of fact, pain-associated molecules such as Substance P and TNF (Tumor Necrosis Factor) have been identified in large concentrations in biopsy samples of patients suffering discogenic pain, but not in controls.

Each disc provides motion and binds the segments together through its 95% non-cellular and 5% cellular components. Nutrition to the disc cells (or chondrocytes) is primarily provided by arteries that arise off of the major blood vessel in the body (called the aorta) and wrap around each vertebral body, penetrating the bone along its circumference. The arteries course through the vertebral body (bone) and then turn towards the disc at either end. The oxygen, glucose and other nutrients are "dropped off" where the disc attaches to the bone and the capillaries and venules form a vascular loop. The cartilage that is in contact with these vascular loops is called the "endplate." The nutrients "diffuse" (or move through the endplate and disc tissue without being transported in blood vessels) into the middle of the disc (or nucleus). In addition to this pathway, arterioles deliver nutrients to the outer edge of the disc (annulus) directly (this pathway provides minimal nutrients to the nucleus in normal discs, but might be exploited in angiogenic treatment). Once the nutrients reach the cell, they are taken up and utilized for the manufacture of materials that make up the disc (extracellular matrix: collagen and proteoglycans). Recent studies have demonstrated that cartilage cells require oxygen to produce enough energy for the proper manufacture and maintenance of the extracellular matrix. If the cells do not receive enough oxygen, the manufacturing process stops and the disc becomes acidic (pH drops). As the nutrient supply is cut off, the cells in the disc begin to die and the disc tissue begins to breakdown. This loss of nutrients is thought to be the initial cause of degenerative disc disease. As the disc continues to degenerate and the cell population decreases, the oxygen concentration may return to normal due to less demand. At this stage, regeneration may be a possibility. However, excessive mechanical loading on a weakened structure precipitates further degeneration which may lead to structural defects such as endplate fracture, radial fissures and herniation. As cells continue to produce energy through anaerobic processes, low pH creates further cell death and possibly ultimate irreversible processes.

Although disc degeneration continues to have a tremendous and ever-increasing impact worldwide, current treatment options do not address the underlying cause. Current treatments include bed rest, nonsteroidal anti-inflammatory medication in the early phases of pathology, and procedures such as discectomy, arthroplasty (joint replacement), injection of artificial nucleus pulposus and fusion in the later phases when the prior approaches did not ameliorate pain. Such approaches are unpredictable, and deal almost exclusively with end-stage clinical manifestations, and therefore do nothing to alter the disease process itself. Additionally, procedures such as vertebral fusion result in the increased incidence of disc degeneration in the adjacent discs due to alterations in the biomechanical distribution of work-load.

Recent advances in both biotechnology and our understanding of the biochemical makeup and environment of the intervertebral disc have led to increased interest in the process of degeneration and the possibility of developing novel treatments aimed directly at disc preservation. Certain genes found to have significant impact on matrix synthesis and catabolism within the disc have provided targets for scientists seeking to alter the balance between the two. To this end, much attention over the past several years has centered on gene therapy, and these efforts have yielded some promising preclinical results with regard to its use in treating disc degeneration. Unfortunately, none of these approaches are near clinical implementation at this time. Additionally, it is important to note that even in the circumstance that disc regeneration alone can be achieved through gene therapy or other interventional means, the underlying process that originally caused the degeneration must be addressed in order to prevent recurrence.

Currently, no biological treatment is widely available for disc degeneration. However, many different molecules of potential therapeutic benefit are being investigated. The focus of molecular therapy has been to prevent or reverse one or more aspects of these changes in the disc extracellular matrix. At least four different classes of molecules may be effective in disc repair. These include anticatabolics, mitogens, chondrogenic morphogens and intracellular regulators. Hallmarks of disc degeneration include loss of proteoglycans, water, and Type II collagen in the disc matrix. Furthermore, other qualitative changes in the matrix are less well defined, including loss of the higher molecular weight proteoglycans, and other changes that are more difficult to quantify (collagen cross-linking, organization of the proteoglycan, etc). An important process in disc degeneration seems to be the change of the differentiated chondrocyte phenotype in the nucleus pulposus into a more fibrotic phenotype. Together these changes in the disc matrix lead to alteration of the disc and vertebral anatomy that ultimately is associated with a pathologic condition.

Because matrix loss is a balance between matrix synthesis and degradation, it is possible to increase disc matrix by increasing synthesis or by decreasing degradation. One approach is to prevent matrix loss by inhibiting the degradative enzymes. Degenerated discs have elevated concentrations of matrix metalloproteinases (MMPs). Within the matrix, MMP activity is normally inhibited by tissue inhibitors of MMPs (TIMPs). Wallach, et al. (*Spine* 28:2331-2337, 2003) tested whether one of these anticatabolic molecules, TIMP-1, could increase the accumulation of matrix proteoglycans with in vitro experiments. The researchers found that indeed TIMP-1 expression in disc cells increased accumulation and also increased the "measured synthesis rate" of proteoglycans. Chondrogenic morphogens are cytokines that not only possess mitogenic capability but are characterized by their ability to increase the chondrocyte-specific phenotype of the target cell. Most of the research in chondrogenic morphogens has been performed with transforming growth factor-β (TGF-β), bone morphogenetic proteins (BMPs) or growth and differentiation factors (GDFs). Chondrogenic morphogens are particularly attractive because they may reverse the fibrotic phenotype of disc cells to the more chondrocytic phenotype of disc nucleus cells in younger and more "normal" discs. By definition, these molecules are secreted molecules and hence can potentially act in autocrine, paracrine and endocrine fashion. TGF-β1 is one of the first disc morphogenic molecules to be studied. TGF-β1 is a mitogen, but also appears to be highly anabolic molecule leading to significantly increased proteoglycan synthesis per cell. Gene transfer of TGF-β using an adenoviral/CMV vector may be capable of reversing radiological signs of disc degeneration in rabbit models.

BMP-2 is another prototypic chondrogenic morphogen. Recombinant human BMP-2 has been reported to increase production of rat disc cell proteoglycans and significantly increase the chondrocytic phenotype of the disc cells as shown by increased aggrecan and Type II collagen gene expression, with no change in Type I collagen gene expression. BMP-2 has been reported to partially reverse the inhibitory effect of nicotine on the synthesis of disc cell proteoglycan. BMP-7, also known as OP-1 (Osteogenic Protein-1), is another disc cell morphogen that has demonstrated potent in vitro activity in terms of enhancing matrix formation in disc cells. Growth differentiation factor 5 (GDF-5) is also known as CDMP-1 (Cartilage-derived morphogenetic protein 1) has also been considered for regeneration of disc cells.

Intracellular regulators are a distinct class of molecules because they are not secreted and do not work through transmembrane receptors. These molecules are neither cytokines nor growth factors in the classical sense, and yet they can have effects that are quite similar to the secreted molecules discussed previously. This class of molecules typically controls one or more aspects of cellular differentiation. For instance, Sma-Mad (SMAD) proteins are intracellular molecules that mediate BMP-receptor signaling. Although there are no specific published papers on the effect of SMAD proteins on disc cells, proteins such as Smad-1 and Smad-5 are predicted to induce similar effects on disc cells as BMP-2, such as increasing proteoglycan and Type II collagen synthesis. Sox9 (transcription factor) is a chondrocyte marker that is a positive regulator of Type II collagen mRNA transcription. It has also been shown that Sox9 delivered by adenovirus can increase Sox9 expression and disc cell production of Type II collagen in in vitro experiments.

The success of a disc tissue engineering strategy can be dependent on molecular cues to direct the differentiation of cells and affect their biosynthetic function. Many growth factors, including members of the transforming growth factor beta superfamily, affect the differentiation process of disc cells. This group of related proteins directs the induction of mesenchymal precursors to form mature skeletal tissues. The activity of these molecules is complex and affects intercellular signaling pathways. In addition, concentration and timing of presentation of the growth factor influences its activity. Depending on the tissue, the effects of a given morphogen may be different. For instance, the osteogenic molecule bone morphogenetic protein-7-osteogenic protein-1 (BMP-7/OP-1) has been shown to have a dramatic effect on disc cells, increasing their metabolic output of matrix proteins and rescuing them from the detrimental effects of Interleukin 1 (IL-1). This data suggests that growth factors could play a useful role in a cell-based tissue engineering strategy.

Other yet to be identified factors direct cell-to-cell communication and appear to play an important role in the viability and metabolic activity of disc cells. It has been shown that cell proliferation and proteoglycan synthesis can be significantly enhanced in disc cells cultured in a system that allows direct cell-cell contact with bone marrow-derived stromal cells. Other studies have reported that enzymatic disruption of gap junctions can produce a negative effect on cell viability, suggesting that cellular communication plays a vital role in cell viability and function, and therefore interventions supporting their enhancement may be beneficial.

SUMMARY OF THE INVENTION

The present invention relates to methods for diagnosing, quantifying, assessing, and/or treating or ameliorating painful and/or degenerative conditions of the spine, including those that ultimately involve lower back pain. Embodiments can include classifications of disc nutrition deficit, pathological conditions and/or associated back pain measured that can be based on specific parameters associated with hypoperfusion, hypoxia, and ischemia. Further embodiments relate to treatments for alleviating the state of hypoperfusion, hypoxia, and ischemia in patients in which alleviation of said hypoperfusion may lead to therapeutic improvement.

Various embodiments described herein can be employed to diagnose, assess, quantify and/or treat pathologies that can eventually lead to deficient nutrition to and/or waste removal from the intervertebral disc or other tissues. In an initial step, anatomical image data is obtained of an individual patient's anatomy. This image data can be derived from a wide variety of sources, including MRA (magnetic resonance angiography), MRI (magnetic resonance imaging), x-ray imaging, cone beam CT, digital tomosynthesis, and ultrasound, CT scans or PET or SPECT scans, as well as many others known in the art. Once image data is acquired, one or more regions of interest (ROI) of the image data can be identified and analyzed in a variety of ways, and the analyzed results can be compared to a defined value and/or standard and utilized to diagnose, assess and/or quantify a pathology. If desired, the analysis and diagnosis can be used as guidance for treating the patient. In various other embodiments, the results can be compared to values derived or obtained from a reference database of healthy and/or diseased patients. In other alternative embodiments, a relative assessment of such values within an individual patient can be conducted, which may be used to identify abnormal and/or anomalous readings, which may be indicators of relative deficiencies.

Various embodiments described herein can be employed to diagnose, assess, quantify and/or treat pathologies that can eventually lead to deficient nutrition to and/or waste removal from the intervertebral disc or other tissues. The nutrient supply to an intervertebral disc can potentially be blocked at various stages of the route. The feeding arteries or other vascular structures themselves can narrow due to atherosclerosis with resultant ischemia of the vertebral body. With less blood flowing through the vertebrae, less oxygen and nutrients are available to diffuse into the disc creating hypoxia, lower pH and cell death. In addition to and/or instead of narrowing of the major lumbar vessels, the decreasing blood flow within the vertebral body can be a primary reason for the loss of nutrients and the onset of degenerative disc disease. Trauma can disrupt blood and/or nutrition flow. Degenerative disc disease due to nicotine and aging can also demonstrate a loss of nutritive blood vessels in the area supplying nutrients. Eventually, the endplate itself can become a hindrance to the diffusion of nutrients, potentially creating another obstacle to proper disc chondrocyte nutrition.

In an embodiment, the diagnosis of hypoxic or ischemic disc disease or "lumbar ischemia" as a disorder can be made by a two-part test of firstly excluding patients with a set exclusion criteria, and further selecting patients having documented hypoperfusion, hypoxia, or ischemia of the affected areas. Specific exclusion criteria include, for example, one or more of the flowing including the presence of herniated disc, spinal infection, spinal tumor, spinal arthritis, and spinal canal stenosis.

Embodiments of the invention are directed to methods of diagnosing a condition responsible for degenerative disc disease or vertebral osteoporosis, which may include one or more of the following steps:

a) assessing a patient by one or more of the following steps:
   (i) classifying patency of said one or more lumbar segmental vessels;
   (ii) determining blood perfusion in the anatomical areas supplied by said segmental vessels;
   (iii) determining extent of disc degeneration or vertebral osteoporosis;
b) correlating data collected from (a(i)) with data collected from (a(ii)) and with data collected from (a(iii));
c) producing an overall index of correlation; and
d) comparing said index of correlation with an index of correlation generated from a healthy population.

In another exemplary embodiment, a method of diagnosing a condition responsible for degenerative disc disease could include one or more of the following steps:

a) assessing a patient by one or more of the following steps:
   (i) obtaining image data of one or more vertebral bodies of the patient;
   (ii) identifying one or more regions of interest within the image data;
   (iii) analyzing the one or more regions of interest to identify one or more areas of intravertebral hypoperfusion proximate to one or more endplates; and
   (iv) diagnosing the patient with said intravertebral hypoperfusion proximate to one or more endplates.

In one exemplary embodiment, diagnosed intravertebral hypoperfusion can be treated by increasing perfusion in identified area(s) such as by injection of a composition that includes an angiogenic factor. In preferred embodiments, injection can be directly into the vertebral body to a location within and/or proximate to the identified area or areas of hypoperfusion. The identified area or areas can be accessed via one or more of the pedicles of the vertebral body with a surgical access and delivery device such as a surgical access needle extending through the patient's skin and overlying soft tissues in a minimally-invasive manner, extending through one or more pedicles and into the vertebral body located proximate to the vertebral endplate. The composition can then be introduced into the vertebral body through the delivery device.

In various embodiments, hypoxic and/or ischemic disc disease is treated by increasing perfusion in the affected area such as by injection of a composition that includes an angiogenic factor. In preferred embodiments, injection is around the vertebrae or directly into the vertebral body. In other embodiments, injection of angiogenic compounds may be positioned into and/or adjacent to other anatomical structures, including the annulus of the disc and/or arterioles. In some embodiments, a localized delivery system capable of forming a gel-like structure may be used to deliver the angiogenic factor. Preferably, the delivery system includes components of extracellular matrix that provide conditions suitable for angiogenesis. In some embodiments, said extracellular matrix components may be hyaluronic acid fragments. In other embodiments, said extracellular matrix components may be derivatives of collagen, or perlecan. Preferably, the gel-like structure includes a polymer capable of slow release such as a poloxamer block copolymer (Pluronic®, BASF), basement membrane preparation (Matrigel®, BD Biosciences) or collagen-based matrix such as described by U.S. Pat. No. 6,346,515, which is incorporated herein by reference.

In various embodiments, hypoxic and/or ischemic disc disease can be treated by administration of a medical device that generates a continuous release of a composition which includes an angiogenic factor into tissue and/or circulation so as to promote neoangiogenesis, and specifically, collateralization in the area(s) proximal to hypoperfusion. In some embodiments, the composition could further include stem cells and/or other biological treatments, which might be used in conjunction with angiogenic factors prior to, during and/or subsequent to the employment of tissue grafts to repair or replace native tissues. If desired, such compositions could be used to prepare a patient's anatomical site for an intended tissue graft or surgical procedure, could be used to prepare the tissue graft for implantation, and/or could be used to treat the patient and/or tissue graft site after implantation.

In various embodiments, a medical device may include a slow release pump such as an implantable indwelling or osmotic pump or a localized delivery system such as a polymer capable of slow release, as described herein.

In an embodiment, the composition delivered by the medical device contains not only a therapeutically sufficient concentration of a growth factor that stimulates angiogenesis, but also a chemotactic agent. Some growth factors, such as fibroblast growth factor 1 (FGF-1), are themselves chemotactic. The chemotactic agent recruits cells capable of causing or promoting angiogenesis. In some embodiments, a chemotactic agent such as stromal cell-derived factor 1 (SDF-1) is included in the composition with the growth factor. In various embodiments, the composition delivered by the medical device may contain an anti-inflammatory agent at a concentration sufficient for inhibiting possible inflammatory reactions associated with neoangiogenesis, while at the same time not inhibiting collateral blood vessel formation.

Depending upon the specific tissue structure(s) concerned, the diagnosis and/or treatment methods and systems described herein can include the selection and analysis of a plurality of relevant tissue structures. For example, where the diagnosis and/or treatment of a patient's intervertebral disc is of interest, the methods and systems described herein can include the imaging and analysis of intravertebral structures of vertebral bodies proximate to both the cephalad and caudad endplates of the intervertebral disc of interest. Depending upon the physician's preference and/or the relevant clinical situation, diagnosis of intravertebral hypoperfusion of either or both of the disc endplates may indicate a need for further treatment, as described herein.

In various embodiments, assessment of perfusion can be performed, followed by therapy that increases the rate of perfusion, followed by a subsequent assessment of perfusion so as to identify the ideal conditions for stimulation of perfusion on an individualized basis.

BRIEF DESCRIPTION OF THE DRAWINGS

Color Drawings

The patent or application file contains at least one drawing executed in color. Copies of this patent or patent application publication with color drawing(s) will be provided by the Office upon request and payment of the necessary fee.

Figure 1:
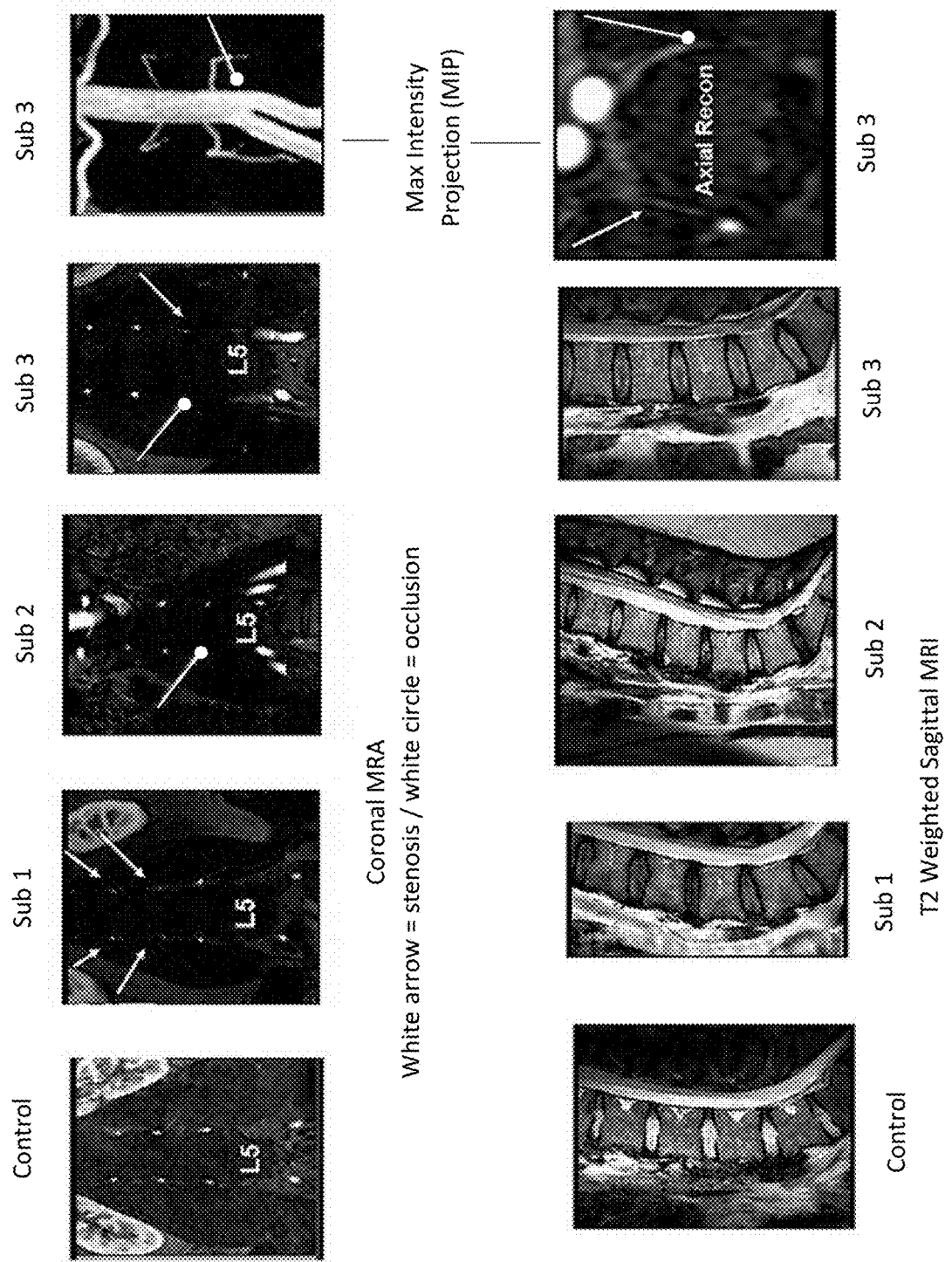
Figure 2:
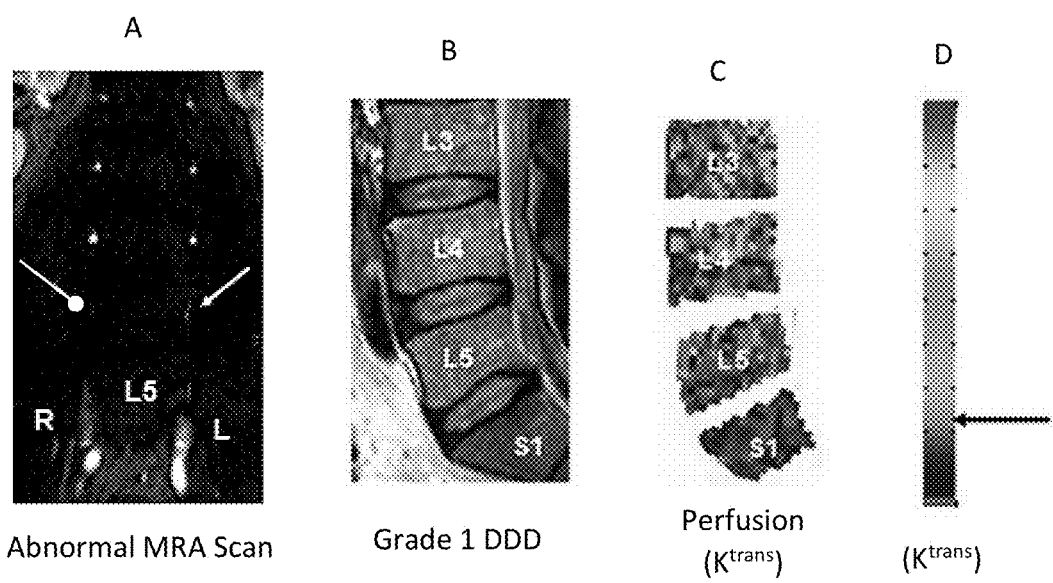
Figure 3:
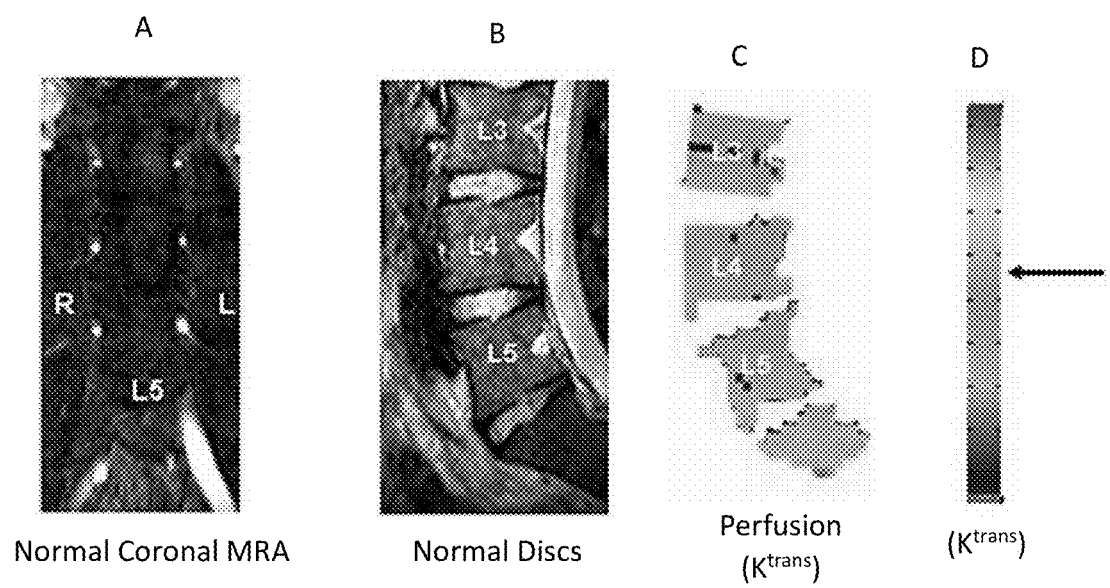
Figure 4:
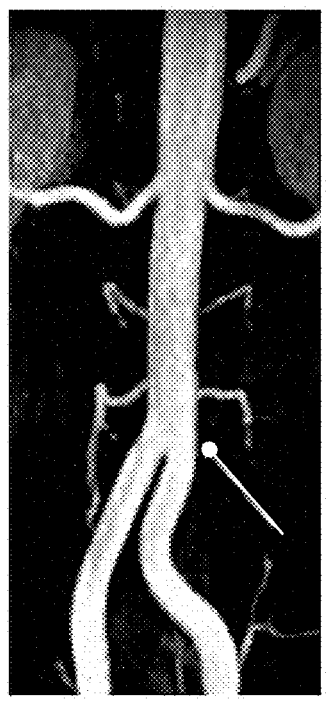
Figure 4:
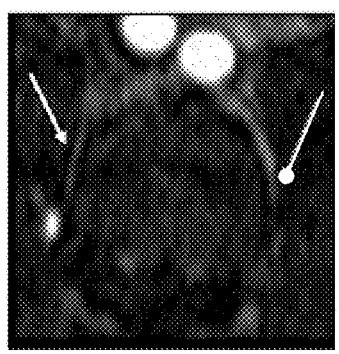
Figure 5:
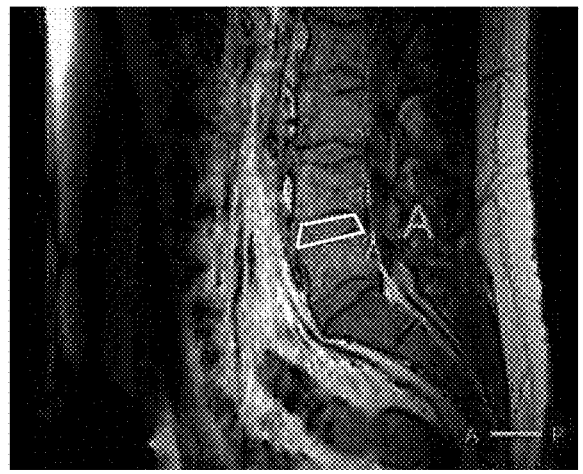
Figure 5:
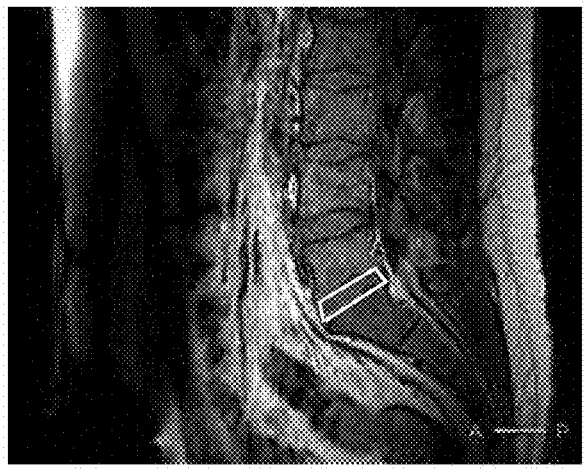
Figure 6:
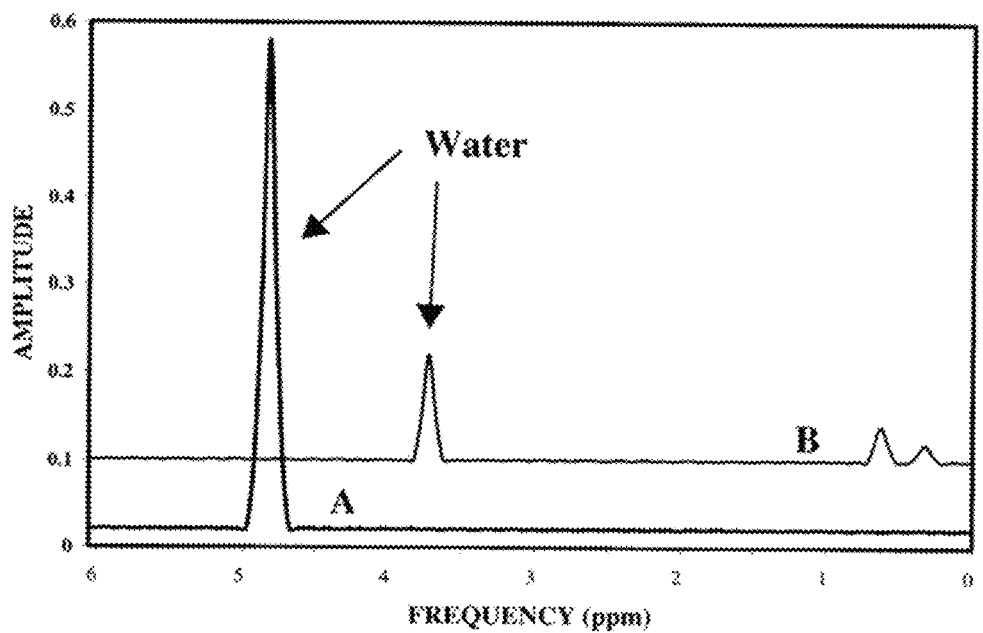
Figure 6:
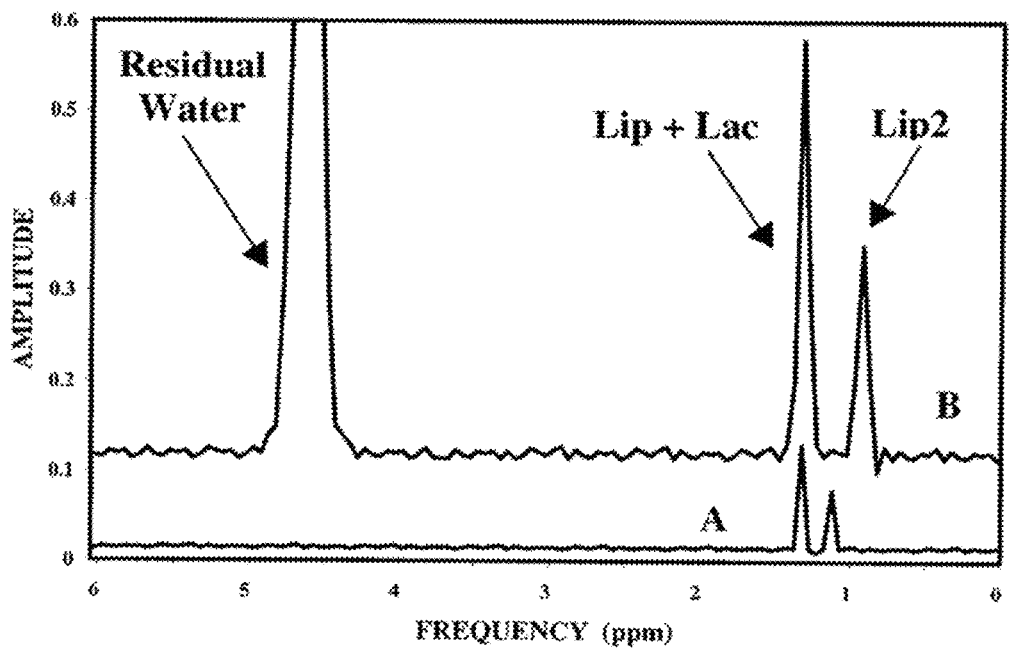
Figure 7A:
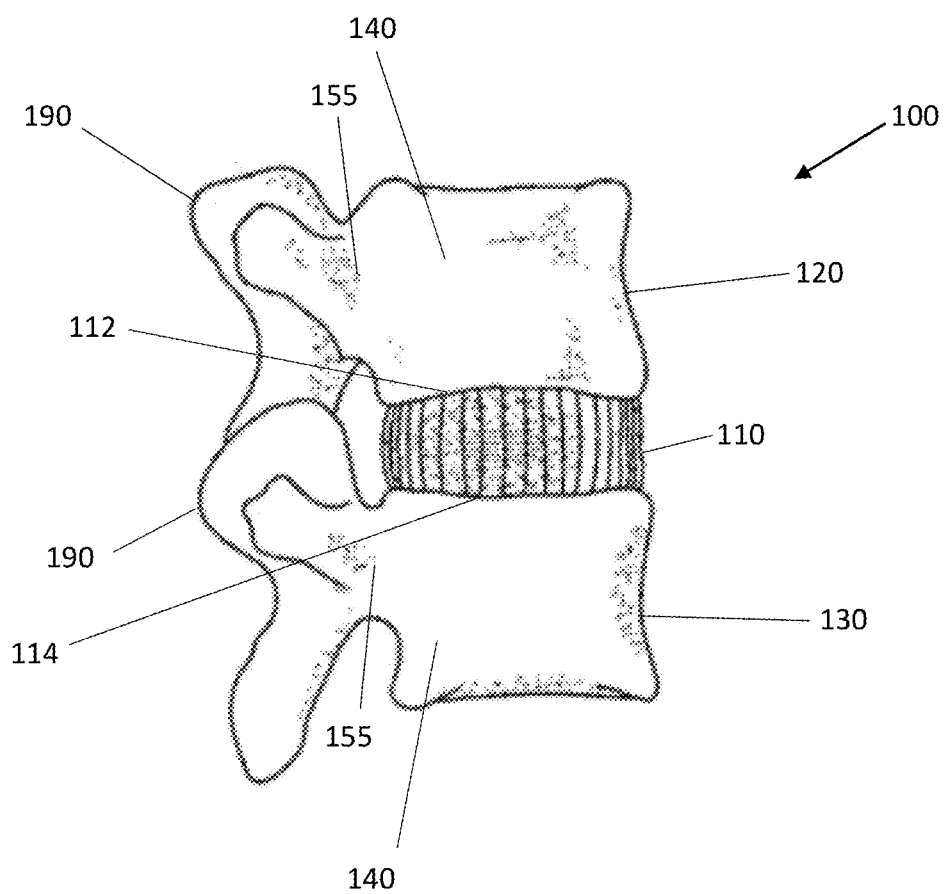
Figure 7B:
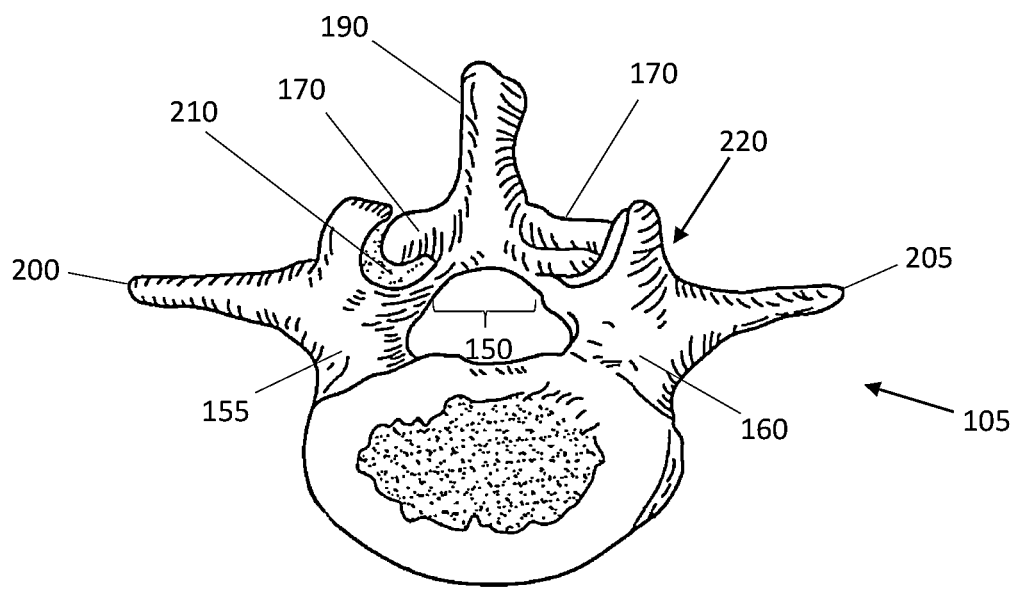
Figure 7C:
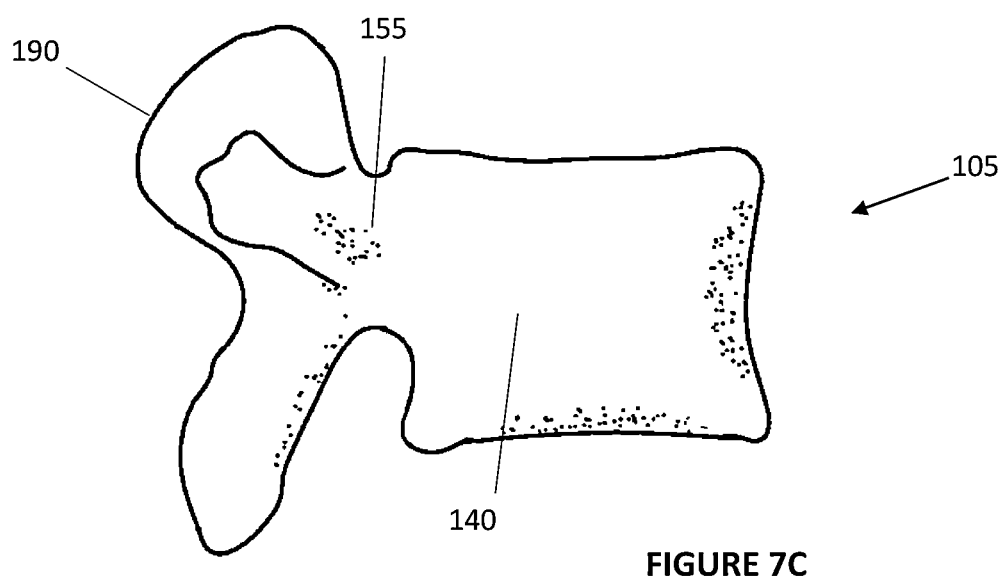
Figure 8:
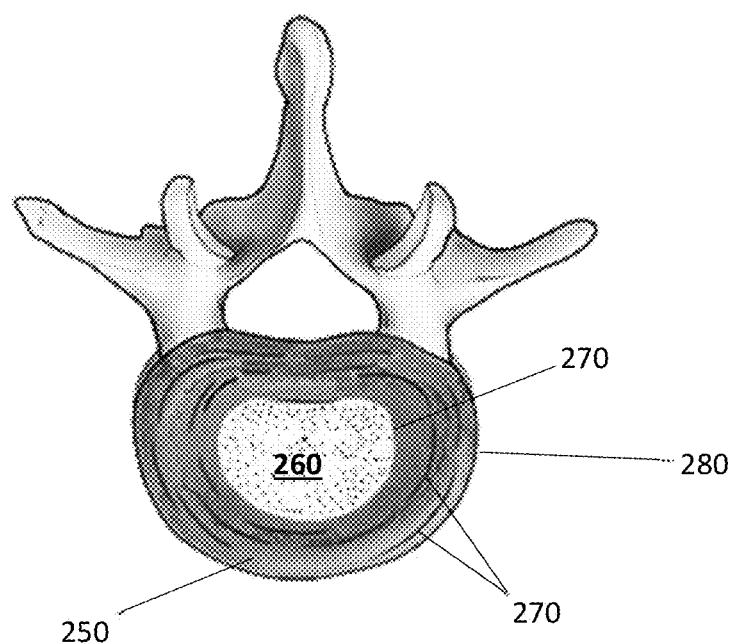
Figure 9:
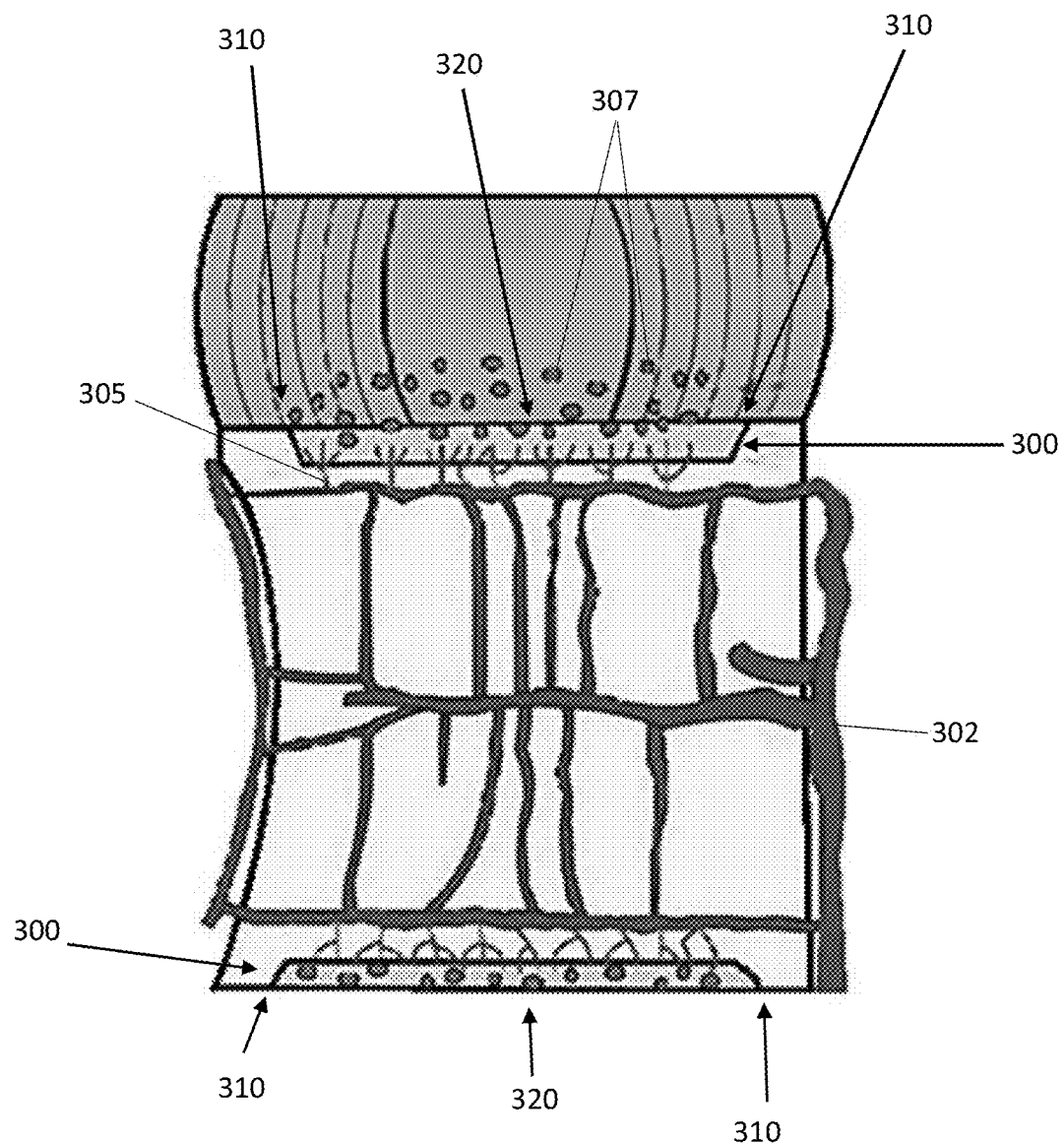
Figure 10:
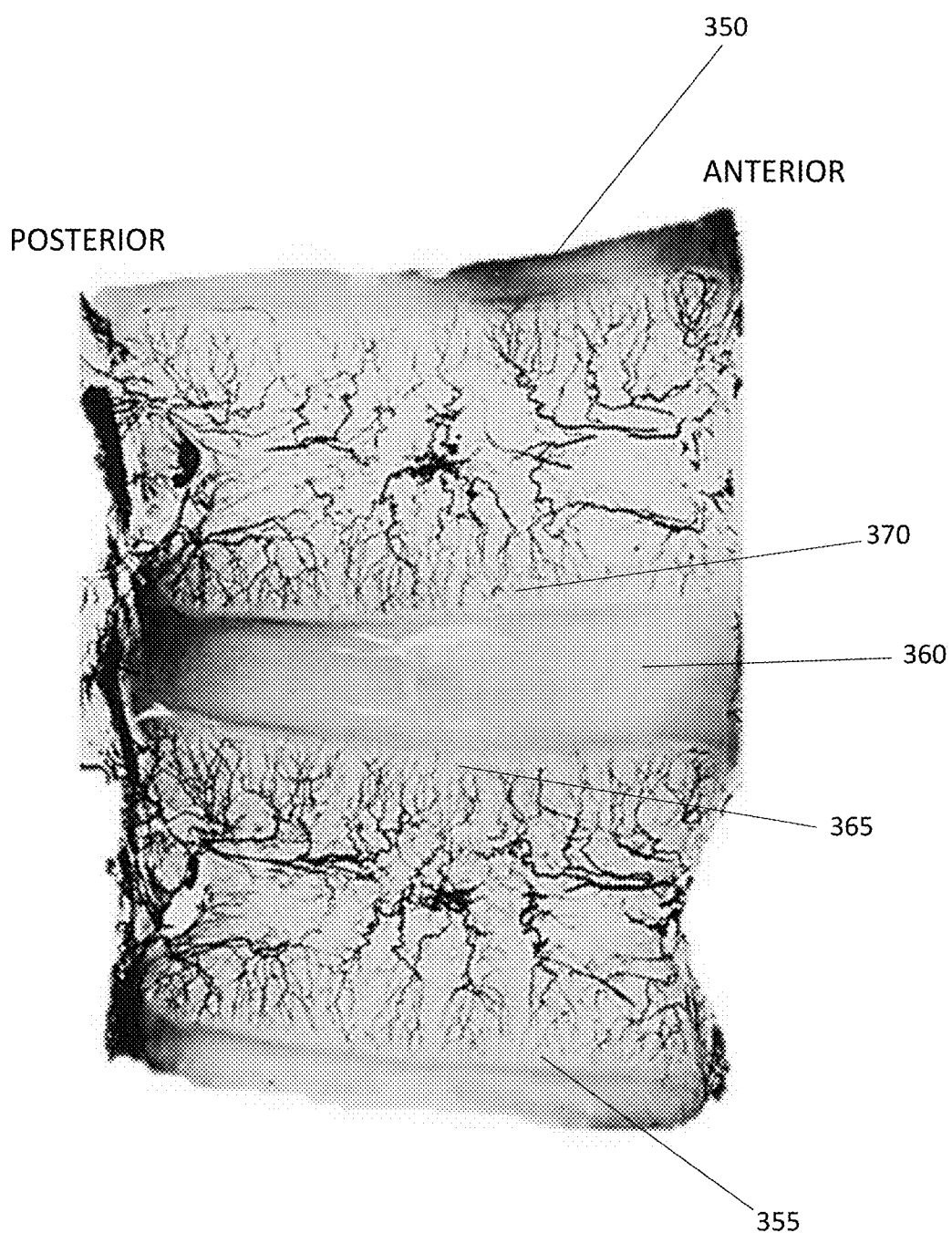
Figure 11A:
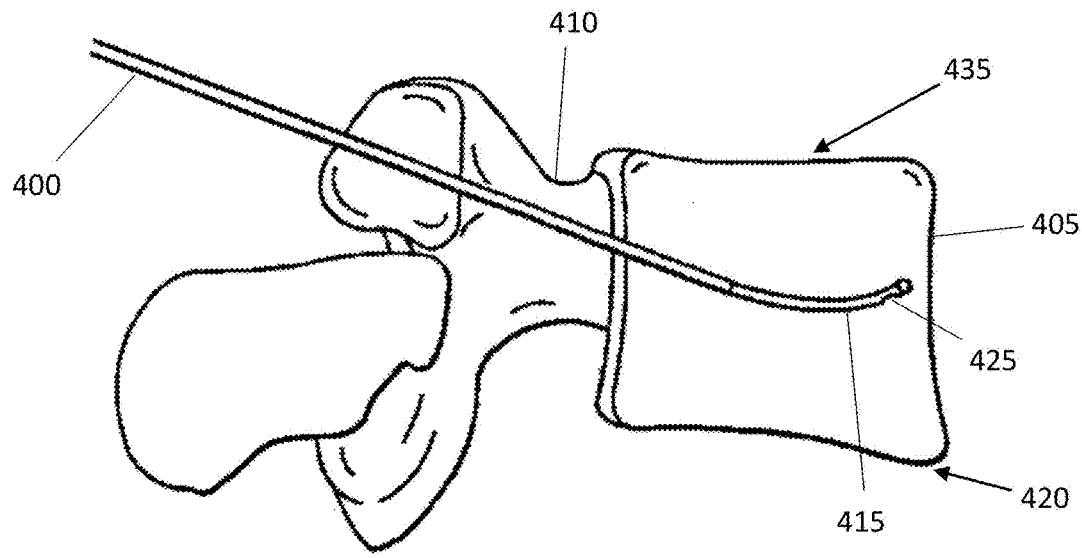
Figure 11B:
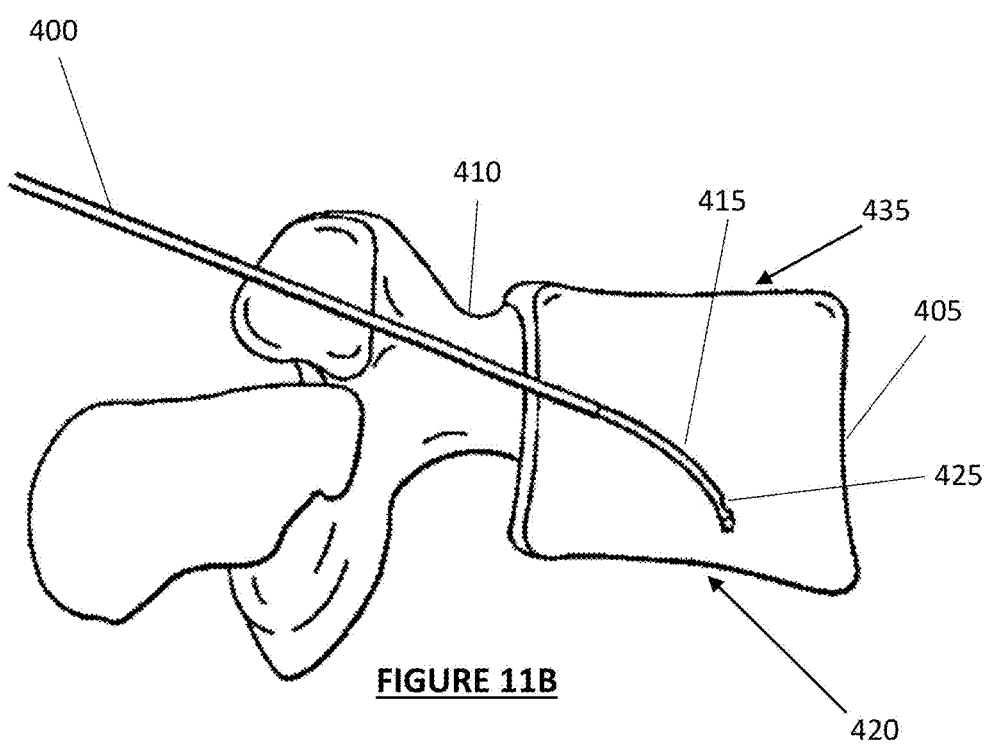
Figure 12:
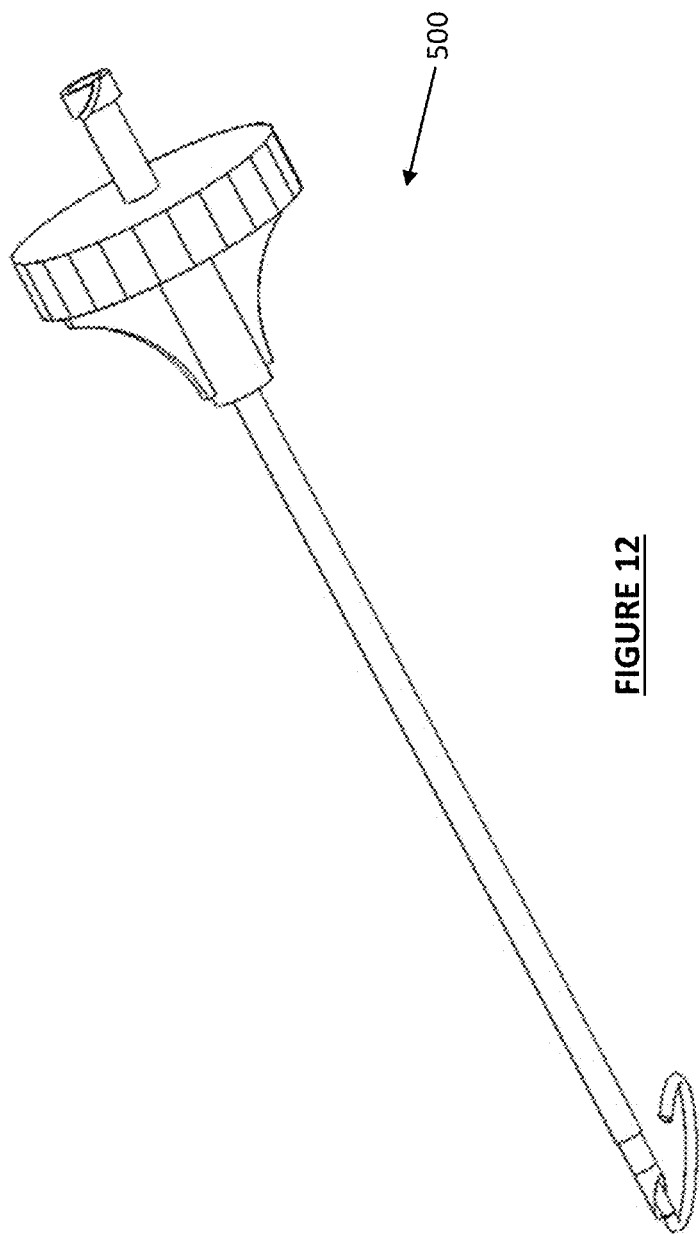
Figure 13:
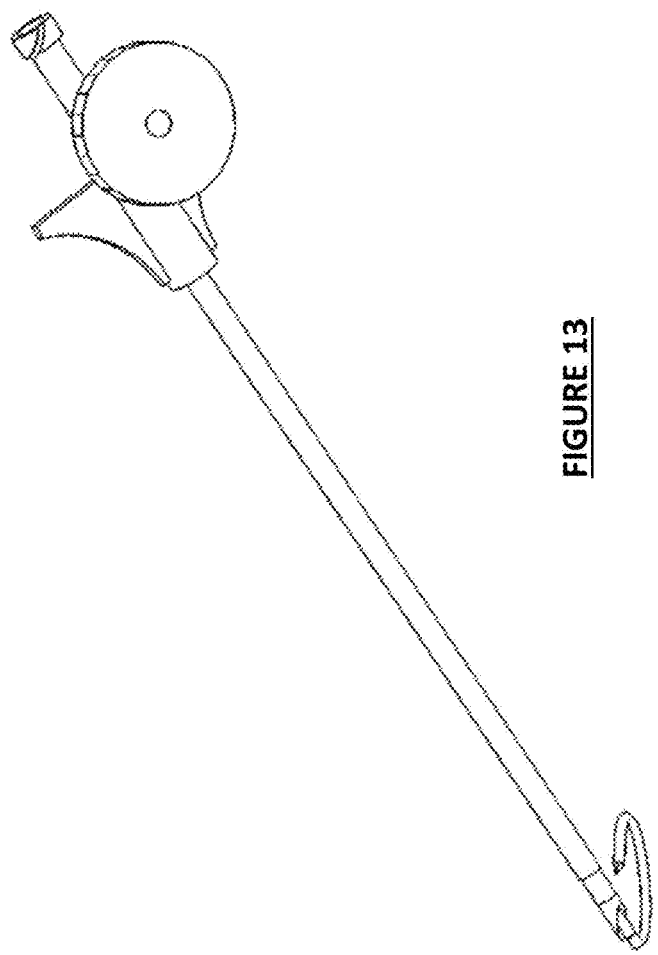
Figure 14:
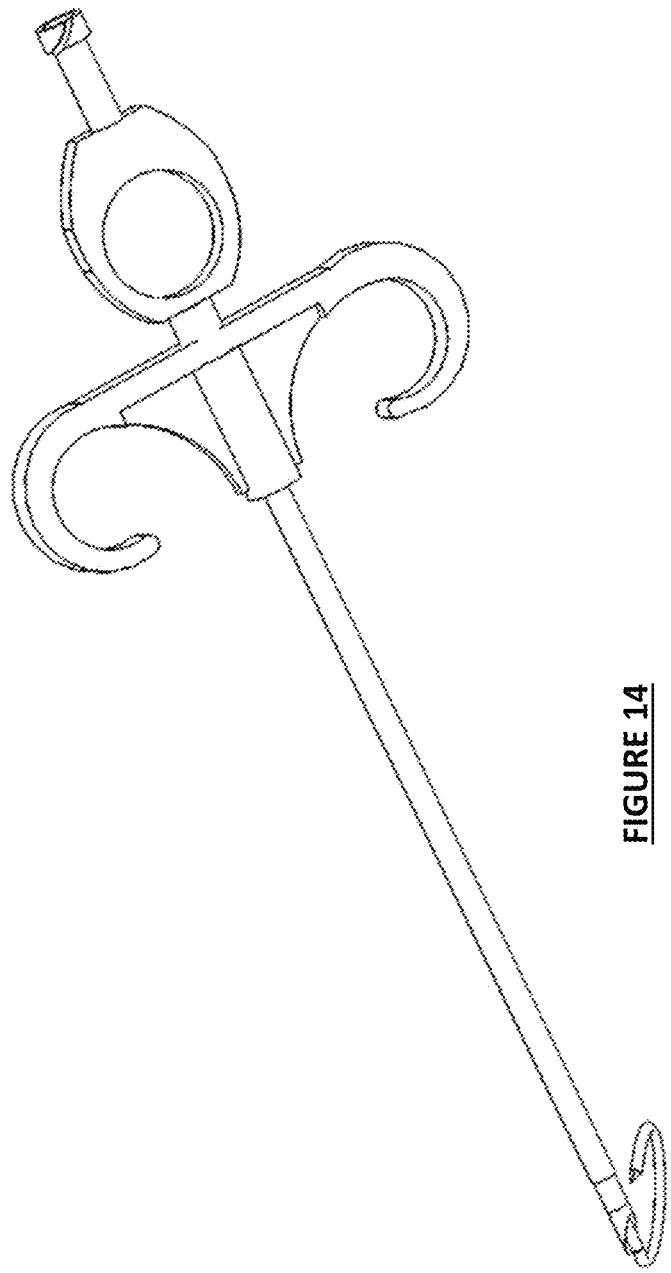
Figure 15:
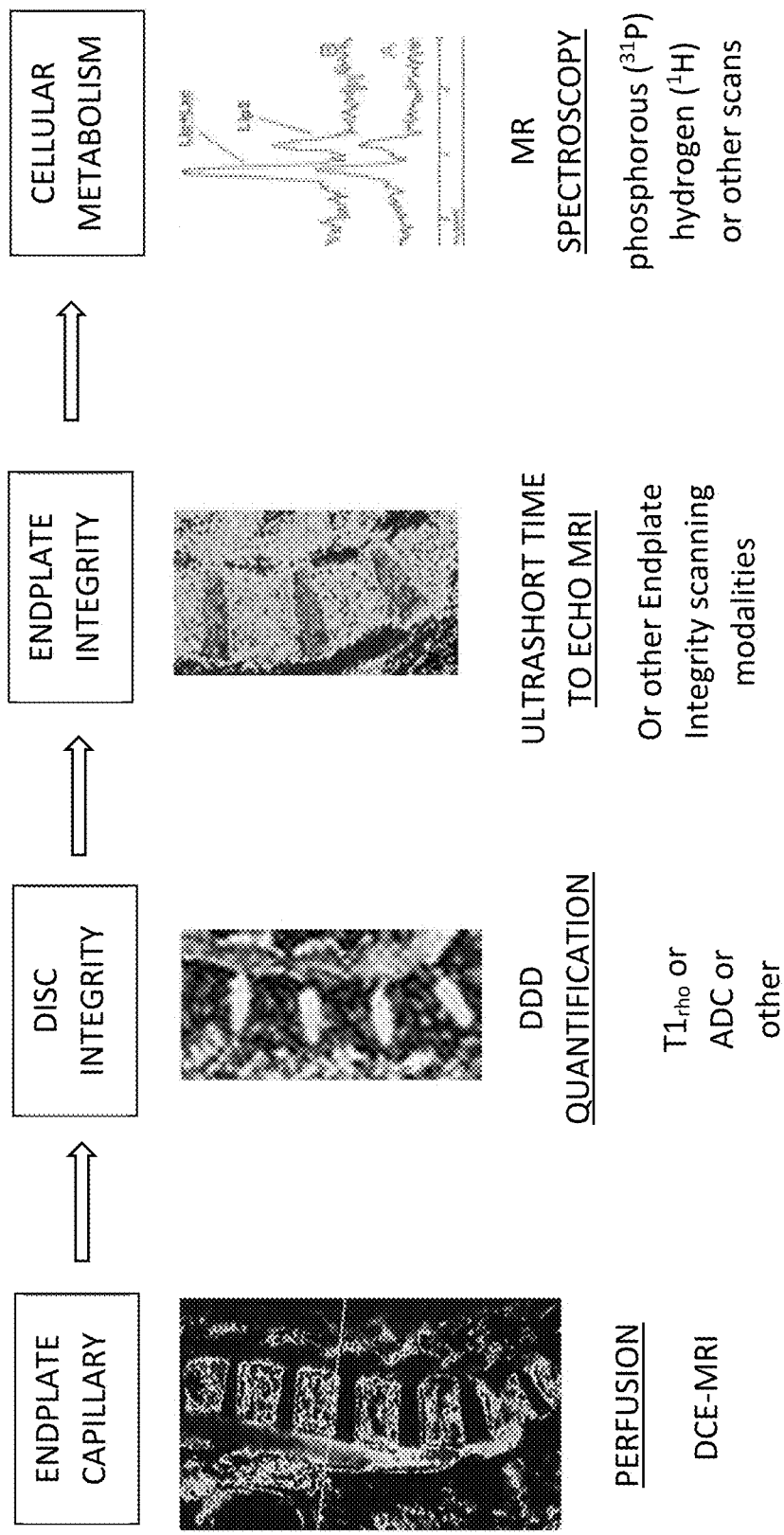
Figure 16:
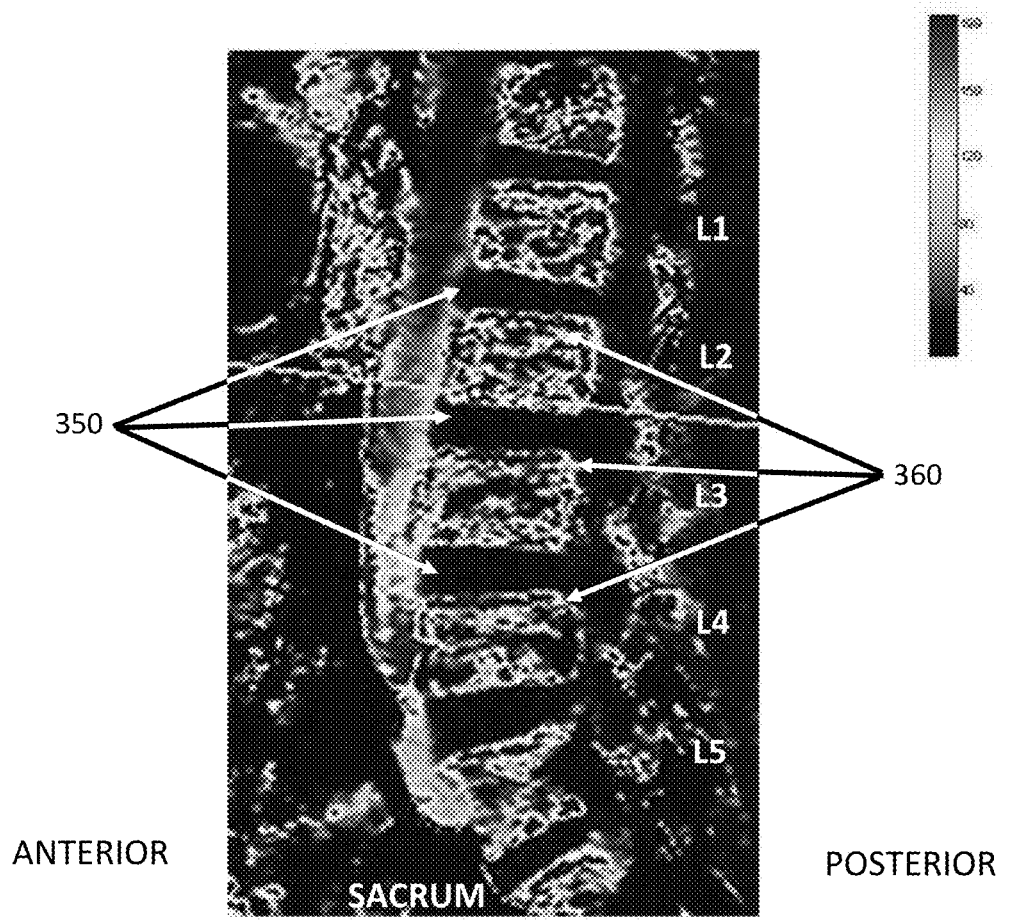
Figure 17:
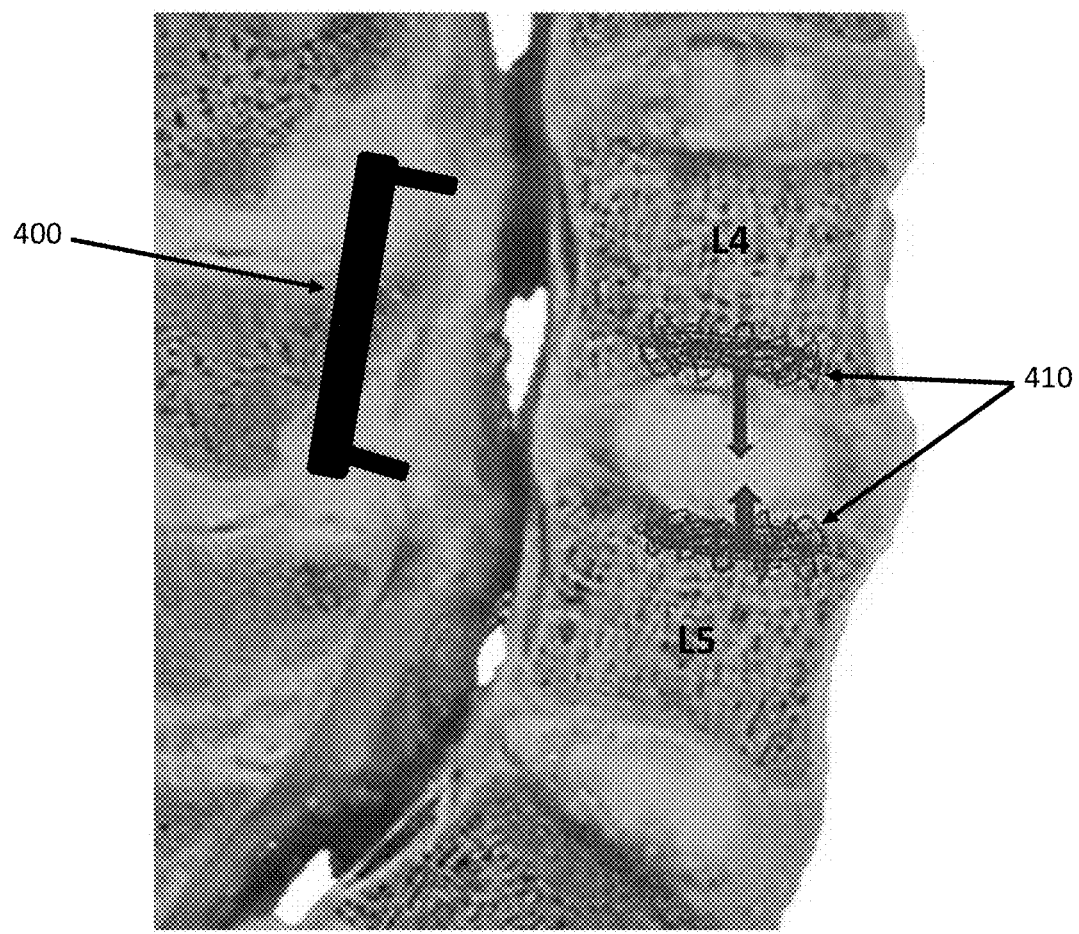
Figure 18:
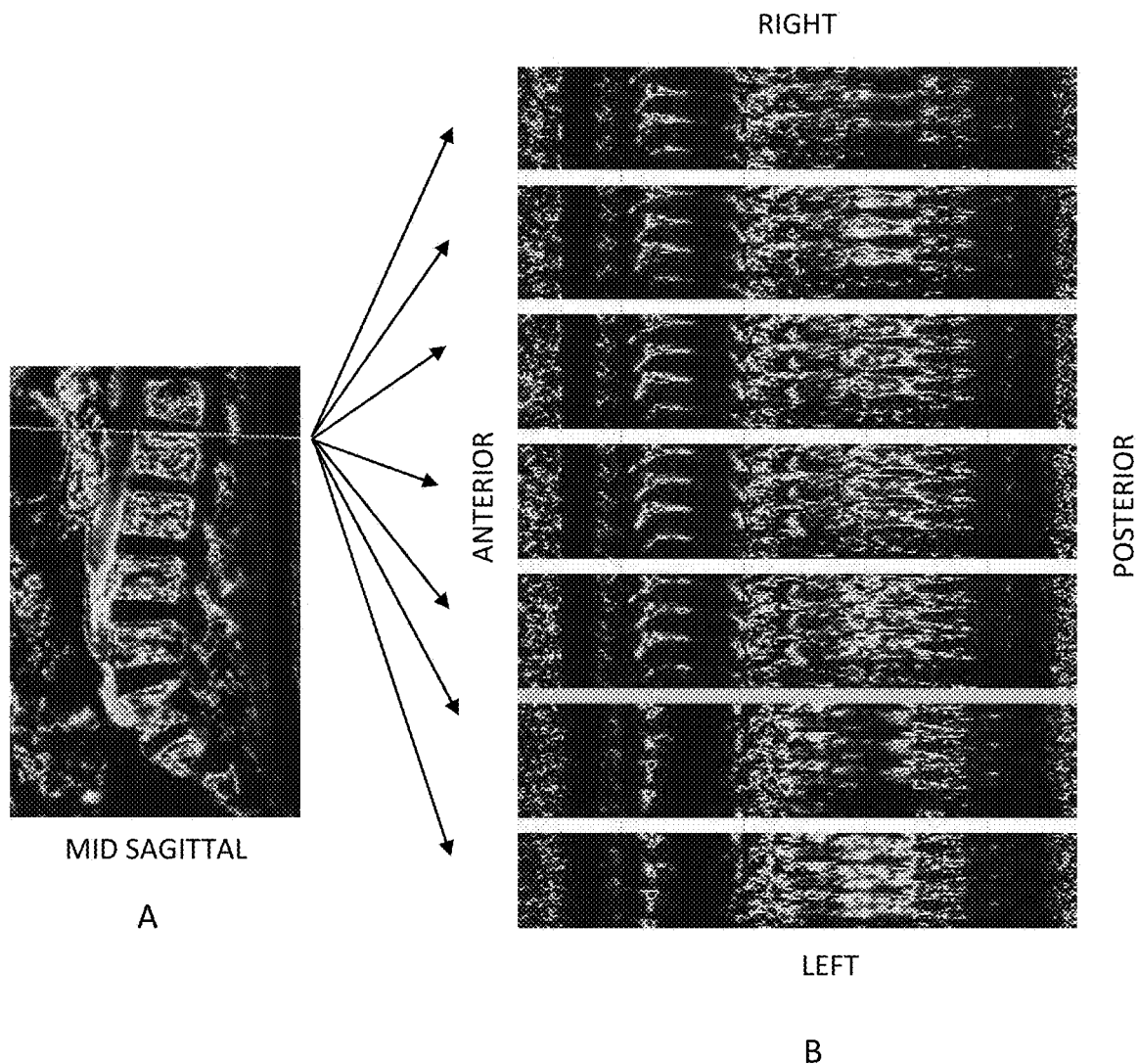
Figure 19:
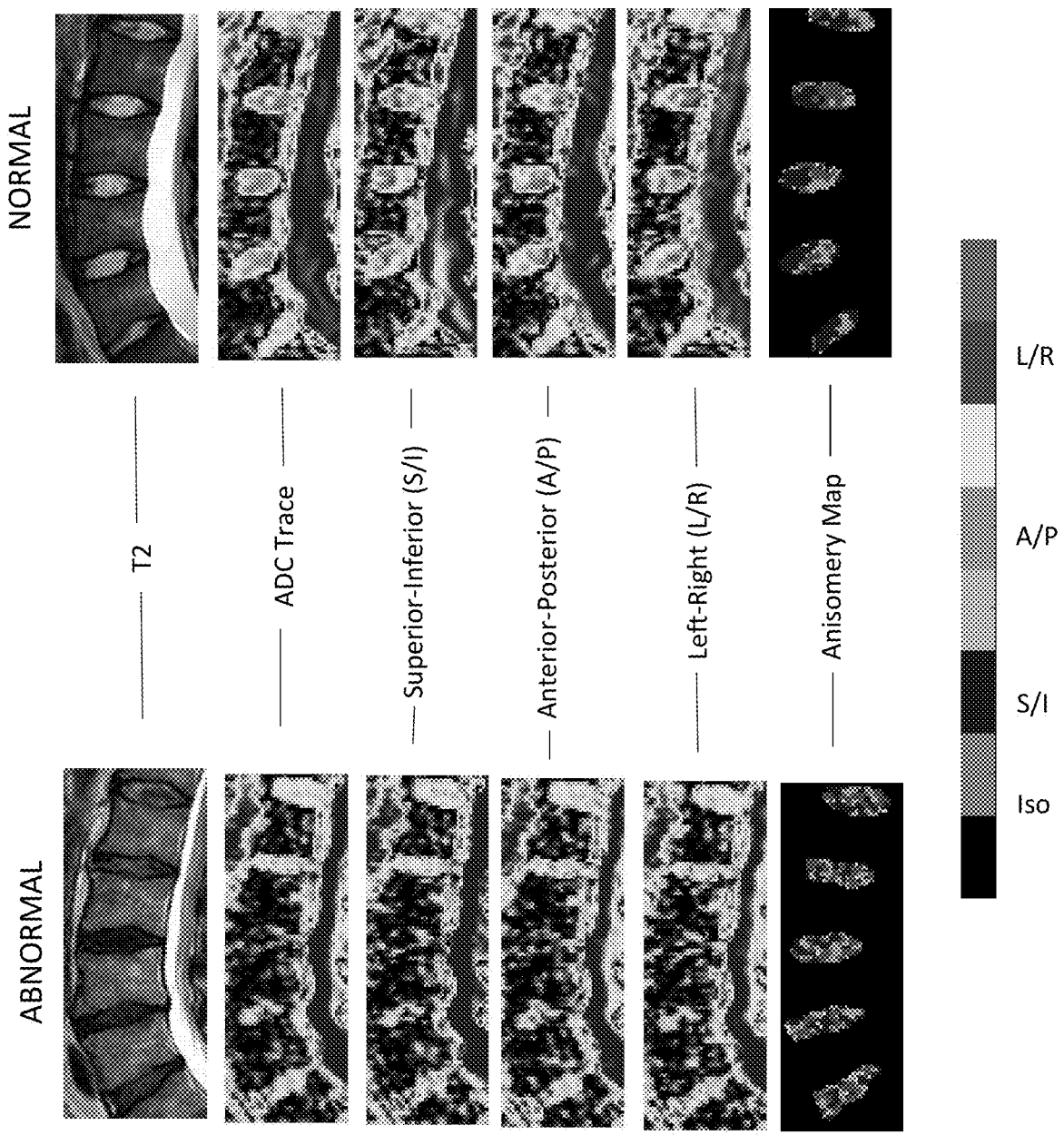
Figure 20A:
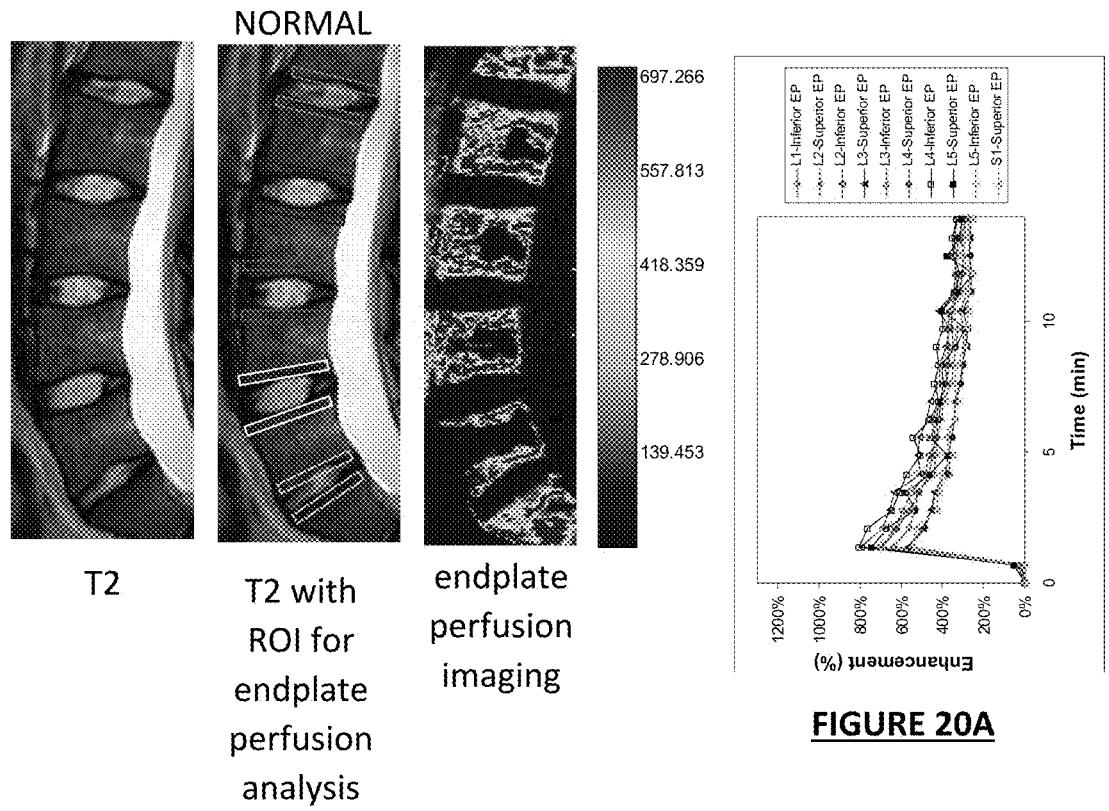
Figure 20B:
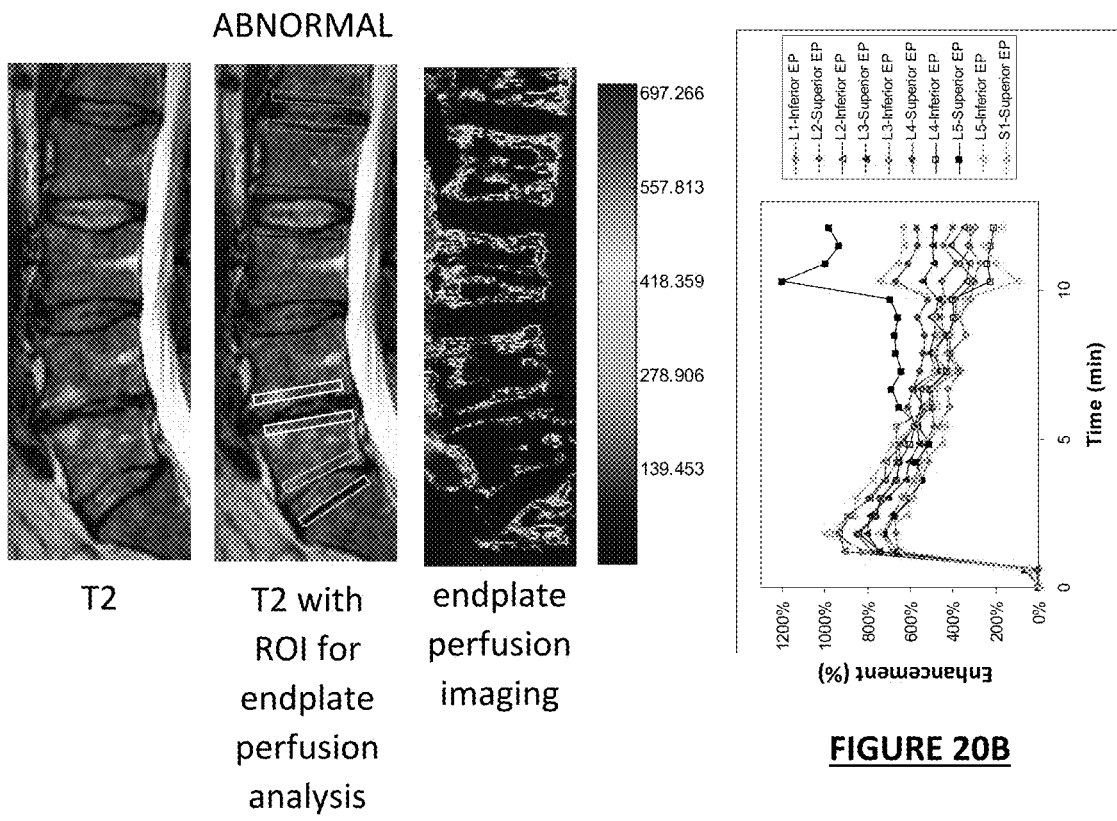
Figure 21A:
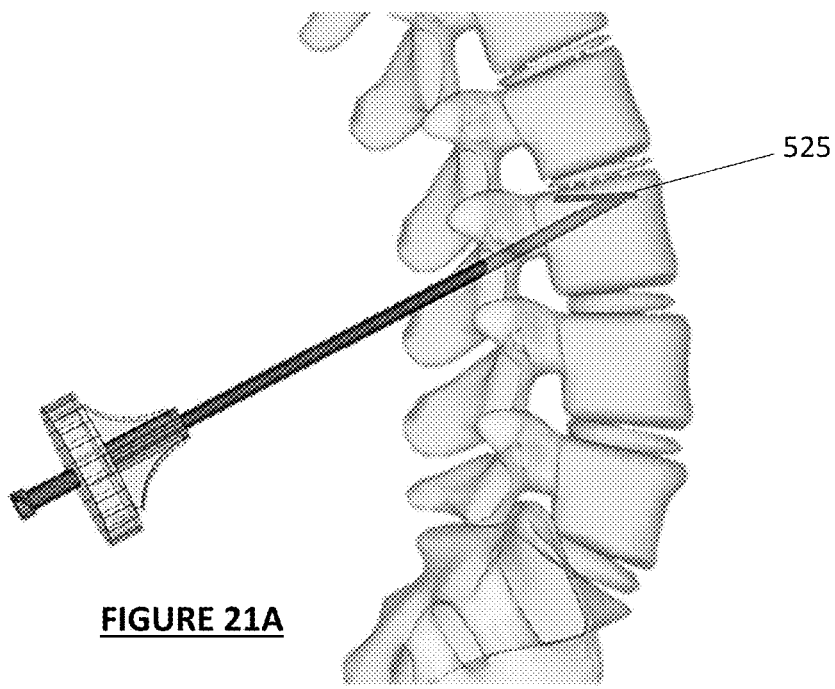
Figure 21B:
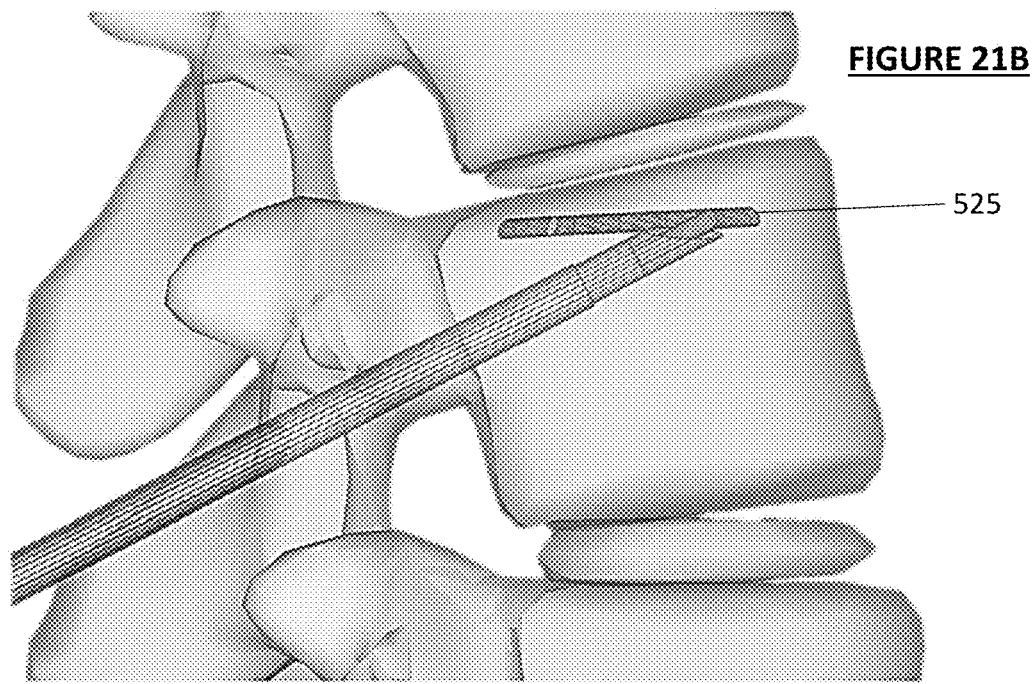
Figure 22A:
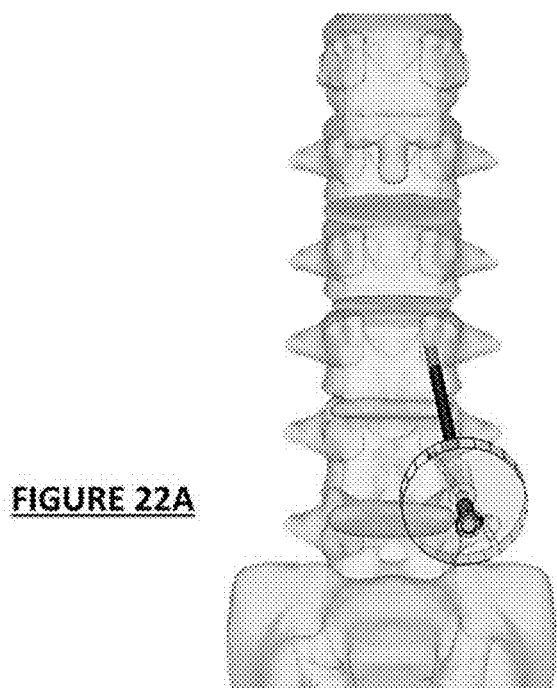
Figure 22B:
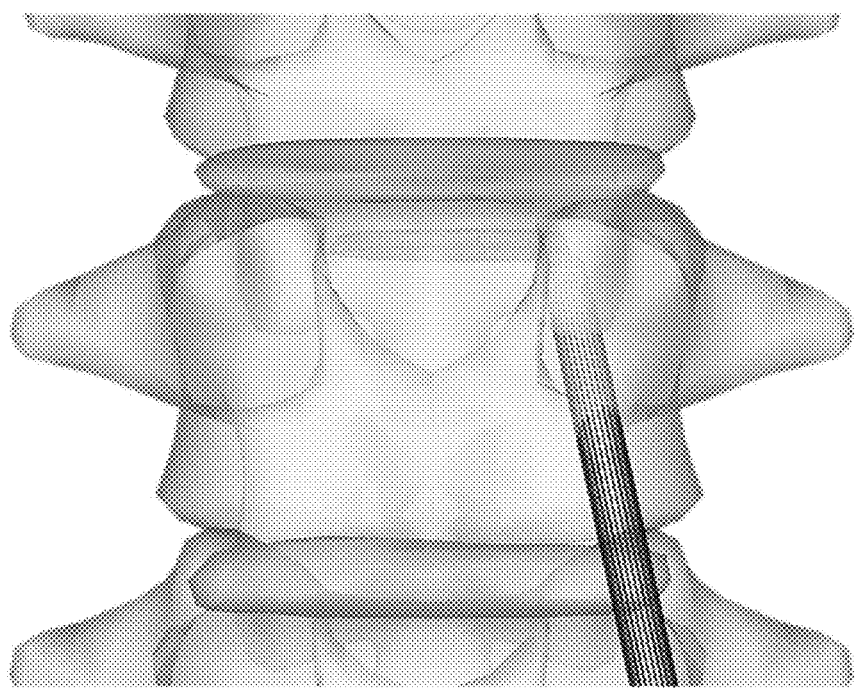
Figure 23A:
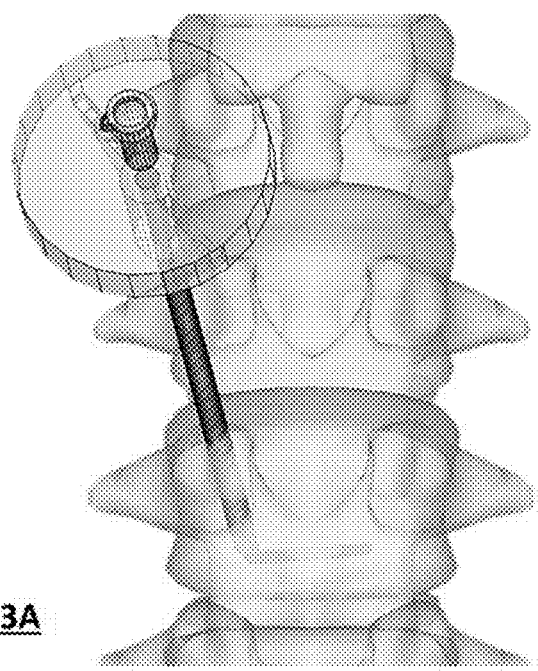
Figure 23B:
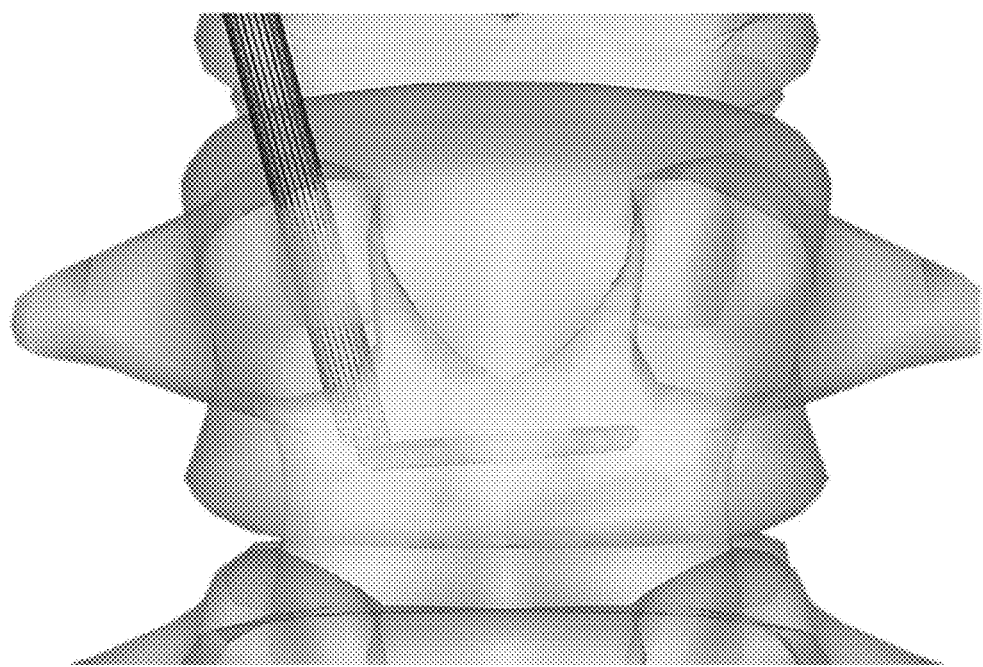
Figure 24A:
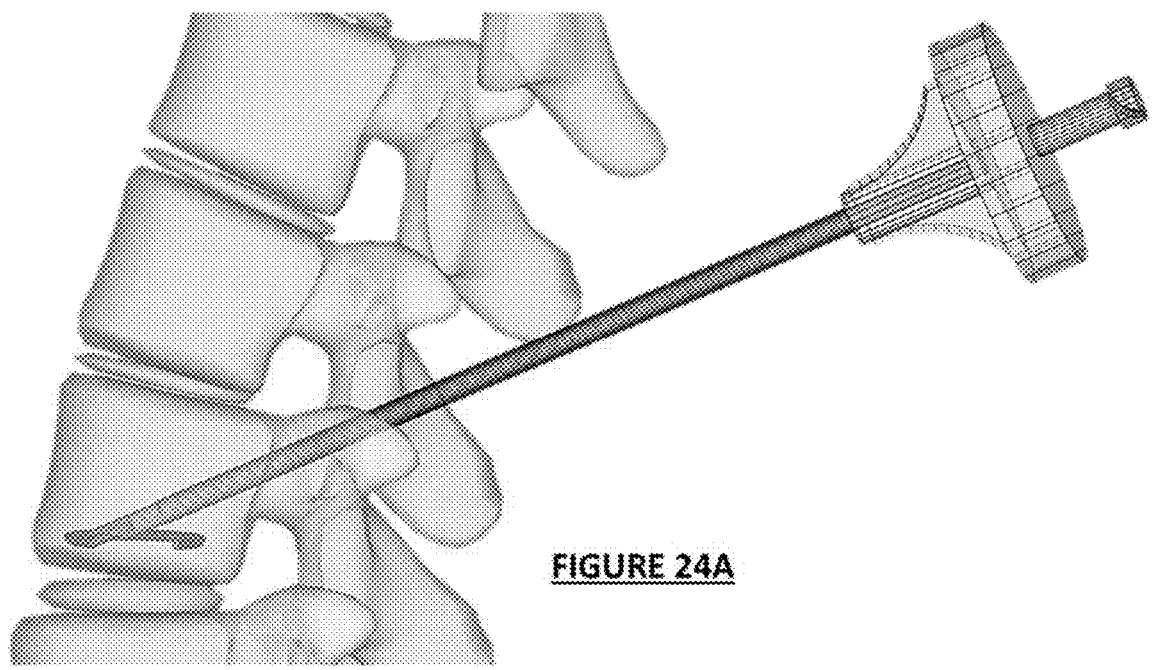
Figure 24B:
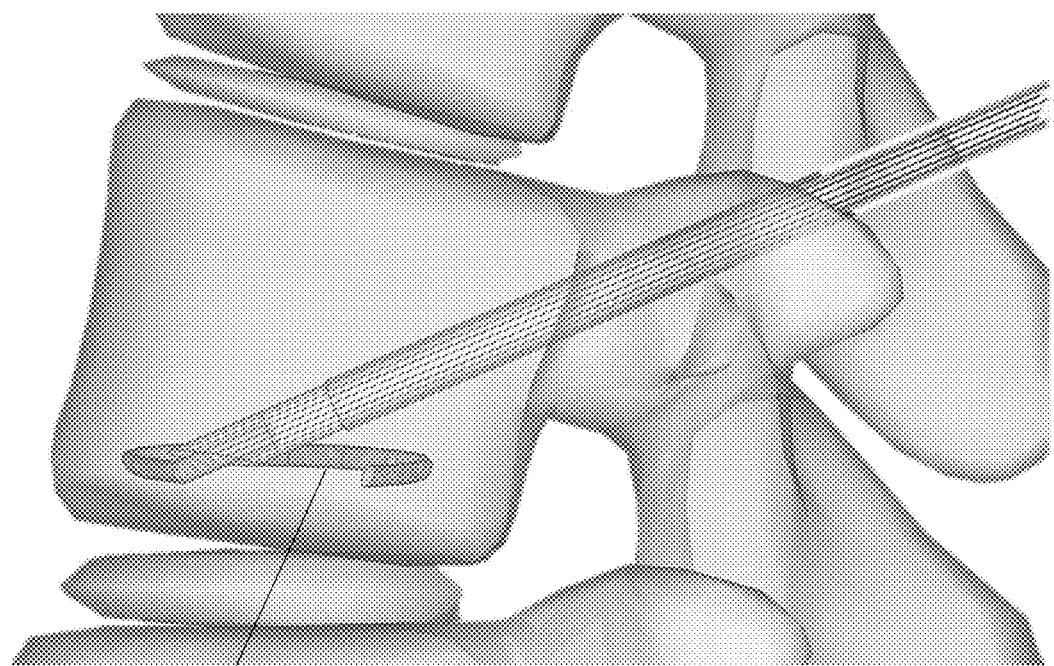

The accompanying drawings, which are included to provide a further understanding of the invention and are incorporated in and constitute a part of this specification, illustrate embodiments of the invention and together with the description serve to explain the principles of the invention:

FIG. 1 represents coronal MRA (magnetic resonance angiography) and T2 weighted sagittal MRI (magnetic resonance imaging) for a healthy control subject compared to 3 subjects (Sub1, Sub2, Sub3) with symptoms of chronic lower back pain and degenerative disc disease (DDD), along with a Max Intensity Projection (MIP) and Axial reconstruction for Sub3;

FIG. 2 shows data for subject 3 (sub3) of FIG. 1;

FIG. 3 shows data for the control of FIG. 1;

FIG. 4 shows a Max Intensity projection (MIP) (Panel A) and Axial reconstruction (Panel B) for sub3;

FIG. 5 shows MR (magnetic resonance) spectroscopy of the L4-5 disc (panel A) and of the L5-1 disc (panel B);

FIG. 6 shows the water-unsuppressed spectra of FIG. 5 (panel A) and the water-suppressed spectra of FIG. 5 (panel B);

FIG. 7A depicts a side plan view of an exemplary spinal motion segment. FIGS. 7B and 7C depict top and side plan views of one exemplary vertebral body;

FIG. 8 depicts a top view of an exemplary vertebral body and associated intervertebral disc;

FIG. 9 is a pictorial representation of a mid-coronal cross-section through a vertebral body and associated intervertebral disc;

FIG. 10 is a side plan view of an exemplary spinal motion segment showing exemplary intravertebral vasculature in vertebral bodies adjacent a disc;

FIGS. 11A and 11B are side views of a vertebrae and one embodiment of a spinal access and delivery device having a steerable tip;

FIG. 12 is a perspective view of another embodiment of a spinal access and delivery device;

FIG. 13 is a perspective view of another embodiment of a spinal access and delivery device;

FIG. 14 is a perspective view of another embodiment of a spinal access and delivery device;

FIG. 15 depicts a flowchart outlining one exemplary set of tests for use in diagnosing disc ischemia, with special notation of imaging the entire nutrient pathway to the disc;

FIG. 16 depicts an exemplary color map of a Dynamic Contrast Enhanced Magnetic Resonance Imaging (DCE-MRI) scan showing endplate capillary perfusion;

FIG. 17 depicts a pictorial representation of one exemplary embodiment of angiogenic treatment used in concert with spinal instrumentation;

FIG. 18 depicts an exemplary color map of a DCE-MRI scan performed with endplate perfusion mapping;

FIG. 19 is a series of exemplary images depicting diffusional differences between normal and abnormal discs;

FIGS. 20A and 20B depict exemplary imaging, region of interest (ROI) selection and analysis for normal and abnormal discs;

FIGS. 21A and 21B depict perspective views of one exemplary vertebral access and delivery system employing a lateral approach to a superior aspect of vertebral body;

FIGS. 22A and 22B depict perspective views of the vertebral access and delivery system of FIG. 21A employing an anterior/posterior approach to a superior aspect of a vertebral body;

FIGS. 23A and 23B depict perspective views of the vertebral access and delivery system of FIG. 21A employing an anterior/posterior approach to an inferior aspect of a vertebral body; and FIGS. 24A and 24B depict perspective views of the vertebral access and delivery system of FIG. 21A employing a lateral approach to an inferior aspect of a vertebral body.

DETAILED DESCRIPTION OF THE INVENTION

The following description is presented to enable any person skilled in the art to make and use the invention. Various modifications to the embodiments described will be readily apparent to those skilled in the art, and the generic principles defined herein can be applied to other embodiments and applications without departing from the spirit and scope of the present invention as defined by the appended claims. Thus, the present invention is not intended to be limited to the embodiments shown, but is to be accorded the widest scope consistent with the principles and features disclose herein. To the extent necessary to achieve a complete understanding of the invention disclosed, the specification and drawings of all issued patents, patent publications, and patent applications cited in this application are incorporated herein by reference. Although some embodiments are described below, these are merely representative and one of skill in the art will be able to extrapolate numerous other applications and derivations that are still within the scope of the invention disclosed.

Numerous studies suggested the notion that the vast majority of patients with long-term back pain, intractable by conventional approaches, have occluded lumbar/middle sacral arteries and that occlusion of these arteries is associated with disc degeneration. However, none of these studies proposed treatment methodologies, or placed it in the context of disease-specific diagnosis. These studies have included observations that patients with high LDL (low density lipoprotein) cholesterol complained of more severe back symptoms than those with normal value. These findings support previous studies that occlusion of lumbar/middle sacral arteries is associated with lower back pain and disc degeneration and that occlusion of these arteries may be due to atherosclerosis. Epidemiologic and post-mortem studies indicate that atheromatous lesions in the abdominal aorta may be related to disc degeneration and long-term back symptoms. However, these studies have not provided a means for classification of patients, or for therapeutic interventions. Additionally, since disc degeneration is not necessarily a painful process, the relevance of occluded spinal arteries remains enigmatic.

Various embodiments described herein include the realization that the health of avascular or partially-vascularized tissues may be dependent, at least in part, upon diffusive nutrient flow from and/or waste product flow towards adjacent vascularized regions. Where such adjacent vascularized regions may experience perfusion insufficiencies, the relevant diffusive flows may be partially or completely disrupted, which may result in tissue degradation of the adjacent avascular and/or partially-vascularized tissues. Desirably, where the perfusive insufficiency of the vascular region can be reversed or ameliorated as described herein, the diffusive nutrient/waste flow can be restored to some degree, which desirably results in slowing, halting and/or reversing of the tissue degradation process.

Embodiments described herein provide hypoxic and/or ischemic disc disease as a defined disease subset, in which patients may be specifically classified that are amenable to treatment with treatments capable of stimulating perfusion and/or preventing or slowing further vascular degeneration. Specifically, in one embodiment, hypoxic and/or ischemic disc disease is diagnosed as stenosis or the complete occlusion of one or more blood vessels associated with the lumbar area.

The importance of perfusion is seen in the following discussion regarding lumbar vasculature. It is known that the blood supply of the lumbar spine is derived from the aorta through the lumbar and middle sacral arteries. The upper four segments of the lumbar spine receive their blood supply from the four pairs of the lumbar arteries, which arise in the posterior wall of the abdominal aorta. The fifth lumbar segment is supplied partly by the middle sacral artery (arising in the bifurcation) and partly by branches of the iliolumbar arteries (arising from the internal iliac arteries). Nutrition of the avascular intervertebral disc occurs by diffusion through the vertebral endplates from the blood vessels in the vertebral bodies above and below the disc. Cholesterol plaques in the wall of the aorta obliterate orifices of lumbar and middle sacral arteries and decrease blood supply of the lumbar spine and its surrounding structures. As a result, structures with precarious nutrient supply, such as the intervertebral discs, gradually degenerate. Reduced blood flow causes hypoxia and tissue dysfunction. It also hampers removal of waste products, such as lactic acid. These changes are found by the current invention to mean that in some patients irritation of nociceptive nerve endings occurs, causing pain, as well as lead to deterioration and atrophy of the structures involved. Accordingly, the invention provides not only means of quantifying and relating hypoperfusion with pathological and symptomatic features, but also methods of selecting patients that would benefit from interventions aimed at stimulating perfusion in the area of the spine, or areas associated with not only lack of blood supply but also removal of metabolic wastes.

Because the intervertebral disc is typically a poorly vascularized or avascular structure, the nutrients required to maintain cellular function and viability, primarily glucose and oxygen, are supplied to the disc by capillary vessels and microvasculature in the vertebral body structures proximate to the intervertebral disc endplates. In addition, waste products such as lactate are removed. Once glucose and oxygen leave the capillaries, passive diffusion becomes the mechanism of nutrient transport through the endplate and matrix. The transport distance of the disc is typically greater than any tissue in the human body (which can be up to 8 mm or more for the chondrocytes in the middle of the disc). A large concentration gradient is often required for optimal diffusion. The concentration gradient is determined by the utilization of the nutrients by the viable chondrocyte population within the disc and the concentration of nutrients delivered to the endplate by the microcirculation. Thus, any decrease in the population of functional endplate capillaries has the potential to create metabolic derangement within the disc, leading to degeneration and discogenic pain.

Glucose and oxygen are extremely important to the function and viability of the chondrocytes. Experimental measurements can demonstrate that oxygen concentrations can be very low in the nucleus and increase towards the disc surface, and a detected lactic acid concentration showed the reverse profile. The lactate levels can potentially increase due to increased glycolytic by-products and poor circulatory removal. Since lactic acid is not only the major waste of disc cells but also an acid, its accumulation results in a lowered pH inside the disc. In vitro experiments have shown that low oxygen concentrations and acidic pH significantly affects synthetic activity (especially proteoglycan synthesis rates of disc cells) leading to a fall in proteoglycan content and therefore to disc degeneration in vivo. In addition, extremely low pH and glucose concentrations due to a harsh, anaerobic environment can quickly lead to cell death. The interrelationships of these nutrients and metabolites are complex. It appears that disc cells may be protected from a low pH and glucose by a hypoxic environment. The provision of glucose and removal of lactate (to keep the pH from dropping too low) may be a necessity for chondrocyte survival. However, oxygen is required for metabolic needs beyond subsistence, such as protein synthesis. Given all of the complex interactions of the nutrients and metabolic byproducts, cellular needs can be difficult to predict, especially taking into account the cells' constantly changing metabolic demands. Regardless of the complex interactions taking place in the degenerating disc, however, the fact remains that both the supply of nutrients and removal of waste require an intact endplate capillary network.

Anatomical Imaging of Structural Features

The various concepts described herein include the use of image data obtained of a patient's anatomy, which can include non-invasive and/or limited-invasive (i.e., contrast enhanced and/or minimally-invasive) sources of image data of the patient. The various embodiments and concepts disclosed herein also contemplate the use of technologically improved software and/or imaging hardware and systems that can provide high-quality images without the use of contrast injections and/or other exogenous agents, including those developed in the future. In various embodiments, the efficient detection, analysis and diagnosis of ischemic disc disease, ischemic spine disease, diffusive insufficiency and/or other tissue pathologies will typically be dependent upon the quality and resolution of image data acquired of the patient's anatomy. Where the diagnosis is focused on nutrition to an individual intervertebral disc, the relevant patient image data will desirably include anatomical image data of the patient's vertebral bodies immediately above and/or below the intervertebral disc, as well as the disc structure itself and any surrounding anatomy, as desired.

A unique challenge posed by various embodiments described herein can relate to unique anatomical features of the particular anatomy of interest. Unlike typical anatomical imaging studies, various regions of interest particularly relevant to the present invention can include image data of vasculature and other anatomical structures located inside of the patient's bones (i.e., vertebral bodies or other bony structures). Unlike the imaging of soft tissues and the outer surfaces of skeletal structures, the differentiation of vasculature within skeletal structures can be particularly challenging. Similar issues can be encounter with imaging of fluid and blood flows within bones. Moreover, particular locations within a given bony structure may be difficult to image, owing at least in part to the density and orientation of relevant and/or adjacent structures.

In an initial step, anatomical image data is obtained of an individual patient's anatomy. This image data can be derive from a wide variety of sources, including MRA (magnetic resonance angiography), MRI (magnetic resonance imaging), x-ray imaging, cone beam CT, digital tomosynthesis, and ultrasound, CT scans or PET or SPECT scans. Desirably, image data is obtained that includes the patient's biological structure(s) of interest, which in one exemplary embodiment includes anatomical structures of vertebrae proximate to a patient's intervertebral disc. For example, pixel or voxel data from one or more radiographic or tomographic images of the patient's anatomy can be obtained using magnetic resonance angiography. Other imaging modalities known in the art such as MRI, ultrasound, laser imaging, PET, SPECT, radiography including digital radiography, digital tomosynthesis or cone beam CT can be used. Contrast enhanced imaging can be employed, if desired.

Desirably, one or more of the pixels or voxels of the image data are converted into one or a set of values. For example, a single pixel/voxel or a group of pixel/voxels can be converted to coordinate values, such as a point in a 2-D or 3-D coordinate system. The set of values could also include values corresponding to the pixel/voxel intensity or relative grayscale color. Moreover, the set of values could include information about neighboring pixels or voxels, such as information that corresponds to a relative intensity or grayscale color and or information corresponding to a relative position.

The image data can be segmented, partitioned or otherwise altered into multiple segments or superpixels. The goal of segmentation is to simplify and change the representation of an image into something that is more meaningful and easy to identify. Image segmentation can be used to locate features and boundaries, such as data corresponding to a particular biological feature of interest. For example, the image data can be used to identify edges of structural features of the spinal anatomy, such as surface outlines of a vertebral body or endplate. In various imaging systems, a distinctive transition in color intensity or grayscale at a structure's surface can be used to identify pixels, voxels, corresponding data points, a continuous line, and/or surface data representing the surface of the biological structure. These steps can be performed automatically (for example, by a computer program operator function) or manually (for example, by a clinician or technician), or by various combinations of the two.

If desired, segmented data can be combined, such as in a single image including selected segmented and/or identified reference points (e.g., derived from pixels or voxels) and/or other data that can be combined to create a line representing a surface outline of a biological structure. In various embodiments, segmented and/or selected data from multiple 2D image slices can be combined to create a 3D representation of the biological structure. Depending upon the in-plane resolution and slice thickness (which can together define a voxel size, if desired), the field of view, the matrix size and the slice gap, the images can be combined to form a 3D data set, from which the 3D representation of the biological structure can be obtained. In various embodiments, a computer program could be used to load and view 2D images or 3D images could view multiple 2D images as one or more views of 3D image stacks. A series of image slices along one axis and a series of image slices along a second, non-parallel axis could be viewed as separate stacks of 2D images. Stacks of images could result from separate image scans (which can include the use of a single imaging modality along multiple reference planes as well as the sequential imaging of anatomy of interest using different imaging modalities along the same or different planes for each modality) or could be differing views or viewpoints of the same scan. In addition, any two or more images could be combined to provide a 3D image or image approximation.

In various embodiments, the 3D structure of an anatomical feature can be derived directly using a 3D segmentation technique, for example an active surface or active shape model algorithm or other model based or surface fitting algorithm. Alternatively, a 3D representation of the biological structure could be generated or manipulated (i.e., corrected or smoothed) by employing a 3D polygon surface, a subdivision surface or a parametric surface such as a non-uniform rational B-spline surface. Various methods are available for creating a parametric surface, which can include converting the 3D representation directly into a parametric surface by connecting data points to create a surface of polygons and applying rules for polygon curvatures, surface curvatures, and other features.

In one alternative embodiment, a template model could be applied to approximate and identify a biological feature or could be applied directly to an image data array. For example, a vertebral body template could be applied to an image data file and/or subsequently segmented image data. In applying a template model, the operator, user or the software itself could select one or more initial best fit template models. Template models of relevant anatomical structural features can be obtained from a library of models or other publicly available sources.

Obtained anatomical image data can include points, surfaces, landmarks and/or other features, which can collectively be referred to as "reference points." In certain embodiments, the reference points can be selected and/or identified by an automated program or manually by an operator and used to identify an anatomical feature and/or region of interest. For example, reference points from an anatomical image of the spine can be used to identify particular anatomical features of the spine, such as the vertebral bodies, pedicles, spinous process, aorta, spinal cord, vertebral arch, intervertebral discs and endplate structures, which in turn can be used to identify one or more specific regions of interest of the image data for further analysis. If desired, reference points can be grouped to form reference structures and/or surfaces, including triangles, polygons, or more complex surfaces such as parametric or subdivision surfaces.

Once the appropriate spinal anatomy is identified, one or more regions of interest in the image data will desirably be identified. For example, if a vertebral body and endplate structure can be identified from the segmented data, the relative location of a relevant subchondral capillary bed and/or associated/relevant microcirculation within the vertebral body proximate to the endplate can be identified and assigned or "bounded" as one or more regions of interest (ROI) of the image data. This ROI can be analyzed in a variety of ways, and the analysis results can be compared to a defined value and/or standard (and/or can be displayed and/or assessed using a value "map" of RI(s) in 2D or 3D space) and utilized to diagnose, assess and/or quantify pathology. If desired, the analysis and diagnosis can be used as guidance for treating the patient.

Vascular, Perfusion and Diffusion Imaging

In various embodiments of the invention, diffusion studies (Diffusion Weighted images or DWI) can be performed for analyzing the diffusion characteristics of the disc and correlating it to vascular hypoperfusion, disc degeneration and/or segmental artery stenosis. In other embodiments, perfusion studies can be performed using methods such as Dynamic Contrast Enhanced MR Imaging for analysis of perfusion of the vertebral bodies.

Diffusion and Other Studies

Diffusion Weighted Images (DWI) can help delineate benign and malignant vertebral collapse fractures, and may also be useful to some degree in analyzing the diffusion characteristics of the normal disc and correlating it with disc degeneration and segmental artery stenosis and/or vertebral body perfusion abnormalities. Solute transfer into the central portion of the disc (nucleus) can be dependent upon the concentration of the solute at the vertebral endplate (correlated with vascular perfusion) and the diffusion characteristics of the disc. Abnormalities in diffusion contribute to disc degeneration. Analyzing diffusion properties among various patient populations (as well as normal controls) may lead to data that can contribute to the ischemic disc disease diagnosis.

DCE-MRI and Other Techniques

Dynamic Contrast Enhanced MR Imaging for analysis of Perfusion of the vertebral bodies can include using a 1.5 Tesla scanner to evaluate a potential for ischemia-related osteoporosis. However, higher powered imaging equipment, such as 3 Tesla or higher scanners, may significantly improve the accuracy and resolution of image data, which can be particularly useful in imaging and assessing the intravertebral microcirculation proximate the intervertebral disc endplates. In one exemplary embodiment, imaging parameters for a 3 Tesla scanner have been developed to facilitate the acquisition of such useful image data. Other systems could be used, if desired, including those that employ the use of high-field magnets due to their higher SNR (signal to noise) and CNR (contrast to noise) ratios in comparison to lower strength magnets. Such systems could potentially allow a lower dose of contrast material to be delivered to the patient yet allow generation of an equivalent image quality to those of lower-field magnets with a higher dose of contrast. Such a system may also permit the use of serial (multiple) bolus contrast injection for multiple scanning sequences of the patient, potentially using different scanning techniques and/or modalities. The use of higher strength systems, including those with 7-10 Tesla magnets, may improve the resolution and accuracy of scanning, including the potential to directly image the microvasculature and/or vascular buds. If different imaging techniques are to be employed, it may be desirous to complete any non-contrast imaging initially, and then subsequently perform contrast-assisted imaging, to reduce the potential for imaging errors and/or artifacts caused by the contrast and/or its remnants during the non-contrast imaging techniques.

For imaging protocols in one exemplary embodiment, the following could be used in conjunction with a Philips Achieva 3T system: 330 mm×300 mm FOV and a 6-element SENSE torso RF coil. The imaging session started with the perfusion scan following the standard calibration scans. A 3D FFE sequence with TR/TE=3.5 ms/1.5 ms, SENSE factor: 2.5(AP), 2(RL), flip angle=30°, with dynamic scan time of 2.9 s was used and 7 slices in sagittal orientation with 6 mm thickness and 1.9 mm×1.9 mm pixel size were acquired. A total of 114 volumes were collected, 2 of them before contrast injection. After the dynamic scans, T1 weighted anatomical images in sagittal plane were collected using a TSE sequence with 0.5×0.5×3 $mm^3$ voxel size. 14 slices cover the same volume as dynamic scans. TR/TE=900 ms/10 ms, flip angle=90°. This was followed by a T2 weighted scan that had identical geometry to T1 scans and TR/TE=2940 ms/120 ms, flip angle=90°. Finally, contrast-enhanced angiography scans were collected. Contrast bolus arrival was observed real-time using a single, 50 mm thick coronal slice using FFE sequence in dynamic mode, collecting images every 0.5 s. Once the contrast arrived in the descending aorta, actual 3D angiography scan was started by the operator immediately. TR/TE=5.1 ms/1.78 ms, voxel size=0.8*0.8*1.5 mm$^3$, with SENSE factor=4 was used to acquire 50 coronal slices. Segmental vessels on MRA were graded as occluded, stenotic or open. Discs were graded as per Pfirrmann (Pfirrmann, C. et al, *Spine* 26:1873-1878, 2001). ROI-averaged time course (from whole vertebra and/or end-plate) was converted into a fractional enhancement time course and analyzed using a compartmental model (Larsson, et. al. *MRM* 35:716-726, 1996; Workie, et. al. *MRI*, 1201-1210, 2004). The model fitting results in 6 parameters: Ktrans' (apparent volume transfer constant), kep (rate constant), Vp' (apparent fractional plasma volume), E (extraction fraction), tlag (arrival time of tracer in the ROI) and baseline.

In one alternative exemplary embodiment, a high spatial resolution version of DCE-MRI could include a 3D gradient echo-based sequence with TR/TE=3.4/1.2 (ms), flip-angle=30 (degree), reconstructed voxel-size=0.8×0.8×3 (mm), temporal-resolution (or dynamic scan time)=36.4 (sec) w/22 dynamic frames (volumes). The entire bolus of contrast could be utilized for the DCE-MRI, which was preferable for this embodiment, or the contrast can be given in two boluses, one for DCE-MRI and one for MRA. Other non-contrast scans (i.e., T1 and T2w) could employ the same or similar acquisition parameters as described above, with non-contrast imaging desirably preceding contrast-assisted imaging where possible.

Data can be collected from control and experimental subjects to ascertain an "ischemic index" of the vertebral bodies, which could desirably be applied to future assessments of ischemic/hypoxic disc disease. The data can be correlated with the degree of disc degeneration and the degree of segmental artery stenosis to define a new clinical entity and the proper imaging tools for diagnosis of spinal, particularly lumbar, ischemia. Since perfusion analysis can potentially measure the amount of blood supply coursing through the vertebral bodies and microvasculature thereof, and therefore the amount of nutrition available for the disc, this value can be important in developing treatment schemes based on improving the blood supply to the vertebrae (and therefore, the disc).

In various embodiments, perfusion measurement and assessment via DCE-MRI or other imaging modalities could be performed at the capillary level, especially in terms of 'high spatial resolution' type DCE-MRI. Such scans could potentially differentiate where contrast material were to "leak out" and accumulate in extravascular, extracellular-matrix (ECM) space, and could also measure where and/or if the contrast material eventually "cleared out" of the ECM, given a sufficient scan duration. This could significantly improve the ability to image and resolve the actual blood and/or nutrient flow as compared to imaging of the exchange between the 'vascular' space (capillary) of interest and the ECM space (which may be of lesser interest, depending upon the surgeon's preference). For example, if the imaged contrast-material were of the intravascular type (i.e., it does not easily leak out from 'normal' capillaries), the level of detectable signal 'enhancement' that could be measured during DCE-MRI scanning might be very low because of the relatively small percentage that might be considered as 'vascular space' in a typical imaging voxel-size for most biological tissue.

Similar differentiation of such extravascular and/or extracellular presence of contrast (i.e., Omniscan: Gd-DTPA-BMA) could be possible with contrast material used in other imaging modalities, including routine imaging modalities such as CE-MRI. If desired, the assessment of blood supply or flow into such capillary networks could also be evaluated 'up-stream' (i.e., in larger arteries) and/or "downstream" as part of the imaging and assessment process herein.

In various embodiments, the use of combinations of CE-MRA and DCE-MRI in the same MRI or in a sequential scanning session could be performed. While CE-MRA can be combined w/CE-MRI, CE-MRA may not provide a desired level of 'quantitative' information to the surgeon as compared to an equivalent DCE-MRI imaging session. In such situations, the use of higher strength magnet systems could desirably allow the injection of reduced doses of contrast for such serial imaging, thereby allowing for the collection of greater amounts and/or resolutions of data (which can be combined post-imaging, if desired) than that of a single imaging modality alone.

In various alternative embodiments, the use of intravascular contrast material might be preferred, as this material may not lend itself to diffusion from the vasculature, but such use could also be limited in its imaging of diffusive patterns from the capillary network through the intervertebral endplate. In contrast, the use of easily diffusing contrast, in combination with the ability to differentiate leaking contrast versus intravascular contrast, could potentially facilitate direct imaging of flow patterns and vasculature structure, while ignoring or discounting such contrast potentially in the (ECM) space.

Spinal MR Spectroscopy and Other Studies

A loss of perfusion at the vertebral endplate can result in less oxygen available for diffusion across into the nucleus of the disc. Since simple diffusion appears to be the primary mechanism for solute transport within the disc and not a pumping action, the oxygen concentration at the vertebral endplate can be critical. Loss of oxygen (hypoxia) results in the chondrocytes shifting to anaerobic metabolism to produce energy. This inefficient process is associated with a shutdown in matrix production and resulting poor matrix repair and maintenance. High field strength spectroscopy (which is desirably of at least 3 Tesla strength, although lesser or greater strengths may be used with varying levels of utility) may be extremely important in the delineation of metabolic abnormalities associated with ischemia within the intervertebral disc. It has been demonstrated that lactate levels are elevated in discs dependent upon anaerobic metabolism. Therefore, lactate could be used as a biochemical marker signifying a disc that is "stressed" and at risk. In addition, low pH (associated with high lactate) has been demonstrated to be a biochemical mediator of discogenic pain. Other useful markers that may correlate with ischemia/hypoxia and the painful, degenerative disc include, but are not limited to, determination of 31P levels as an indicator of energy level, water content as an indicator of proteoglycan content and disc size. A larger disc can indicate less efficient distribution of oxygen and an increase in anaerobic metabolism.

Hallmarks of disc degeneration can include loss of proteoglycans, water, and Type II collagen in the disc matrix. Other changes in the matrix are less well defined, including loss of the higher molecular weight proteoglycans, collagen cross-linking and organization of the proteoglycan, etc. An important process in disc degeneration appears to be the change of the differentiated chondrocyte phenotype in the nucleus pulposus into a more fibrotic phenotype. Together these changes in the disc matrix lead to alterations of the disc and vertebral anatomy that ultimately are associated with a pathologic condition. Even though the turnover rate of PG's may be very long, longitudinal imaging can be an excellent method of quantification of chondrocyte recovery and return to synthetic function. PG is negatively charged and it has been determined that the tissue integrity can be preserved by maintaining a fixed charge density in cartilage. Sodium ions, which are positively charged, are attracted by this fixed charge density. The sodium content of cartilage can be correlated with its fixed charge density, hence the PG content. With proper imaging protocols, the measured sodium signal can be directly correlated with PG content and negatively correlated with T1 and bi-exponential T2 values. Accordingly, in at least one exemplary embodiment, such sodium imaging can be utilized as a marker for disc degeneration.

In one exemplary embodiment, proteoglycan quantification could be measured in vivo using a MRI imaging technique called T1rho (T1ρ) sequence. Just as ADC value (ADC-mapping) can be a quantitative outcome of diffusion-weighted imaging (DWI), T1rho relaxation time (T1rho mapping) can be an outcome of T1rho weighted imaging wherein the relaxation time is shown to be directly correlated to PG (proteoglycans) content. Relevant data obtained could be used by a clinician to identify the hallmarks of disc degeneration, including the loss of proteoglycans, water, Type II collagen and/or other changes in the disc matrix, and recommend further analysis, imaging and/or treatment including the various techniques described herein.

Combination Imaging Strategies

In various embodiments, combinations of imaging strategies and/or methodologies can be employed to collect image data. In various embodiments, the various image data types obtained can be used for generation of algorithms to include/exclude patients for the treatment of lower back pain or other pathologies, and identify "at risk" tissues, including those suffering from vascular or diffusive deficiencies and/or structural deficits such as vertebral osteoporosis. Combining imaging studies may provide important insight into the description of heretofore unknown vascular diseases of the spine or other joints and tissues. In one embodiment, the clinician treating patients with lower back pain may recommend longitudinal DCE-MRI for analysis of endplate perfusion along with T1ρ and ADC. These studies can show a correlation of accelerated detrimental changes within the disc that, coupled with an association with hypoperfusion and/or ischemia of one of both of the vertebral endplates may satisfy one or more inclusion criteria for treatment of the hypoperfused endplate with angiogenesis. This static image combination could provide important clinical information that leads to medically necessary treatment protocols. In addition, combinations of image techniques might be utilized—i.e., multiple different imaging modalities within a short time period and/or multiple imaging modalities over time using complimentary, serial modalities for analysis. A clinical treatment plan could also be developed based upon the results of the multiple/serial imaging acquisitions.

Intervertebral Disc and Spinal Imaging Considerations

An unusual feature of the intervertebral disc is that it is typically capable of receiving nutrition via diffusion from vertebral bodies both above and below the disc. This dual vascular flow, which delivers nutrients to every disc from the superior and inferior endplates, has a potential to complicate the analysis, assessment and treatment of vascular hypoperfusion and deficient diffusive nutrient flow of the disc. Because the disc can potentially receive such nutrients from both sources, a deficiency in one source may not have a significant clinical consequence mandating immediate treatment. In order to assess such considerations, however, it is desirous to obtain image data for both the upper and lower vertebral body structures' endplates adjacent to each intervertebral disc.

Experimentation has demonstrated 2 overlapping vascular systems within the vertebral body. One appears to be targeted to marrow perfusion with rapid flow and the other for subchondral endplate nutrient and waste exchange. An initial dynamic MR Perfusion technique utilized a more pronounced temporal resolution with less spatial resolution and demonstrated rapid flow into the middle of the vertebral body with a rapid wash-out rate. In one exemplary embodiment, modification of pulse sequences for a higher spatial resolution (smaller voxel size with a sub-millimeter in-plane resolution) at a cost of lower temporal resolution (a longer sampling time for each dynamic frame) localized enhancements around vertebral endplates that were not evident from the data provided by a higher temporal resolution DCE-MRI (at a cost of lower spatial resolution) In addition, this technique displayed time-course data (dynamic data) that is more associated with a discontinuous (or porous) capillary network. It is believed that this type of capillary is utilized by the hematopoietic functions of the vertebral body to a greater extent (allowing large cells to migrate from the intravascular and extravascular compartments). However, where a modified DCMRI (dynamic contrast magnetic resonance imaging) perfusion study is utilized, a significantly greater spatial resolution (and less temporal) protocol can be achieved, and this approach demonstrates significantly greater detail at the endplates. Utilizing such a modified imaging protocol, it is possible to successfully image an enhanced endplate capillary network that can provide useful image data to be analyzed in various of the embodiments described herein. Such imaging parameters allow detection of a time-course data consistent with a function of nutrient exchange.

In various embodiments, scans can be created demonstrating significant dynamic endplate perfusion that can be quantified with resolution up to 1 mm "in plane" and showing time course data that is consistent with capillaries that are continuous (no pores).

It is believed that various imaging and analysis approaches to the imaged data can be utilized in varying ways to identify vascular deficiencies and/or diffusion insufficiencies adjacent to the intervertebral endplates. In various embodiments, image data can be acquired that reflects perfusion of blood in and/or proximate to the vertebral endplates. Where proper imaging modalities are used, and combinations of such data obtained from differing imaging modalities combined in a desired manner, image data can be acquired that reflects the flow and/or flowpaths of blood and/or other nutrients in the intervertebral vasculature In various alternative embodiments, image data can be acquired that reflects the structural composition of the intravertebral structures, including reconstruction of the various circulatory and microcirculatory paths proximate the endplate. Another approach could include imaging and/or analysis of waste metabolites or "markers" exiting the vertebral structure, which may include collection and analysis of blood or other fluids exiting the vertebral bodies or non-invasive imaging assessment of the presence of such waste "markers" in the vascular system and/or relevant tissues of the intervertebral discs and/or vertebrae.

In various embodiments described herein, anatomical image data from a patient can be obtained and the image data for one or more vertebral bodies and associated disc structures of the patient's spine can be analyzed for the presence and/or likelihood of vertebral body and/or disc ischemia. For example, the image data of a subchondral capillary bed of a vertebral body immediately adjacent to a disc endplate can be selected and analyzed using various techniques described herein, and the resulting analysis queried for the presence of hypoperfusion.

In one particular preferred embodiment, parameters used for MR imaging of discs may include: TR 3200 ms, TE 119 ms milliseconds, and thickness of 4.0 mm with gap 0.4 mm. In one alternative embodiment, parameters used for MR imaging of discs could include: a final T2w protocol of TR/TE=5000/120 (ms) and imaging voxel-size equal to 0.8×0.8×3.0 (mm) or 3.0-mm gap with no gap.

Numerous methods are known in the art that could potentially be used to identify areas of hypoperfusion, as well as image the disc segment causative of lower back pain. These methods can include MR-based techniques such as diffusion-weighted imaging, T2 and T1-weighted anatomical magnetic resonance imaging (MRI), diffusion tensor imaging (DTI), magnetic resonance spectroscopy (MRS), T1ρ weighted MRI, dynamic contrast-enhances MRI (DCE-MRI), T2 relaxometry MRI, CT-scan (computed tomography scan), and provocative discography. Diffusion-weighted imaging can provide quantitative analysis of disc degeneration and early changes over time as previously described. T1ρ MRI can be used to measure proteoglycan content. Any of these techniques may be used alone or in combination to diagnose lumbar ischemia as described.

In one particular embodiment, the area of hypoperfusion is identified using technetium-99m Sestamibi in conjunction with single photon emission computed tomography (SPECT) imaging. This radiolabelled lipophilic cation is injected intravenously at concentrations ranging from 200-1790 MBq, more preferably 500-1000 MBq, and even more preferable at approximately 750 MBq. Imaging is performed with a gamma camera and absorption/perfusion is quantified using various software packages known to one skilled in the art. In some embodiments, to attain appropriate images of the lumbar area, the camera is rotated 360 degrees.

In other embodiments, various means of detecting hypoperfusion are employed, for example, PET-CT (positron emission tomography-computed tomography), DCE-MRI, and, for example, fluorescent peptide-based methodologies.

Imaging of Segmental Arteries

Various embodiments of the invention can include imaging of anatomical structures that can be directed to detection of ischemia-associated osteoporosis and subsequent treatment through angiogenic stimulation. While previous studies have demonstrated an association between atherosclerosis and osteoporosis, a causal relationship was not identified. The invention discloses a novel diagnostic algorithm that can be utilized in the diagnosis and selection of patients for subsequent treatment utilizing pro-angiogenic approaches. To date, a diagnostic imaging algorithm has not been developed since no vascular basis for spinal disease has been accepted in the field of spinal medicine and surgery. In one aspect of the invention, magnetic resonance angiography (MRA), a special type of MR which creates three-dimensional reconstructions of vessels containing flowing blood, is utilized to identify vascular abnormalities. By imaging the segmental arteries, a rating system can be developed measuring the amount of patency of the vessels. The following system is an example of such a system:

| Arterial Occlusion (L1-L5): 2 vessels (left and right) |
| --- |
| 0 = both vessels are patent |
| 1 = one vessel is stenotic |
| 2 = both vessels are stenotic |
| 3 = one vessel is occluded |
| 4 = one vessel is occluded and one stenotic |
| 5 = both vessels are occluded |

Similar to this segmental artery grading system, vertebral endplate perfusion could be defined with a numerical scale depending upon the hypoperfusion location in the endplate, the quantity of perfusion and the level of endplate loss of integrity and disc degeneration (based upon ADC and/or T1ρ.

| Superior and Inferior Endplate Perfusion Possible Classification System |
| --- |
| 0 = both endplates with adequate perfusion |
| 1 = Inferior endplate shows hypoperfusion |
| 1a = Superior endplate shows hypoperfusion |
| 2 = both endplates show hypoperfusion |
| 3 = Inferior endplate shows no perfusion |
| 3a = Superior endplate shows no perfusion |
| 4 = Inferior endplate shows no perfusion and superior endplate shows hypoperfusion. |
| 4a = Superior endplate shows no perfusion and Inferior endplate shows hypoperfusion. |
| 5 = both endplates show no perfusion. |

This classification system could be as simple as the above chart with complexity being added depending upon the inclusion criteria that develops by researching various combinations of imaging techniques as described herein (including, for example, combination imaging strategies, etc.). With further quantitative endplate research, numerical criteria could determine classification, along with other quantitative imaging assessments already discussed, creating a clinically relevant classification system.

Data Modification, Analysis and Assessment

Once sufficient image data has been obtained, and has been sufficiently segmented and identified as relevant, it can be analyzed in a variety of ways. The data may also be processed, enhanced, filtered and/or otherwise modified in a variety of ways to desirably enhanced the detection and identification of various values of interest, which in various embodiments may include structural and/or functional qualities of intraosseous microvasculature and capillaries. While various embodiments described herein include the analysis and assessment of spinal, vertebral and intervertebral disc pathologies, it should be understood that the techniques and treatments described herein can be applied with equal utility to other joints of a human or animal body, as well as to other tissues and organs.

Various embodiments described herein include the use of a variety of image data types, and a variety of analysis approaches to the imaged data, which can be utilized in varying ways to identify vascular deficiencies and/or diffusion insufficiencies adjacent to the intervertebral endplates. Relevant image data and analysis particularly useful in various embodiments disclosed herein can include one or more of the following (each of which may be utilized alone or in any combinations thereof): (1) analysis of the structure of bones and/or soft tissues of the spine, including relevant vasculature, micro-vasculature and endplate structure and composition, (2) analysis of the flow and/or flowpaths of blood and/or other nutrients and wastes, and (3) analysis of nutrients, waste metabolites and/or "markers" entering and/or exiting the disc and vertebral structures, which could include collection and analysis of blood or other fluids exiting the vertebral bodies or non-invasive imaging assessment of the presence of such nutrient/markers in the vascular system and/or relevant tissues of the intervertebral discs and/or vertebrae.

As previously noted, one unusual feature of the intervertebral disc is that it can be capable of receiving nutrition via diffusion from vertebral bodies both above and below the disc. This dual vascular flow that delivers nutrients to every disc from the superior and inferior endplates can potentially complicate the analysis, assessment and treatment of vascular hypoperfusion and deficient diffusive nutrient flow of the disc. In various embodiments, such dual flow is accommodated in the imaging and analysis of an individual intervertebral disc.

In various exemplary embodiments, the relevant features of both the upper and lower vertebral body structures adjacent to the endplates of a single intervertebral disc are desirably imaged, identified and analyzed. Because the disc can potentially receive such nutrients from both vertebrae, a deficiency in one source may not necessarily result in significant disc degradation. For example, experimental data has shown that the superior endplate of most discs shows greater perfusion than the inferior. However, where both sources are compromised to some degree, or where a significant degradation of one source cannot be accommodated by the other endplate, the diagnosis may mandate some form of angiogenic (or other) treatment. Of course, the imaging and analysis of an individual endplate may be most desirable where intravertebral vascular flow within a given vertebral body adjacent to the endplate can be assumed as degraded or deficient (i.e., such as where the adjacent vertebral body has been filled with bone cement during a prior, concurrent and/or anticipated kyphoplasty or vertebroplasty procedure). In various embodiments, the effects of annular diffusion and/or other nutrition/waste pathways relative to the disc anatomy may be imaged, quantified and analyzed in the various analytical and treatment regimens described herein.

In various embodiments, three-dimensional (3D) imaging data of a patient's anatomical structures immediately adjacent to the upper and lower endplates of an intervertebral disc can be obtained and analyzed. In at least one desirable embodiment, the 3D data will include information regarding the anatomical structure of an entire endplate to a depth of at least 2 to 3 mm from the endplate into the vertebral body (a "Region of Interest"). In addition, the 3D data will desirably be of a sufficient resolution to differentiate and identify the relevant vasculature within this Region of Interest, including the various features of the capillary beds and optionally the venules and/or other microstructure therein. In various embodiments, the data may alternatively and/or in addition comprise analysis of the perfusion of blood and/or other nutrients and wastes and/or analysis of nutrients. In a similar manner, waste metabolites and/or "markers" entering and/or exiting the disc and vertebral structures can be imaged and analyzed. In addition, since the ROI (region of interest) could be placed anywhere on the scanned spine, the spinal cord can be investigated with this technique, providing another category of spinal disease (spinal cord injury) with vascular anatomy imaging (MRA) and simultaneous Dynamic Perfusion.

The typical degenerative process of an intervertebral disc can be a slow, continuous process, which is expected to be at varying functional stages for discs classified into any given Pfirrmann grade (1-IV). However, quantitative measurements such as those described herein may delineate subtle changes that can be clinically relevant. As precursor to morphologic changes, such functional measurements may be especially valuable during the early phases of the degeneration process where no morphological change is expected or anticipated to be present in the disc, or at least not at an easily detectable level. Ideally, any potential quantitative, functional measurement reflecting the dynamic degenerative stages can be evaluated in correlation to an established quantification method, which could include quantification based on other functional aspects of the intervertebral disc. Where such subtle changes can be identified and/or detected, they can also be treated with several of the methods described herein (as well as others that may be developed in the future), which may slow, prevent and/or reverse the onset of later stages of disc degeneration.

In various embodiments, assessment of a patient's intradiscal diffusion may include the identification of an Apparent Diffusion Coefficient (ADC) measurement, which can be an intervertebral disc functional quantitative rating for diffusion and/or T1$\rho$ relaxation time which is believed to reflect PG content in the nucleus pulposus of disc. Both ADC and T1$\rho$ quantitative measurements desirably enable imaging and detection of small changes over time to allow identification and/or quantification of one or more "at risk" discs. In various embodiments, the "at risk" disc could be either one that is associated with subtle changes in the ADC and/or T1$\rho$ value as well as an increased level of pain which may or may not be associated with changes in the image morphology, or Pfirrmann grade, of the disc. In addition, in various embodiments, one or more intervertebral discs that are adjacent to (either proximal and/or distal to) a planned or already performed lumbar arthrodesis, plating, dynamic stabilization, interspinous stabilization and/or other spinal procedure such as arthroplasty might be considered "at risk" with certain combinations of ADC/T1$\rho$ (or changes in ADC/T1$\rho$ or other quantitative measurements), endplate vascularity and/or other quantitative measurements of disc integrity. These measurements could prompt a corresponding treatment to improve the endplate vascularity either prior to arthrodesis or other surgical treatments, during surgical intervention and/or subsequent to surgical treatment and/or follow-up.

A significant advantage in the employment of the imaging and assessment systems described herein is the ability to measure and assess small changes in the disc over time in a highly accurate manner. This facilitates the identification and/or quantification of subtle metabolic and structural changes in one or more "at risk" discs. Until the approaches described herein were developed, such subtle changes were difficult and/or impossible to detect, which made it commensurately difficult to determine if a given surgical intervention and/or treatment was particularly effective in treating and/or ameliorating a degenerative disc condition. By employing the various systems and methods described herein, however, it becomes a relatively straightforward process to assess and quantify the various advantages and/or disadvantages a given clinical intervention provides to treatment of an intervertebral disc and/or spinal segment. Measuring the nutritional and metabolic parameters of discs before and after treatment can offer an evidence-based approach to analyzing the outcome, which can be of significant value to the assessment of existing disc treatment regimens as well as those to be developed in the future.

In some embodiments, specific grades of disc degeneration can be chosen for treatment, or a relative measure between intervertebral discs and/or intravertebral/endplate perfusion values at multiple levels of a single patient may be compared to identify one or more levels having unusual and/or atypical values, which may indicate need for treatment and/or further assessment.

Analysis and Assessment of Vertebral Body and Endplate Anatomy

FIG. 7A depicts a side plan view of an exemplary spinal motion segment 100, comprising an intervertebral disc 110 separating a cephalad or superior vertebrae 120 and a caudad or inferior vertebrae 130. The intervertebral disc includes a superior endplate 112 and an inferior endplate 114. FIGS. 7B and 7C depict top and side plan views of one exemplary vertebral body 105. The configuration of specific vertebrae in the spine differ somewhat at each level, but vertebrae in general include a vertebral body 140, which is the anterior, massive part of bone that gives strength to the vertebral column and supports body weight. The vertebral arch 150 is posterior to the vertebral body 140 and is formed by the right and left pedicles 155 and 160 and lamina 170. The pedicles 155 and 160 are short, stout processes that join the vertebral arch 150 to the vertebral body 140. The pedicles 155 and 160 project posteriorly to meet two broad flat plates of bone, called the lamina 170.

Seven other processes arise from the vertebral arch. Three processes, called the spinous process 190 and two transverse processes 200 and 205, project from the vertebral arch 150 and afford attachments for back muscles, forming levers that help the muscles move the vertebrae. The remaining four processes, called articular processes, project superiorly from the vertebral arch (and are thus called the superior articular processes 210) and inferiorly from the vertebral arch (and are thus called the inferior articular processes 220). The superior and inferior articular processes 210 and 220 are in opposition with corresponding opposite processes of vertebrae superior and inferior adjacent to them, forming joints, called zygapophysial joints or, in short hand, the facet joints or facets. Facet joints are found between adjacent superior and inferior articular processes along the spinal column and the facet joints permit gliding movement between the vertebrae.

Discs are roughly cylindrical or oblong structures that vary in size and shape progressively from the cervical to the lumbar region. As is best seen in FIG. 8, the intervertebral disc is comprised of an outer annulus fibrosis 250 and an inner nucleus pulpous 260 disposed within the annulus fibrosis 250. The annulus fibrosis 250 consists of a tough fibrosis material which is arranged to define a plurality of annular cartilaginous rings 270 forming the natural striata of the annulus. The nucleus pulpous 260 consists primarily of an amorphous gel having a softer consistency than the annulus 250. The nucleus pulpous 260 usually contains 70%-90% water by weight and mechanically functions similar to an incompressible hydrostatic material. The juncture or transition area of the annulus fibrosis 250 and nucleus pulpous 260 generally defines, for discussion purposes, an inner wall or inner annulus 270 of the annulus fibrosis 250. The disc cortex or outer annulus 280 surrounds the annulus fibrosis 250.

At the cranial and caudal ends of each disc are the endplates that separate the vertebral bone from the disc itself and prevent the highly hydrated nucleus from bulging into the adjacent vertebrae. The endplates also absorb the considerable hydrostatic pressure that results from mechanical loading of the spine. The endplates are typically less than 1 mm thick, and while this varies considerably across the width of any single disc, they tend to be thinnest in the central region adjacent to the nucleus For a typical intervertebral disc, the subchondral vasculature within the adjacent vertebral body will not be constant across the entire endplate, but rather varies depending upon the relative location of the endplate analyzed. For example, as can best be seen in FIG. 9, there is less vasculature at the periphery 310 of the endplate 300, but there is generally significant vasculature at the center 320 of the endplate. The lateral margins of the endplate near the vertebral rim are relatively impermeable compared with the central portion or the entire annulus, and microscopic blood vessels in the central endplate are more numerous than in the margins of the disc. A dyed and fixed specific of an exemplary spinal motion segment, which included an intervertebral disk between two vertebral bodies, is shown in FIG. 10. This image depicts a superior vertebral body 350 and an inferior vertebral body 355, separated by an intervertebral disc 360. Various endplate capillary networks are depicted, including an inferior endplate capillary network 365 and a superior endplate capillary network 370.

In various spinal levels, the predominant capillary network that provides nutrients is located proximate to the middle of the endplate and disc, within the vertebral body, in association with the cartilaginous endplate. This network can be fed by a penetrating artery 302 or other vascular source. The capillaries 305 may project into the cartilaginous endplate 300 and then loop back towards the vertebral body and are involved in delivery of nutrients 307 (i.e., oxygen and glucose) and waste removal. The looping portion of the capillaries is exposed to intradiscal and endplate hydrostatic pressure, which can be increased in normal positions of daily life but also in pathologic conditions. Accelerated stress on the endplate can result in early calcification, best described in adolescent idiopathic scoliosis patients. This increased pressure may be responsible for the diminished capillary population, (or suboptimal morphology) that is seen with age, with some degenerative discs showing a greater degree of capillary loss than others. Eventually, the endplate itself can become a hindrance to the diffusion of nutrients creating another obstacle to proper disc chondrocyte nutrition.

While the capillaries at the endplate are diminishing, abnormal annular capillary growth may also be induced in response to metabolic derangement, tissue breakdown and inflammation. As these vessels grow into the disc, they can bring nociceptor (pain fibers) nerves that can be sensitized by metabolic by-products such as lactate (and the corresponding lower pH). Lactate may be increased in discs experiencing discogenic pain. Utilizing NMR spectroscopy on disc specimens from normal scoliosis patients vs discogram-defined discogenic pain patients, experimentation has demonstrated an increased lactate concentration in these "painful" discs. Accordingly, metabolic wastes such as lactate may create a hypersensitivity of nerves that have grown into the disc due to the metabolic derangement. As already stated, nociceptive nerves are many times associated with abnormal ingrowth of annular capillaries. It is proposed that disc vascularization can occur before innervation, and that the vascular mechanism may be predominant. While the mechanism of this vessel/nerve ingrowth is not fully confirmed, it is believed to be a response to injury/inflammation. It is also believed that lactate (and other byproducts of ischemia) may function as a stimulus to promote some level of angiogenesis in some manner through the VEGF pathway.

Various embodiments described herein include the employment of 2-dimensional and/or 3-dimensional analysis of the intravertebral circulation and microcirculation directly adjacent to one or more intervertebral disc endplates. This may include localized analysis and/or "weighting" of the circulation/microcirculation measurements in different areas of the vertebrae and/or endplate, as the vertebrae microcirculation proximate the edge of the endplate and or near the annulus) may be of a lesser quantity and/or lesser effect to overall diffusion than the structures proximate the center of the endplate (including points closer to the inner annulus and nucleus), which may contribute the bulk of nutrition/waste disposal for the disc. In addition, multi-parametric analysis provides a method to assess multiple aspects of a pathologic process that may exist simultaneously. This technique can provide important information on the degree of disc degeneration and the importance of the possible endplate perfusion etiology.

Metabolic Wastes

As previously noted, various embodiments described herein can include the use of imaging and assessment of endplate perfusion combined with measurement and/or assessment of lactate levels within an intervertebral disc with a minimally invasive diagnostic study, which can potentially provide independent confirmation of the disease diagnosis. Removal of waste may be measured by imaging either lactate or Hydrogen ion over time. If the imaging shows improvement of the amount of these metabolic waste products, then some conclusions can be drawn as to the integrity of the waste removal system. Conversely, an increased level of such wastes could lead to a diagnosis of deficit and/or failing waste removal systems. In addition, real time imaging would be possible with imaging sensitive markers tagged to these, or other waste metabolites.

The diagnosis and relevant treatment of the cause(s) (abnormal load distribution with resultant poor nutrient delivery and waste removal) as described herein could significantly improve clinical management of disc disease. The ability to measure lactate can provide a metabolic marker that can be utilized to evaluate longitudinally, or eventually, help in the diagnosis of the painful disc. In one exemplary embodiment, MR Proton spectroscopy can be utilized to monitor the lactate content in tissues non-invasively. Alternatively, a MR spectroscopy protocol PRESS (point resolved spectroscopy) with CHESS (chemical shift selective) pulse to suppress water signal could be implemented to quantify lactate content in tissues. This type of spectroscopy in-vivo is possible with specialized hardware (coils) and appropriate software development. Experimentally, imaging on a subject in a 3T scanner has been accomplished, demonstrating a higher lactate level at amore degenerative L5-1 disc. As described herein, improved data analysis will occur with PRESS and SHIFT protocols, providing cleaner lactate data.

Screening

In various embodiments, patients with advanced lumbar back pain can be screened to determine whether the pain is associated with disc degeneration. Such screening is common medical practice with other pathologies, and can include techniques such as physical examination, radiographic studies, MRI and bone scans and discograms, with or without post-discogram CT scans, to diagnose "discogenic" pain, or pain associated with degeneration of the annulus fibrosus, nerve irritation by the nucleus pulposus, or other chronic pain. Patients with rheumatoid arthritis, spinal infections or tumors, acute nerve compression and/or arthritis could be excluded from eligibility for treatment (if desired) using the methods and compositions described in the present invention. In a variety of cases, patients treated with the various inventions disclosed herein might be refractory to conventional treatments such as anti-inflammatory medication or analgesics. In a more specific embodiment, patients can be diagnosed based on degeneration of a single or plurality of discs using magnetic resonance imaging. In preferred embodiments, disc degeneration can be estimated from regular lumbar T1 and T2-weighted MR sagittal fast spin-echo (FSE) and T2-weighted FSE axial images. Preferably, the intervertebral discs may be classified according to three grades: grade 0, discs with high signal intensity or only slightly blurred intranuclear cleft, which represent normal discs; grade 1, discs with decreased signal intensity but normal height, which represent mild degeneration; and grade 2, discs with markedly decreased signal intensity and height loss, which represent severe degeneration. In preferred embodiments, the signal intensities of intervertebral discs can be compared with those of cerebrospinal fluid. If desired, ADC and T1rho could be added to the T1 and T2w scans to analyse diffusion and proteoglycan content in an effort to quantitate the degree of disc degeneration.

In one embodiment, ADC can be utilized to quantitate disc degeneration with or without combining the data with qualitative approaches such as Pfirrmann grading. A multi-parametric approach may be more appropriate wherein morphologic assessment of degeneration is utilized in conjunction with more quantitative measurement such as ADC. With large sample sizes, subcategories could be developed that correlated with specific degenerative patterns that may or may not require clinical intervention. FIG. 19 demonstrates that ADC can measure diffusion in any plane. In addition, the relative contribution can be ascertained. These ADC maps show greater diffusion in the Superior-Inferior plane in the normal discs and heterogeneity in the abnormal discs. (Anisomery maps) The ADC maps can also be a representation of data that can correlate well with Pfirrmann grades.

In various embodiments, genetic screening and/or whole genome sequencing could be used to elucidate whether a patient that has a greater potential to develop degenerative disc disease, as well as to determine which patient may or may not be receptive to various types of gene therapies or other treatments, including angiogenic treatments. Comparing gene sequences in patients with degenerative disc disease and lower back pain with patients without these disorders can create one or more standards to facilitate a blood test that could alert clinicians to the patient's susceptibility for degenerative disc disease and progressive lower back pain. This information, coupled with the imaging data already discussed, could refine the decision algorithms for treatment of lower back pain due to ischemic disc disease.

In various embodiments, it may be desirous to identify a non-treatable disc or other spinal pathology that reduces and/or negates the effectiveness of a given course of anticipated treatment. Various types of image data could be employed to perform such analysis, such as plain x-rays that could show severe deformity that could be a contraindication for angiogenic treatment. Image data may be used to detect a calcified and/or thickened endplate that could inhibit diffusive transfer and reduce and/or negate the effectiveness of angiogenic treatments in various circumstances. In addition, image data showing severe loss of disc height and therefore missing and/or severely degenerated disc material may not allow the disc to be treated. In addition, severe sclerosis of the endplate may not allow angiogenesis to occur into the nutrient exchange area of the endplate.

Segmental Vessel Analysis

Once an ischemic vertebral body and/or disc has been identified using analysis of the subchondral capillary bed image data or one or more of the other imaging and analysis techniques described herein, various embodiments can include further analysis of anatomical image data of the major circulatory systems that feed into and/or drain out of the subchondral capillary bed, to identify any occlusions or partial occlusions that may be contributing to the ischemic diagnosis. Where such occlusions or partial occlusions are identified, a desired course of treatment may include angiogenic and/or surgical treatment of the occlusions or partial occlusions alone and/or in combination with angiogenic treatment of the subchondral capillary bed. Where such occlusions or partial occlusions are not identified, a desired course of treatment may primarily involve angiogenic treatment of the subchondral capillary bed alone.

In various embodiments, combining vertebral perfusion (of the vertebrae above and below the disc studied) with imaging and analysis of segmental artery stenosis and/or the degree of degenerative disc disease (and possibly diffusion and/or spectroscopy data) may describe a "new" etiology for subsets of patients with degenerative disc disease and osteoporosis.

In one exemplary embodiment, subjects can be scanned using combinations of Magnetic Resonance Imaging (MRI) and Magnetic Resonance Angiography to (MRA) to assess the condition and/or treatability of their pathology. Exemplary 3D Contrast enhanced MRA scans could be acquired with 50 coronal slices using TR: 5.1 ms, TE: 1.78 ms, voxel size=0.8×0.8×1.5 mm$^3$, SENSE: 4. Data acquired in this method could be assessed and/or combined in various ways. For example, the segmental vessels on MRA could be graded as occluded, stenotic or open (or other more graduated assessments could be applied). If desired, relevant intervertebral discs could be graded as per Pfirrmann. The endplate structure could be analyzed and graded. Image data reflecting the structure and/or perfusion of the capillary vessels and/or microvasculature in the vertebral body structures proximate to the intervertebral disc endplates could be assessed. In addition, the peripheral branches and/or the second segmental artery can be analyzed and graded as occluded, stenotic or open (or other more graduated assessments could be applied), and potentially assessed as to whether they could be sufficient to compensate for an ischemic peripheral vessel. In addition, MRI and MRA data sets could be overlaid and/or combined to create composite data maps, including the use of color mapping to identify relevant features of interest.

Diagnosis and Treatment

Once an area of deficient nutrition, vascular perfusion and/or other anatomy of interest has been identified and analyzed, it may be desirous to treat the area (or other relevant anatomical structures) in an attempt to slow, halt and/or reverse the progression of diseases that may be present and/or develop in the future.

As used herein, the terms "treating," "treatment," "therapeutic," or "therapy" do not necessarily mean total cure or abolition of the disease or condition. Any alleviation of any undesired signs or symptoms of a disease or condition, to any extent, can be considered treatment and/or therapy. It is entirely possible that "treatment" consists of a temporary improvement of the endplate vasculature that requires repeated treatment over time to continue the regenerative process. In addition, asymptomatic degenerative disc disease may be the focus of treatment utilizing angiogenesis. Furthermore, treatment may include acts that may worsen the patient's overall feeling of well-being or appearance.

Once an area of hypoperfusion or other deficit is identified as described herein, the patient may be diagnosed with hypoxic and/or ischemic tissue disease, and various embodiments include the induction of neovascularization so as to enhance localized perfusion to the area of need. In the case of a diagnosis of ischemic vertebral and/or disc disease relevant to the intervertebral disc, various embodiments include the induction of neovascularization so as to enhance localized perfusion to the area of need. If desired, quantitative measurements of diffusion weighted imaging and Apparent Diffusion Coefficient or ADC can be utilized to identify "at risk" disc or other tissues (which could also include determining the degree of such hypoperfusion and/or utilizing such information to verify the identity of an "at risk" disc). Alternatively, or in addition to such ADC measurement and assessment, endplate integrity imaging using either Ultra-short TE (UTE) imaging of the intervertebral endplate, assessment of proteoglycan content of the disc using T1rho magnetic resonance imaging quantification, measurement of lactate removal by a "metabolite imaging" technique such as Magnetic Resonance Spectroscopy (or 1H-MRS) or phosphorus scanning such as 31P-MRS for pH or bioenergenic metabolism of the disc, or similar assessment methodologies could be employed. In other embodiments, various combinations of the above-reference data could be combined with endplate vascularity and any information regarding the change in the symptoms and other clinical factors of the disc or related anatomy to define the medical necessity for angiogenic treatment. The totality of these imaging modalities can be summed up by the process of imaging the entire nutrient delivery pathway to the disc. At each level, nutrient delivery has the potential to be halted and the disc integrity and bioenergetics affected. Measuring the level of blockage and its resultant effect on the disc can potentially be accomplished using any combination of one or more of the imaging modalities of FIG. 15, where endplate perfusion can be measured with DCE-MRI, disc integrity and diffusion characteristics analyzed with T1rho and ADC, endplate integrity quantified with ultrashort time to echo MRI (or some other endplate integrity scanning modality) and cellular metabolism measured with some form of molecular imaging such as lactate or sodium.

In various embodiments, angiogenic treatment may be optimized for use in discs that do not have significant endplate calcification. It is believed that endplate calcification may significantly contribute to the loss of nutrients to the discs. However, it is also believed that endplate perfusion deficits may be more common than once thought and permanent changes such as endplate calcification less common. Regardless of the frequency of such calcification, however, various embodiments described herein include desirably restoring perfusion to the anatomy adjacent a single endplate of an intervertebral disc (as described herein), which may ultimately provide sufficient diffusive nutrient and waste flow to maintain a minimum or acceptable nutrition level and reverse, reduce and/or slow the degradative cascade of an intervertebral disc having a completely calcified endplate on the opposing side.

In various embodiments, the medical necessity for angiogenic treatment can include identifying a patient with symptomatic low back pain, correlating a changing quantitative measurement of disc degeneration (with either proteoglycan quantification via T1rho imaging, ADC, or other quantification techniques) along with diminishing endplate capillary perfusion, and optionally assessing the presence and/or absence of endplate calcification. If desired, the patient's lumbar plain x-rays could be assessed for height and/or T2 MRI assessed for the presence and/or absence of "black disc." Such x-rays and/or MRI scans could be used to correlate the presence of disc issues and need for various treatments, such as those described herein.

In various embodiments, treatments such as those described herein may be desirous even where x-rays demonstrate a normal disc height, and/or where a T2 MRI does or does not demonstrate a "black disc." In such instances, a diagnosis of "Internal Disc Disruption" or similar pathology could be assigned to the relevant tissue structures, even where MRI of the disc itself does not indicate a vascular mechanism, and/or where x-rays of the disc appear normal. In addition, many new low back pain syndromes could potentially be defined by these imaging parameters, including various quantitative measures of disc integrity, metabolism and vascularity. In various embodiments, the medical necessity for endplate angiogenic treatment could be based upon various applications and various combinations of these objective data.

In various embodiments, 2D and/or 3D imaging studies could be employed to define the specific and/or localized areas of the intravertebral circulation and/or intervertebral disc that could be best treated with angiogenesis. If one side (left or right) of a vertebral perfusion analysis and/or intervertebral disc appeared relatively normal relative to a desired imaging quantifier and/or assessment, and the other side appeared "at risk", one potential treatment approach could be to provide an angiogenic injection within and/or proximate to the "at risk" area (i.e., injection to only the medial or lateral portion of the vertebral body). In alternative embodiments, it may be desirous to treat the "normal" level or area in an attempt to improve perfusion and/or prevent degradation in that level/area. Desirably, a combination of such treatments will desirably restore and/or regenerate the normal capillaries of one or both areas (or at least improve such vascularity in one or more areas) and produce resulting improvements in perfusion and/or nutrient/waste delivery/removal.

In various embodiments, one or both of the inferior and/or superior endplates could show diminished perfusion. As each intervertebral disc has both an inferior and superior endplate, it is possible that one or the other endplate and proximate tissues thereof could be treated first and imaging measured for improvement before the other endplate was treated.

In various embodiments, more than one disc and/or endplate level may be identified as "at risk" and in need of treatment. In this situation, imaging data may provide insight as to which vertebrae should be accessed for angiogenic treatment relevant to each disc, which in some situations may be the upper and lower regions of a single vertebral body. In such cases, a single angiogenic treatment may be used for the identified vertebral body, or multiple angiogenic injections may be provided to localized areas of the vertebral body, including to locations proximate to the upper (or superior) and lower (or inferior) endplates and/or medial, lateral, anterior, posterior and/or centralized injection sites within the vertebral body. In various embodiments, a single pedicle pathway may be used to access one or more locations within the targeted vertebral body, or both pedicles of a single vertebral body may be used for injection paths.

In various embodiments, an imaging study of a patient's lumbar and/or thoracic regions of the spine (or portions thereof) may be performed, and analysis of intravertebral vascular structures proximate to the upper and lower endplates of the intervertebral discs therein can be performed. Such studies can identify "at risk" discs and/or vasculature, which may be diagnosed for treatment and/or further study at a later date. Where "at risk" discs or vasculature may be identified, further studies may be performed, if desired.

In one exemplary embodiment of the invention, a patient can be diagnosed with hypoxic and/or ischemic disc disease and treated by increasing localized perfusion through the use of angiogenesis induction. The process of new blood vessel formation (angiogenesis) can occur naturally, or be induced through various means, include (but not limited to): vasculogenesis, arteriogenesis, and angiogenesis. For the purpose of this invention, all three will be referred to as "angiogenesis". Technically speaking, angiogenesis is associated with de novo capillary and arterial formation from pre-capillary arteries and arterioles and from post-capillary venules, is ischemia- and hypoxia-driven, and is associated with a 2-3 fold increase in blood flow. Angiogenesis can also include growth of or from existing capillaries.

Arteriogenesis is technically considered remodeling of pre-existing vascular channels (collaterals) or de novo artery formation, it can be stimulated by local changes in perfusion (shear stress), as well as cellular influx and proliferation, and associated with a 20-30 fold increase in blood flow. Vasculogenesis is technically considered on the one hand to encompass embryonic vascular development, and on the other hand to include de novo formation or remodeling of pre-existing vascular channels initiated by circulating vascular precursor cells; furthermore; it is considered to be ischemia and injury initiated. The term "angiogenesis" is meant to encompass all three technical terms.

Angiogenesis is known to occur physiologically during zygote implantation, embryogenesis, post-embryonic growth, and during tissue repair and remodeling. Pathologically, uncontrolled angiogenesis is associated with a variety of diseases such as macular degeneration, diabetic retinopathy, inflammation, including arthritis and psoriasis, and cancer. One common aspect of adult angiogenesis is tissue hypoxia. In situations of tissue expansion, cells are typically dependent on the microvasculature for nutrients and oxygen supply, as well as removal of metabolic waste products. Accordingly, during tissue growth, cells begin to "sense" a lack of oxygen. This triggers a cascade of events that culminates in angiogenesis. During pathological conditions, such as the conditions associated with hypoxic and/or ischemic disc disease, the lack of oxygen is induced through hypoperfusion. Said hypoperfusion may occur due to, for example, atherosclerosis. In some pathological conditions, the normal angiogenic response to hypoxia is absent or substantially diminished.

Although numerous methods of physiological stimulation of angiogenesis under hypoxia are known and thereby useful for the practice of the current invention, one of the most well characterized pathways involves activation of the Hypoxia Inducible Factor-1 (HIF-1), transcription factor. This protein is only functionally active as a heterodimer consisting of HIF-1$\alpha$ and HIF-1$\beta$, which are both basic helix-loop-helix proteins. While the latter is known to be relatively stable, the former has a half-life of less than 5 minutes under physiological conditions due to rapid proteasomal degradation by the oxygen sensitive von Hippel-Lindau (VHL) E3-ubiquitin ligase system. When cells experience hypoxia, HIF-1$\alpha$ half-life is increased since the degradation by VHL E3-ubiquitin ligase is dependent on proline hydroxylation, which requires molecular oxygen. Therefore, this protein modification plays a key role in mammalian oxygen sensing. Activation of this transcription factor leads to gene expression of numerous angiogenesis related genes such as VEGFs, FGF-2 response genes, notch signaling, and up regulation of stromal derived factor (SDF-1), which chemoattracts endothelial precursors during angiogenesis. There are numerous variations by which angiogenesis can occur; however, the basic steps involve remodeling of the extracellular matrix through matrix metalloproteases (MMPs), chemoattraction of either precursor endothelial cells or existing endothelial cells from an adjacent vessel, proliferation of the endothelial cells, tube formation and stabilization. Various embodiments described herein can include the transfection of genes encoding HIF-1 into areas of lumbar hypoperfusion in order to induce normalization of perfusion, or in some cases hyperperfusion in order to ameliorate or significantly treat hypoxic and/or ischemic disc disease. Embodiments described herein relate to utilization of molecules that either induce the expression of HIF-1, or conversely delay the degradation of HIF-1 or components thereof including but not limited to FGFs.

The term "therapeutically effective amount" of a compound is used herein to indicate an amount of an active compound, or pharmaceutical agent, that elicits the biological or medicinal response indicated. This response may occur in a tissue, system, animal or human and includes alleviation of the symptoms of the disease being treated. The exact formulation, route of administration and dosage for the composition and pharmaceutical compositions disclosed herein can be chosen by the individual physician in view of the patient's condition. (See e.g., Fingl et al. 1975, in "The Pharmacological Basis of Therapeutics", Chapter 1, which is hereby incorporated by reference in its entirety).). Therapeutic treatments can be achieved with small molecule organic drugs or biologics, such as proteins. Typically, the dose range of a small molecule therapeutic agent is administered from about 0.5 to 1000 µg/kg, or 1 to 500 uq/kg, or 10 to 500 µg/kg, or 50 to 100 µg/kg of the patient's body weight per dose. The dose of a therapeutic protein growth factor, such as an FGF, can be administered to the patient intravenously or intraarterially as either a bolus dose or by infusion from about 0.1 to 100 µg/kg of the patient's body weight, or 0.3 to 30 µg/kg, or 1 to 3 µg/kg of the patient's body weight per dose. To achieve localized targeted dosing, FGF-1 can be injected either directly into or adjacent to the ischemic vertebral endplate, preferably either into or as near as practical to the region of ischemia. Localized dose ranges can be from 10 ng/cm$^3$ to 1 mg/cm$^3$, or 100 µg/cm$^3$ to 100 µg/cm$^3$ or 1 µg/cm$^3$ to 10 µg/cm$^3$ of target vertebral endplate tissue per dose. Local doses can be administered at each ischemic endplate. The dosage may be a single one or a series of two or more given in the course of one or more days, as is needed by the patient. Where no human dosage is established, a suitable human dosage can be inferred from $ED_{50}$ or $ID_{50}$ values, or other appropriate values derived from in vitro or in vivo studies, as qualified by toxicity studies and efficacy studies in animals.

In various embodiments, one or more doses of a therapeutic agent, such as FGF-1, could be injected directly into the ischemic regions of the vertebral end-plates or, if not possible, then applied adjacent and as closely as possible to the ischemic endplate regions, which could include injection into the vertebral body and/or intervertebral disc. One exemplary ideal dose could be determined based on the approximate volume of the ischemic region of the disc endplate as estimated using MRI or other imaging modality. If such imaging or assessment were not practical, a clinician could set a standard dose per ischemic disc endplate based on an average human endplate volume. In various embodiments, an initial dosing goal for FGF-1 could be to achieve a target concentration of 1 to 10 ug of FGF-1 per cm3 (~1 ml) of ischemic endplate volume. If the specific endplate volume for a given patient can be determined, this value could be converted into dose levels per ischemic endplate or per cm$^3$ of ischemic or total endplate volume for each individual patient. For example, one exemplary endplate volume that could potentially be treatable using various aspects of the present invention could include a 1 cm×1 cm×1-2 mm thick volume of the endplate. Alternatively, if an average endplate and/or ischemic volume were determined, a per cm$^3$ dose of such average or actual volume could be used for a patient. In one embodiment, these proposed values could be a dose per treatment day. In other embodiments, efficacy can be improved if weekly or even twice weekly doses were given. For longer term and/or repeated does treatment of patient, the duration of such long term/repeated dosing but could be determined by subsequent MRIs or other imaging of the patient.

Although the exact dosage can be determined on a drug-by-drug basis, in most cases, some generalizations regarding the dosage can be made. The daily small molecule dosage regimen for an adult human patient may be, for example, an oral dose of between 0.1 mg and 500 mg of each active agent, preferably between 1 mg and 250 mg, e.g. 5 to 200 mg or an intravenous, subcutaneous, or intramuscular dose of each ingredient between 0.01 mg and 100 mg, preferably between 0.1 mg and 60 mg, e.g. 1 to 40 mg of each ingredient of the pharmaceutical compositions disclosed herein or a pharmaceutically acceptable salt thereof calculated as the free base, the composition being administered 1 to 4 times per day. Alternatively, the compositions disclosed herein may be administered by continuous intravenous infusion, preferably at a dose of each ingredient up to 400 mg per day. Thus, in various embodiments the total daily dosage by parenteral administration could typically be in a range 0.1 to 400 mg. In some embodiments, the compounds will be administered for a period of continuous therapy, for example for a week or more, or for months or years.

Dosage amount and interval may be adjusted individually to provide plasma levels of the active moiety, which are sufficient to maintain the modulating effects, or minimal effective concentration (MEC). The MEC will vary for each compound but can be estimated from in vitro data. Dosages necessary to achieve the MEC will depend on individual characteristics and route of administration. However, HPLC (high-performance liquid chromatography) assays or bioassays can be used to determine plasma concentrations.

Dosage intervals can also be determined using MEC value. Compositions should be administered using a regimen which maintains plasma levels above the MEC for 10-90% of the time, preferably between 30-90% and most preferably between 50-90%.

The amount of a given composition administered will, of course, be dependent on the subject being treated, on the subject's weight, the severity of the affliction, the manner of administration and the judgment of the prescribing physician.

In various embodiments, it may be desirous to treat an identified deficiency before significant disc degeneration and/or damage has occurred, even where the opposing endplate appears to be providing normal nutrition and waste removal. This can include imaging and analysis of anatomy proximate to both endplates of an intervertebral disc that can be performed to quantify whether one endplate should be treated alone or both endplates of a given disc together. If desired, the imaging data and analysis could provide an ability to compare not only each disc at risk, but also identify which endplate is the most contributing to the lack of perfusion for a specific level. This information could help in the treatment approach. In addition, the specific characteristics of the imaging data may demonstrate which vessels and/or intravertebral architecture may be susceptible to treatment versus other imaging data that shows capillaries and/or other structures that may be at a stage where treatment may not be as successful. In addition, coupling imaging data with endplate integrity data may provide insight as to how well the vessels would be predicted to grow into the exchange area of the vertebral body (i.e., proximate to the endplate) and disc and mature into functional capillaries capable of providing nutrient exchange and waste removal. Measuring the endplate and disc diffusion capabilities coupled with the endplate cartilaginous integrity and 2 or 3-D mapping of the endplate capillaries might outline the area, level, side of the disc and anterior or posterior aspect of the disc to be treated. FIG. 18 demonstrates a DCE-MRI mid-sagittal section of a lumbar spine (see also FIG. 17). The T12-L1disc mid-sagittal data can be reconstructed to create an axial section 1 mm proximal to the vertebral endplate. This generated data maps the endplate into right, left, anterior and posterior sections for careful analysis of the greatest ischemic and/or hypoxic region or relative measures thereof.

Another embodiment may provide similar treatment for the intervertebral disc (or discs) that are already degenerative with components of this degeneration that may be due to endplate hypoxia or ischemia and the resultant decrease in the necessary nutrients for matrix repair. For the disc to "heal", the necessary pathway for the nutrients required for aerobic energy metabolism could be restored. This might entail delivery of FGF-1 directly into the hypoperfused endplate. This treatment may be preoperatively planned with the proper imaging for mapping of the area to be treated. In addition, the FGF-1 (and/or other angiogenic factors or other necessary constituents) can be injected or implanted or laid adjacent to the endplate using various delivery schemes depending upon the pharmacologic properties of the various angiogenic factors and the consistency and fluid dynamics of their formulations. The treated disc's healing environment may or may not be further enhanced with implants to "unload" the disc (or discs) if it is desired by the treating physician that a more optimal biomechanical environment could be achieved with this approach. The postoperative healing environment could be assessed with serial imaging studies and treatment could be modified if necessary. This modification could alter the biomechanical properties of the "un-loading" implant to either share more or less of the motion-segment load (i.e., two adjacent vertebrae with their intervening intervertebral disc and facet joints). This alteration could be done remotely with the proper materials and controls of the implant. In addition, further treatment with the angiogenic factor could be performed depending upon the clinical and imaging information in the postoperative period.

Surgical Access, Implants, Instruments and Procedures

In various embodiments of the invention, a direct injection of an angiogenic factor into the ischemic vertebral body could be performed to produce and/or induce angiogenesis within the vertebral body (and desirably the subchondral capillary bed that supplies the disc with its nutrients). The vertebral pedicle, a route used in pedicle screw spinal implants as well as vertebroplasty and kyphoplasty treatments of vertebral compression fractures, can easily be entered with a direct catheter for injection. The pedicle communicates with the vertebral body. The injection can be done percutaneously or with open surgery. This injection can be short term (one injection) or be delivered within an indwelling catheter for longer administration. In addition, a device could be introduced through the pedicle that can be placed within the vertebral body for long term introduction of factor(s). In addition to the vertebral pedicle, direct placement into the vertebral body through the vertebral body cortical wall could be a method of delivering angiogenic factors to the vertebrae. This can be performed at the time of open surgery or via a percutaneous route.

In one embodiment of the invention, the stimulation of perfusion in the area proximal to a pain generator can result in improving disc nutrition so as to enhance healing and production of appropriate proteins in said disc. It is known that the synthesis of proteoglycans in the nucleus pulposus occurs naturally by the cellular component of the nucleus pulposus. Specific growth factors such as transforming growth factor-β (TGF-β) and epidermal growth factor (EGF) are involved in the stimulation of proteoglycan synthesis. Interestingly, in patients with degenerative disc disease, the amount of these cytokines is reduced in comparison to healthy nucleus pulposus cells. This reduction may be due to decreased nutrient supply and cellular viability within said nucleus. Another reason for inhibition of proteoglycan synthesis is lower pH caused by ischemia and/or hypoperfusion of the lumbar area. The low pH also appears to be involved in another process associated with discogenic pain, said process comprising up regulation of matrix metalloproteases expression. It is known that matrix metalloproteases are involved in cleaving proteoglycans, and that up regulation of matrix metalloprotease activity is associated with disc degeneration. Activation of matrix metalloproteases is known to be induced by inflammatory cytokines such as TNF and IL-1. Additionally, animal studies have demonstrated that hyperphysiological loading of the disc segment induces up regulation of matrix metalloproteases, but have not assessed the influence of perfusion. Accordingly, in one embodiment of the invention, the increase of localized perfusion is used to augment proteoglycan content in said nucleus pulposus, as well as to lead to suppression, in some instances, of MMP activation.

One attraction of protein therapy is that relatively small amounts of a very potent therapeutic agent can be injected into the ischemic area of interest to pharmacologically initiate the process of blood vessel growth and collateral artery formation. In addition, from pharmacokinetic data collected from recent studies in the human heart, it appears that once FGF-1 exits a tissue structure it can be largely cleared from circulation in less than 3 hours. This diminishes the risk of FGF-1 stimulating unwanted angiogenesis in other tissues of the bodies where it could potentially promote inappropriate angiogenesis and other adverse physiologic responses.

In various alternative embodiments, genes can be introduced from exogenous sources so as to promote angiogenesis. It is known in the art that genes may be introduced by a wide range of approaches including adenoviral, adeno-associated, retroviral, alpha-viral, lentiviral, Kunjin virus, or HSV vectors, liposomal, nano-particle mediated as well as electroporation and Sleeping Beauty transposons. Genes with angiogenic stimulatory function that may be transfected include, but are not limited to: VEGFs, FGF-1, FGF-2, FGF-4, and HGF. Additionally, transcription factors that are associated with up regulating expression of angiogenic cascades may also be transfected into cells used for treatment of lower back pain. Said genes could include: HIF-1, HIF-2, NET (norepinephrine transporter gene), and NF-kB (nuclear factor-kappa B). Antisense oligonucleotides, ribozymes or short interfering RNA (ribonucleic acid) may be transfected into cells for use for treatment of lower back pain in order to block expression of antiangiogenic proteins such as IP-10 (Interferon-gamma-inducible 10 kDa protein).

Selection of genes or techniques for introduction of said genes in vivo may be performed in vitro prior to administration so as to allow for methods of screening and selecting the combination that is most angiogenically potent. Testing may be performed by various methodologies known to one skilled in the art. In terms of assessing angiogenic potential, said methodologies include, but are not limited to:

(A) Angiogenic activity may by assessed by the ability to stimulate endothelial cell proliferation in vitro using human umbilical vein endothelial cells (HUVECs) or other endothelial cell populations. Assessment of proliferation may be performed using tritiated thymidine incorporation or by visually counting said proliferating endothelial cells. A viability dye such as MTT or other commercially available indicators may be used.

(B) Angiogenic activity may also be assessed by the ability to support cord formation in subcutaneously implanted matrices. Said matrices, which may include Matrigel® or fibrin gel, are loaded with cells that do not have intrinsic angiogenic potential, for example fibroblasts, transfecting said cells with said genes, and implanting said cells subcutaneously in an animal. Said animal may be an immunodeficient mouse such as a SCID (severe combined immunodeficiency) or nude mouse in order to negate immunological differences. Subsequent to implantation, formation of endothelial cords generated from endogenous host cells may be assessed visually by microscopy. In order to distinguish cells stimulating angiogenesis versus host cells responding to said cells stimulating angiogenesis, a species-specific marker may be used.

(C) Angiogenic activity may be assessed by the ability to accelerate angiogenesis occurring in the embryonic chicken chorioallantoic membrane assay. Cells transfected with angiogenic genes may be implanted directly, or via a matrix, into the chicken chorioallantoic membrane on embryonic day 9 and cultured for a period of approximately 2 days. Visualization of angiogenesis may be performed using in vivo microscopy.

(D) Angiogenic activity may be assessed by the ability to stimulate neovascularization in the hind limb ischemia animal model. In one embodiment, patients diagnosed with hypoxic and/or ischemic disc disease could be treated using gene therapy in a localized manner.

In one embodiment, patients diagnosed with hypoxic and/or ischemic disc disease could be treated using gene therapy in a localized manner. Specifically, the gene for FGF-1 could be administered in a composition of nucleic acid sequences or one or more triplex DNA compounds, and a nonionic block copolymer. The gene administered could be under control of a strong promoter, for example, the CMV (cytomegalovirus) promoter. The nonionic block copolymer may be CRL-8131 as described in U.S. Pat. No. 6,933,286 (which is incorporated herein by reference in its entirety). Specifically, in such an embodiment 300 milligrams of CRL-8131 may be added to 10 ml of 0.9% NaCl and the mixture solubilized by storage at temperatures of 2-4° C. until a clear solution was formed. An appropriate amount of a FGF-1 expressing plasmid diluted in PBS (phosphate buffered saline) could be added to the mixture and micelles associating the copolymer and the compound could be formed by raising the temperature above 5° C. and allowing the suspension of micelles to equilibrate. The equilibrated suspension would be suitable for administration.

In other embodiments it may be desirable to utilize an angiogenesis-stimulating protein for administration in a therapeutically effective amount. Said protein may be selected from proteins known to stimulate angiogenesis, including but not limited to TPO (thyroid peroxidase), SCF (stem cell factor), IL-1 (interleukin 1), IL-3, IL-6, IL-7, IL-11, flt-3L (fms-like tyrosine kinase 3 ligand), G-CSF (granulocyte-colony stimulating factor), GM-CSF (granulocyte monocyte-colony stimulating factor), Epo (erythropoietin), FGF-1, FGF-2, FGF-4, FGF-5, FGF-20, IGF (insulin-like growth factor), EGF (epidermal growth factor), NGF (nerve growth factor), LIF (leukemia inhibitory factor), PDGF (platelet-derived growth factor), BMPs (bone morphogenetic protein), activin-A, VEGF (vascular endothelial growth factor), VEGF-B, VEGF-C, VEGF-D, PlGF, and HGF (hepatocyte growth factor). In some preferred embodiments, administration of the angiogenesis-stimulating protein is performed by injection directly into a vertebral body. In some embodiments, the angiogenic-stimulating protein is co-administered with stem or progenitor cells.

In some embodiments a carrier solution or containing/metering device may be desired. Appropriate carrier solutions may be selected based on properties such as viscosity, ease of administration, ability to bind solution over a period of time, and general affinity for the agent delivered. Said solutions may be modified or additives incorporated for modification of biological properties. Starting solutions may include certain delivery polymers known to one who is skilled in the art. These could be selected from, for example: polylactic acid (PLA), poly-L-lactic acid (PLLA), poly-D-lactic acid (PDLA), polyglycolide, polyglycolic acid (PGA), polylactide-co-glycolide (PLGA), polydioxanone, polygluconate, polylactic acid-polyethylene oxide copolymers, polyethylene oxide, modified cellulose, collagen, polyhydroxybutyrate, polyhydroxpriopionic acid, polyphosphoester, poly(alpha-hydroxy acid), polycaprolactone, polycarbonates, polyamides, polyanhydrides, polyamino acids, polyorthoesters, polyacetals, polycyanoacrylates, degradable urethanes, aliphatic polyester polyacrylates, polymethacrylate, acryl substituted cellulose acetates, non-degradable polyurethanes, polystyrenes, polyvinyl fluoride, polyvinyl imidazole, chlorosulphonated polyolefin, and polyvinyl alcohol.

Administration may be performed under fluoroscopy or by other means in order to allow for localization in proximity of the cause of hypoperfusion. Acceptable carriers, excipients, or stabilizers are also contemplated within the current invention; said carriers, excipients and stabilizers being relatively nontoxic to recipients at the dosages and concentrations employed, and may include buffers such as phosphate, citrate, and other organic acids; antioxidants including ascorbic acid, n-acetylcysteine, alpha tocopherol, and methionine; preservatives such as hexamethonium chloride; octadecyldimethylbenzyl ammonium chloride; benzalkonium chloride; phenol, benzyl alcohol, or butyl; alkyl parabens such as methyl or propyl paraben; catechol; resorcinol; cyclohexinol; 3-pentanol; and mecresol; low molecular weight polypeptides; proteins, such as gelatin, or non-specific immunoglobulins; amino acids such as glycine, glutamine, asparagine, histidine, arginine, or lysine; monosaccharides, disaccharides, and other carbohydrates including glucose, mannose, or dextrins; chelating agents such as EDTA (ethylenediaminetetraacetic acid); sugars such as sucrose, mannitol, trehalose, or sorbitol; salt-forming counter-ions such as sodium. For heparin-binding proteins, including FGFs, heparin may be incorporated into the formulation, which can bind and stabilize the protein against inactivation and degradation.

In various embodiments, treatment of hypoxic and/or ischemic disc disease could include the use of a biocompatible or biodegradable implant. Said biodegradable implants can contain a biodegradable delivery system, or carrier, as well as angiogenic factors; said angiogenic factors could be capable of stimulating sufficient neovascularization to overcome local hypoxia. One preferred angiogenic factor is fibroblast growth factor 1 (FGF-1). However, other recombinant naturally derived, in vitro derived, and in vivo derived angiogenic factors may also be used. In some embodiments, the biodegradable implant which contains said angiogenic factors contains a carrier. The carrier is preferably chosen so as to remain within the implanted site for a prolonged period and slowly release the angiogenic factors contained therein to the surrounding environment. This mode of delivery allows said angiogenic factors to remain in therapeutically effective amounts within the site for a prolonged period. By providing said angiogenic factors within a carrier, the advantage of releasing said angiogenic factors directly into the target area is realized. In some embodiments, the implant's carrier is provided in an injectable form. Injectability allows the carrier to be delivered in a minimally invasive and preferably percutaneous method. In some embodiments, the injectable carrier is a gel. In others, the injectable carrier comprises hyaluronic acid (HA).

In some embodiments, the carrier of the graft comprises a porous matrix having an average pore size of at least 25 micrometers. Preferably, the porous matrix has an average pore size of between 25 micrometers and 110 micrometers. When the average pore size is in this range, it is believed that the porous matrix will also act as a scaffold for in-migrating cells capable of becoming cells stimulatory of angiogenesis in the targeted area. Numerous examples of organic materials that can be used to form the porous matrix are known to one of skill in the art; these include, but are not limited to, collagen, polyamino acids, or gelatin.

Said collagen source may be artificial (i.e., recombinant), or autologous, or allogenic, or xenogeneic relative to the mammal receiving the implant. Said collagen may also be in the form of an atelopeptide or telopeptide collagen. Additionally, collagens from sources associated with high levels of angiogenesis, such as placentally derived collagen, may be used. Examples of synthetic polymers that can be used to form the matrix include, but are not limited to, polylactic acids, polyglycolic acids, or combinations of polylactic/polyglycolic acids. Resorbable polymers, as well as non-resorbable polymers, may constitute the matrix material. One of skill in the art will appreciate that the terms porous or semi-porous refer to the varying density of the pores in the matrix.

Scaffold structures may be used in some embodiments for anchoring or substantially causing adhesion between said implant and anatomical structures—such anatomical structures may include bone, cartilage, nerve, tendon, ligament, other anatomical structures and/or various combinations thereof. In some embodiments, the method of adhering said implant to said anatomical structures may be a gel. Said gel, together with said implant, can be injected to the graft site, in some embodiments under arthroscopic fluid conditions. The gel can be a biological or synthetic gel formed from a bioresorbable or bioabsorbable material that has the ability to resorb in a timely fashion in the body environment.

Suitable scaffold agents are also known to one of skill in the art and may include hyaluronic acid, collagen gel, alginate gel, gelatin-resorcin-formalin adhesive, mussel-based adhesive, dihydroxyphenylalanine-based adhesive, chitosan, transglutaminase, poly(amino acid)-based adhesive, cellulose-based adhesive, polysaccharide-based adhesive, synthetic acrylate-based adhesives, platelet rich plasma (PRP) gel, platelet poor plasma (PPP) gel, clot of PRP, clot of PPP, Matrigel®, Monostearoyl Glycerol co-Succinate. (MGSA), Monostearoyl Glycerol co-Succinate/polyethylene glycol (MGSA/PEG) copolymers, laminin, elastin, proteoglycans, poly(N-isopropylacrylamide), poly(oxyalkylene), a copolymer of poly(ethylene oxide)-poly(propylene oxide), polyvinyl alcohol and combinations thereof.

In some embodiments, a pliable scaffold could be preferred so as to allow the scaffold to adjust to the dimensions of the target site of implantation. For instance, the scaffold could comprise a gel-like material or an adhesive material, as well as a foam or mesh structure. Preferably, said scaffold can be a biodegradable, bioresorbable and/or bioabsorbable material. Said scaffold can be formed from a polymeric foam component having pores with an open cell pore structure. The pore size can vary, but in one preferred embodiment the pores could be sized to allow tissue or angiogenic ingrowth. In some embodiments, said pore size is in the range of about 40 to 900 micrometers. Said polymeric foam component can, optionally, contain a reinforcing component, such as, for example, woven, knitted, warped knitted (i.e., lace-like), non-woven, and braided structures. In some embodiments where the polymeric foam component contains a reinforcing component, the foam component can be integrated with the reinforcing component such that the pores of the foam component penetrate the mesh of the reinforcing component and interlock with the reinforcing component. In some embodiments, said angiogenic growth factors could be predominantly released from a sustained delivery device by its diffusion through the sustained delivery device (preferably, through a polymer). In others, said angiogenic factors could be predominantly released from the sustained delivery device by the biodegradation of the sustained delivery device (preferably, biodegradation of a polymer). In some embodiments, said implant comprises a bioresorbable material whose gradual erosion causes the gradual release of said angiogenic factors. In some embodiments, said implant comprises a bioresorbable polymer. Preferably, said bioresorbable polymer has a half-life of at least one month. Accordingly, in some embodiments, said implant comprises the co-polymer poly-DL-lactide-co-glycolide (PLG) admixed with said angiogenic factors.

In some embodiments, the implant could be comprised essentially of a hydrogel. Hydrogels can also be used to deliver said angiogenic factors in a time-release manner to the area of hypoperfusion. A "hydrogel", as defined herein, is a substance formed when an organic polymer (natural or synthetic) is set or solidified to create a three-dimensional open-lattice structure that entraps molecules of water or other solution to form a gel. Said solidification can occur, e.g., by aggregation, coagulation, hydrophobic interactions, or cross-linking. The hydrogels described herein could rapidly solidify to keep said angiogenic factors in proximity to either the blood vessel causative of hypoperfusion, or the area associated with hypoperfusion. In some embodiments, said hydrogel could be a fine, powdery synthetic hydrogel. Suitable hydrogels would desirably exhibit an optimal combination of such properties as compatibility with the matrix polymer of choice, and biocompatibility. The hydrogel can include one or more of the following: polysaccharides, proteins, polyphosphazenes, poly(oxyethylene)-poly(oxypropylene) block polymers, poly(oxyethylene)-poly(oxypropylene) block polymers of ethylene diamine, poly(acrylic acids), poly(methacrylic acids), copolymers of acrylic acid and methacrylic acid, polyvinyl acetate, and sulfonated polymers.

In one alternative embodiment, a localized medical device and/or composition could be implanted using an attachment mechanism onto an anatomical structure that resides at a location adjacent to and/or remote from the area of hypoperfusion, such as within and/or proximal to a blood vessel supplying the area of hypoperfusion (i.e., for example, the segmental vessels that feed to the subchondral capillary bed of a vertebral body). In various embodiments, attachment could be performed using an anchoring device; such as employing an anchoring device attaching a medical device to a vertebral bone proximal to one of the lumbar or medial sacral arteries. Said medical device could include an ability to provide time-course release of an angiogenic factor. Said medical device may include a solid casing with an internal gel-like fluid containing the desired angiogenic factor. Said gel-like fluid may be a cryoprecipitate, an administration matrix, or a composition of various polymers suitable for the sustained release of said angiogenesis promoting factor.

In one alternative embodiment, the medical device that adheres or attaches to the proximity of the hypoperfused area for the purpose of delivering the desired angiogenic factor could be placed near or in the proximity of the hypoperfused intervertebral disc endplate within the vertebral body. This medical device could be a reservoir for the formulation of the active delivered drug that is delivered over time to the endplate. This device could be made of synthetic or biologic material and be able to be attached with anchors or have positional stability without anchors.

Tissue Grafting and Spinal Fusion

In some instances, preparation for fusion or bone graft may desirably include angiogenesis and/or other treatments prior to, during and/or after the graft is implanted. Poor circulation is well known to be a chief factor for bone graft failure and lack of maturation. Treating the grafted area before (or during) the bone graft procedure could provide needed vascularity (and therefore, much needed oxygen for bone maturation). This treatment could be in the manner of injection of FGF-1 alone or in a vehicle such as xenograft, allograft, collagen matrix, synthetic, or other scaffolding.

Extended slow release dosing can allow continuous delivery of a small molecule or protein, thereby avoiding the concentration peaks and troughs of intermittent oral or bolus injectable doses. This can be achieved using a pump or either an injected or implanted polymeric gel. Injected biodegradable matrices would include, but are not limited to, those containing one or more of the following: heparin, collagen, gelatin, fibrin, and alginates.

FGF-1s can be used in which one or more amino acid insertions, deletions or substitutions are introduced by standard genetic engineering techniques, such as site-directed, deletion, and insertion mutagenesis. The wild type FGF-1 three-dimensional conformation is known to be marginally stable with denaturation occurring either at or near physiologic temperature. FGF-1 binding to heparin increases the thermal inactivation temperature by approximately 20 C. Therefore, FGF-1 is typically formulated with therapeutically approved USP heparin. However, heparin is an anticoagulant that can promote bleeding as a function of increasing concentration. In addition, some individuals have been immunologically sensitized to heparin by previous therapeutic exposure, which can lead to heparin-induced thrombocytopenia and thrombotic events. Mutations that extend the storage stability in vitro and biologic activity in vivo would allow FGF-1 to be formulated and dosed in the absence of exogenous heparin. These include mutations that decrease the rate of oxidative inactivation, such as replacement of one or more of the three cysteine residues by either serine or other compatible residues. In particular, as has been described by others, substitution of cysteine 117 by serine is known to substantially increase the half-life of human FGF-1 by decreasing the rate of oxidative inaction. Other mutations have been described that increase conformational stability by making amino acid changes in internal buried and/or external exposed amino acid residues. In the case of repeat dosing regimens, FGF-1s exhibiting greater stability and life-time might effectively decrease the frequency and number of repeated doses needed to achieve sustained exposure and greater efficacy. These stabilized mutants would allow longer duration dosing from slow release polymeric matrices and delivery systems.

Various bone grafting surgeries in which angiogenesis may be desirable could be either in the anterior or posterior, interbody (whether posterior interbody, anterior interbody, lateral approaches to the interspace and with or without interbody implants) or posterolateral spinal fusions in either the cervical, thoracic or lumbar region. In addition, various alternative embodiments contemplated herein include the use of angiogenic factors and/or other biological treatments (i.e., stem cell therapy, etc.), either alone or in various combinations, for treatment of other anatomical tissues, including actetabular and femoral grafting, pseudoarthrosis treatment of any bone and, most specifically, the tibia due to its well-known poor vascularity, femoral head avascular necrosis, avascular necrosis of the navicular bone of the foot, mandibular necrosis, wrist scaphoid avascular necrosis, lunate avascular necrosis, humeral head avascular necrosis, talar avascular necrosis, and or any other bony pathology that requires or desires bone grafting, including those bones that could have actual or potential vascular compromise.

In various embodiments, angiogenic treatments can be used in conjunction with other treatments, such as introduction and/or injection of stem cells, which may be embryonic stem cells or adult stem cells. Such angiogenic treatments could be used to prepare tissues for subsequent injection of stem cells, or angiogenic compounds could be injected concurrently with and/or after introduction of such cells. With regards to intervertebral disc tissues or other tissues, growth factors, synthetic or treated allograft or xenograft tissue for scaffold (or extra-cellular matrix) and stem cells (each of which could be used separately or in varying levels of in combination with each other) could be utilized to "engineer" or otherwise modify disc tissue with the goal of regenerating living tissue within the intervertebral disc. If the degenerative disc to be treated required that ischemia or hypoxia related causes needed to be diagnosed and treated first or in combination with the tissue engineering techniques (or if such treatment could be optimized if such approaches were employed), then the diagnosis and treatment could be for ischemic disc disease or other pathologies such as described herein.

In addition, it may be determined that a combination of stem cells, engineered tissue, scaffold, growth factors, or combinations thereof, would be enhanced by combining angiogenic factors such as FGF-1 in its native state or through an FGF-1 mutant (through protein engineering technology) or any other appropriate angiogenic factor. In this embodiment, the regenerative implant would desirably be selected and/or designed to not over-utilize the nutrients available for the intradiscal chondrocytes. A limiting factor of disc regenerative therapy may be nutrient, nutritional and/or waste disposal constraints on any therapy that seeks to increase the intradiscal cellular population and metabolic rate. In combination therapy, nutrient delivery to the chondrocytes may be desirably enhanced through increasing the population of endplate capillaries.

Combination therapy could also include tissue engineered disc material that is transplanted into a disc space made available by removing some or all previous degenerative disc material. To provide nutrients for this transplant, angiogenic therapy with or without cartilaginous endplate reconstruction, if needed, could be included. In addition, this combination therapy could be further enhanced with growth factors or other signaling molecules and embryonic or adult stem cells and various types of scaffold. The preoperative planning would desirably map the areas to be treated. Preoperative imaging, as described before, could analyze the metabolic demands of the combination transplant and the state of the nutrient pathway that is required to support the transplant. Detailed preoperative planning, using imaging modalities already discussed (or imaging modalities not yet invented or used for this type of procedure) of the nutrient demands of the transplant and the subsequent translation of this imaging data into the proper amount, delivery, vehicle, approach, number of discs, which side of the disc, which anterior-posterior orientation, whether the cartilaginous endplate is required to be perforated, thinned or otherwise reconstructed, what other discs require treatment and how that information impacts the treatment plan and other yet unknown factors could all be information utilized when planning the regenerative disc therapy.

A similar approach could be used in connection with other joint structures and/or other tissues and organs, including structures such as the heart. One main dysfunction associated with ischemic heart disease appears to be a loss of perfusion of oxygenated blood to the heart tissue. If stem cell, gene therapy, protein therapy, tissue therapy or any combination thereof were implanted within heart tissue and/or otherwise directed towards the tissue of the heart, the metabolic demands of that transplant could be calculated with preoperative imaging and the proper angiogenic treatment delivered based upon that calculation. Alternatively, if the imaging demonstrated a range of breakdown of the delivery pathway to the transplanted tissue, cells, proteins, genes or any combination thereof, then a more non-specific dose of angiogenic therapy might be desired. The angiogenic treatment could be initiated, based on imaging data, prior to the regenerative treatment so that angiogenesis would already be present when the transplant is performed. In addition, the angiogenic treatment could be combined with the tissue/cell/signal transplant (or other regenerative embodiment), providing capillary growth and nutrient delivery to enhance healing of the transplant at the time of the procedure or subsequently after surgery. Administration of such factors could be accomplished prior to, during and/or after such surgery to the patient and/or the tissue transplant, as desired.

In a similar fashion, chronic wounds or ulcers, such as diabetic foot ulcers, or other wounds known to be of ischemic origin, could be treated in a combination approach. If cells, signaling proteins such as various growth factors, genes or any other tissue or synthetic transplantation were contemplated to be utilized in an area of ulcer on the diabetic foot or other area of anatomy that is suffering with a chronic ischemic wound, then proper pre-treatment ischemic analysis using various imaging modalities discussed herein might be utilized. If areas of ischemia were identified that required pre-treatment with angiogenic factors (prior to the previously mentioned transplantation or coverage procedure), then the proper dosage and administration of said angiogenic factors could be provided as a combination treatment.

In a similar manner, the various treatments described herein can be used to prepare other tissues that are treated with tissue transplants and also have a high metabolic demand in the face of poor nutrient delivery. One example could be in the treatment of soft tissue loss in open fractures such as the tibia. It is well known that tibial non-unions have a poor blood supply and a tissue transfer, transplant, cell therapy, growth factor or other signaling molecules included in the tissue grafting could create a greater metabolic demand (both nutritionally and waste-related), thus requiring greater nutrient delivery and/or waste removal. Combination therapy, including various aspects of the previously-discussed tissue grafting procedures with angiogenic treatment could be ascertained with the proper imaging studies and the type of angiogenic therapy, dose, distribution, delivery, and vehicle thoughtfully planned. This type of treatment would be useful in other similar ischemic tissue challenges, or other areas that have tissue defects in need of restoration throughout the body. This could include facial injuries or tumor or other musculoskeletal tissue defects.

In one exemplary embodiment, the various diagnosis and treatments described herein could have particular utility in combination with spinal fusion procedures. Because fusion procedures typically involve cutting and disrupting spinal anatomical structures, and often involve the use of spinal instrumentation anchored into one or more vertebral bodies using pedicle screws or other hardware, the performance of such procedures is likely to disrupt normal spinal blood flow patterns. In the case of pedicle screw placement into a vertebral body, the surgical drilling procedure and placement of the screw body itself may disrupt, reduce and/or halt the intervertebral flow for a significant period of time or even permanently, which may be further exacerbated by the common practice of placing screws into each of the two pedicles of an individual vertebrae as well as the injection of PMMA bone cement into the vertebrae that may occur as an adjunct to screw fixation. Where intervertebral blood flow has been reduced and/or halted, there is likely to be a commensurate reduction in the diffusion of nutrition to the intervertebral discs adjacent to that treated vertebrae. This has the potential of being a major factor in the occurrence of "adjacent level disease," which refers to the increased degenerative changes seen in the intervertebral discs and vertebrae at the spinal levels adjacent to fused levels. While it is commonly believed that such degeneration may be due to increased biomechanical forces experienced at the adjacent levels, or simply due to further progression of the degenerative disc disease, it is likely that the significant reduction of nutrition from the treated vertebral level, in combination with the increased loading of the adjacent disc and possibly a reduction in nutrition from the endplate of the untreated adjacent vertebrae (which could be due to undiagnosed ischemia in the adjacent vertebrae as well) is a primary cause of "adjacent level disease."

Where fusion of one or more spinal levels is contemplated or has already been performed, it may be desirous to image and/or analyze the immediately adjacent spinal levels (above and/or below the treated levels) to determine if vertebral body (especially endplate) and/or disc ischemia is present or likely to occur. Where imaging indicates such ischemia is present or likely in an adjacent level, it may be desirous to treat the adjacent level as described herein, either proactively (before surgery to improve the adjacent blood flow and disc nutrition) or retroactively (after the fusion surgery to potentially improve blood flow and/or nutrition in the adjacent vertebral body and adjacent disc.) Even where such ischemia has not been identified in the adjacent level, it may be desirous to treat the adjacent vertebral level as described herein to improve existing blood flow and disc nutrition, as surgical disruption of anatomical structures at a surgically treated level can negatively impact blood flow and disc nutritional diffusion coming from that surgical level. The knowledge that the adjacent discs have a very high probability to develop adjacent segment disease due to ischemic disc disease could prompt the clinician to prophylactically treat that disc at the time of the index procedure at the adjacent level. This could include delivery of angiogenic factors in the manner already discussed and/or "unloading" the treated disc with the proper implant. In addition, if the adjacent discs are left untreated, in regards to ischemic disc disease, it may be decided that serial imaging, in the method described previously, would be desirable in the postoperative period following the lumbar fusion. During this time, if the discs proximal or distal to the fusion began to demonstrate ischemic evidence of impending ischemic disc disease, early ischemic disc disease or true ischemic disc disease with resultant degenerative disc disease, treatment in the manner already described could commence at that point.

In various additional embodiments, the angiogenic treatments described herein could be used in conjunction with tissue grafts of the spine, including fusion grafts, "gutter" grafts, interspinous grafts, tissue implants and/or grafts between vertebral bodies and/or graft materials positioned within an evacuated and/or partially evacuated interverterbal disc space.

Dynamic Stabilization, InterSpinous Spacers and Other Spinal Instrumentation

In various embodiment, the diagnosis and treatments described herein can have particularly utility in combination with spinal instrumentation and/or procedures that "offload," distract, limit the mobility of, isolate and/or otherwise provide temporary and/or permanent reduction in the localized loading of one or more spinal segments. A wide variety of such systems and/or procedures are in common practice, including dynamic stabilization and interspinous spacers system.

Dynamic stabilization and interspinous spacer systems and surgical procedures, which are used to address a number of clinical indications, typically include instrumentation systems anchored or otherwise secured to one or more vertebrae. These systems desirably seek to stabilize one or more vertebral levels, and typically allow some level of motion between adjacent spinal segments. Dynamic stabilization often includes flexible and/or moveable rods or springs, which are secured to pedicle screws or other instrumentation anchored between adjacent vertebrae. Interspinous spacers typically are spring-like or solid structures placed between the interspinous processes of adjacent vertebrae, with the device attached to at least one of the vertebrae. Of course, there are a significant number of variations and hybrid constructs that utilize various securement locations and attachments structures, all of which are contemplated herein, including the use of lateral and/or anterior constructs.

A common feature of these "dynamic" systems is that they are designed to typically allow some relative motion between the vertebrae to which they are secured, which is unlike fusion instrumentation, which typically seeks to immobilize vertebrae relative to one another. In many cases, the dynamic systems seek to "off load" or otherwise reduce stresses experienced by the intervertebral disc and/or facet joints, which may render such systems particularly useful with various embodiments described herein.

As previously described, it is believed that vertebral vascular insufficiencies adjacent to an intervertebral endplate are a significant contributor to the degradation and eventual failure of the relevant intervertebral disc. It is further believed that, when a degenerating disc experiences continued and/or increased loading levels (especially where the disc may be adjacent to a fused or otherwise mechanically constrained adjacent vertebral level), this continued loading further degrades the disc structure. It is believed that the subsequent angiogenic treatment of the vertebral vascular insufficiency after such diagnosis could be facilitated by the implantation of one or more dynamic systems across the involved vertebral level, such that the intervertebral disc adjacent the treated location was "offloaded" to some degree for a limited period of time. This offloading, in conjunction with the increase in diffusive nutrition/waste removal resulting from the angiogenic treatment, has a significant opportunity to reduce, halt and/or reverse the effects of the earlier degradation. FIG. 17 depicts a spinal stabilization system 400, such as a dynamic motion/rod system and/or interspinous spacer system, placed between the L4 and L5 vertebrae of an exemplary spinal motion segment and used concurrently with treatment using angiogenic factors 410.

The combination of angiogenic therapy with spinal instrumentation desirably pharmacologically improves the nutrient exchange and waste removal of the disc while unloading the disc mechanically. This optimizes the clinical approach, because the diminishing population of endplate capillaries can be a consequence of increased matrix "strain," and lessening the spot strain on vulnerable disc tissue can optimize the environment. The combined efforts to improve local blood flow in this situation can be important, as the endplate can also be subject to "spot loading". By at least partially unloading the disc to improve the extracellular matrix "strain" and improving blood flow by administration of FGF-1 or similar angiogenic compounds into and/or around the cartilaginous endplate, this approach can restore the endplate as a nutrient exchange tissue. In various embodiments where pedicle screw instrumentation is to be used, an exemplary treatment could include the injection of an angiogenic material into each of the prepared pedicle screw holes or channels formed into the pedicle/vertebral body, which may include the controlled localization of such material proximate one or more endplates, and then the subsequent placement of the pedicle screw body into the channel for anchoring of the instrumentation.

Ischemic Tissue Treatment and Spinal Instrumentation and Treatment

The various techniques of treating ischemic discs and vertebral bodies may achieve particular utility when combined with various spinal treatment and instrumentation procedures currently available and/or developed in the future. At present, various total disc replacement implants are utilized clinically to relieve pain due to disc disease while continuing motion at that segment. Many "total disc replacements" are utilized at one lumbar disc level when another disc or disc may be "at risk" for developing accelerated disc disease. Deciding a rational treatment approach is difficult for these discs due to lack of knowledge of the mechanism of the accelerated disc disease and the method of imaging that mechanism. As in the situation of lumbar fusion, adjacent disc disease could be evaluated by single or serial endplate imaging and associated studies (either preoperatively or postoperatively) and treated with angiogenic therapy (or combined therapies that include angiogenic therapy as one factor) described herein.

Surgical Tools, Procedures and Techniques

Once a targeted anatomical region and intended interventional treatment regimen have been determined, a surgical access path and procedure will typically be determined. In many cases, the simple injection of drugs, proteins, cells and/or compounds into the vasculature and/or soft tissues can be accomplished using hypodermic needles, catheters and/or other minimally- or less-invasive surgical devices. However, where such injections desirably target specific tissues, where such devices may be utilized proximate to sensitive and/or fragile tissues structures, where such devices must transition through and/or into dense or bony tissues, or where a more invasive surgical intervention is desired, additional surgical techniques and/or tools may be required.

Where injection of an angiogenic factor or other compound into a vertebral body is desirous, there can be a variety of acceptable surgical access paths which to choose. Access to a vertebral body (or any other targeted anatomical regions) can be accomplished from many different directions, depending upon the targeted location within the vertebral body, the intervening anatomy, and the desired complexity of the procedure. For example, access can be obtained through one or more pedicles (transpedicular), outside of a pedicle (extrapedicular), along either side of the vertebral body (posterolateral), superiorly or inferiorly (such as through an upper or lower intervertebral disc and/or adjacent vertebral bodies), laterally and/or anteriorly. In addition, such approaches can be used with a closed, minimally invasive procedure and/or with a percutaneous procedure and/or with an open procedure (or some combination thereof).

For some areas of the lumbar spine, access to a hypoperfused or ischemic area to be treated may be complicated by surrounding anatomy. At the T12 to L1 level, the diaphragm, liver and/or T12 rib may interfere with a desired approach. If the surgeon contemplates treatment of the T12-L1 or L1-L2 disc and/or associated vertebral bodies, various approach paths may be preferred to avoid such structures. In a similar manner, the L4-5 and L5-1 discs and related spinal levels are often associated with vascular and neural anatomy that is unique to those levels, and care to avoid certain vascular and/or neural anatomy, especially using anterior and/or lateral approaches, might be required. In addition, the transpedicular approach at virtually every spinal level can be associated with the adjacent spinal canal with its dural sac or spinal cord, as well as various exiting nerve roots. A surgeon will prefer to avoid the spinal canal and nerve root foramen to ensure that such structures are not penetrated and/or damaged during a selected treatment approach to the vertebral bodies and/or disc.

In addition, a transvertebral or transdiscal approach, possibly from the posterior-lateral corner may be associated with an exiting or traversing nerve root. A direct lateral approach can be associated with the psoas major muscle with its associated lumbosacral plexus. It may be preferred to avoid these structures in these approaches. Moreover, a transpedicular, posterior, posterolateral or lateral approach can be associated with vascular (or nervous) structures on the other side of the vertebrae, and it would be desirable to keep instruments within the confines of the vertebrae, disc and/or disc endplate and avoid unintentional damage to such structures.

Vertebral bodies can be easily accessed from a posterior approach, although the spinal cord and various nerves and vasculature will desirably be avoided during such an approach. Lateral approaches to the vertebral body can be accomplished, though the ribs, iliac crest and/or other anatomical features may limit such access for various vertebral levels. Vertebral bodies can also be accessed from an anterior approach, though the presence of the abdominal aorta and/or iliac arteries and the need for a vascular access surgeon (to access the anterior spinal anatomy) limit the convenience of this type of access approach. However, this access might be effective if it is performed for an adjacent segment at the time of an arthroplasty or anterior fusion. As already described "adjacent segment" discs can occasionally be "at risk" for accelerated degeneration following anterior lumbar fusion and even lumbar disc arthroplasty. This condition might be prevented with an angiogenic treatment to the vertebral endplate. In this situation, the endplate could be reached by either direct access to the vertebral body by starting a "starter hole" by drilling the anterior cortex and then a needle with the angiogenic factors in solution or in other formulations could be directed toward the endplates and injected at the desired anatomic region under fluoroscopic control. Alternatively, a needle could be directed through the anterior disc into the endplates (instead of through the anterior vertebral body) and injection of the drug into the cartilaginous endplate and or bony endplate under fluoroscopic control. A combination of bony access plus discal access could also be desired.

In many cases, minimally-invasive access into a vertebral body can best be accomplished using a transpedicular access path through the pedicles of the vertebral body. This approach can be readily identified and targeted by trained surgeons using physical palpitation of the patient's anatomy, the access needles can travel easily through the cancellous bone within the pedicle, and the anatomy lends itself to anterior/posterior and lateral fluoroscopic imaging and guidance of the needle.

In many cases, minimally-invasive devices such as hypodermic needles and cannulae can be introduced via a needlestick or small incision in the patient's skin and soft tissues, and guided to a desired location within the anatomy using fluoroscopic or other non-invasive types of visualization. For example, if minimally-invasive access through a pedicle into a vertebral body is desired, an A/P (anterior/posterior) view of the vertebral body may be taking using a fluoroscopic visualization system such as a C-arm, commercially available from GE Medical Systems. The pedicle can be visualized on the scan as an oval-shaped body, and the needle tip can be inserted through the patient's skin and soft tissues and advanced until it contacts and slightly penetrates the posterior pedicle surface. The C-arm can then be repositioned to show a lateral view of the vertebrae, and additional fluoroscopic imaging can be used to visualize the advancement and positioning of the needle through the pedicle and into the vertebral body. It is possible that intraoperative CT, MRI or ultrasound (or other imaging modalities not yet in clinical use) may be used by the surgeon to ascertain, to a greater degree of clarity, the exact position of the device and/or verify the location of delivery of the active drug and/or carrier. If the carrier is not radiopaque, then a sufficient amount of a radiopaque material, such as barium powder, may be mixed with the carrier, angiogenic material and/or other injectable compound to allow fluoroscopic visualization and localization of the compound.

In various embodiments described herein, it may be desirous to inject compositions and/or materials, including angiogenic compounds, into specific and/or discrete locations within a patient's anatomy. For example, where imaging, analysis and diagnosis indicates a hypoperfused subchondral capillary bed within a vertebral body proximate to an endplate of an intervertebral disc, it may be desirous to inject an angiogenic factor into the vertebral body in an attempt to produce angiogenesis within the vertebral body. Depending upon the clinical needs, the injection may simply be into the vertebral body, or it may desirably be proximate to a specific area within the vertebral body, such as proximate to the hypoperfused subchondral capillary bed at the vertebral endplate. However, because the pedicle is an essentially cylindrical or tubular structure with a generally well-defined trajectory, a straight needle will generally follow this straight path and there may be limited opportunity to maneuver and/or redirect the needle through the pedicle into a desired location within the vertebral body. This difficulty can be further exacerbated where an injection is desired in one side of a vertebral body not easily directly access through the opposing pedicle of the body (i.e., accessing the left side of the vertebral body using a needle through the right pedicle of the body).

FIGS. 11A and 11B depict embodiments of a flexible and/or steerable spinal access device or needle 400 for accessing a vertebral body 405 through a pedicle 410 and accessing discrete locations within the vertebral body. The needle 400 can be a standard spinal or Jamshidi-type needle, or it can include particularized features for accomplishing specific goals within an intended environment of use. In various embodiments, the needle 400 or needle subassembly can include steerable or deformable features, which desirably allow the needle or needle subassembly to be direct towards and/or away from specific anatomy. In the disclosed embodiment, the needle 400 can include a deformable shaft, tube or lumen 415 which can be formed from a spring-loaded and/or deformable material such as spring steel and/or Nitinol (or other shape memory metal). Desirably, the tube 415 can travel down an inner lumen (not shown) of the spinal needle 400, which desirably prevents significant deformation of the tube (i.e., it follows the needle lumen), but when the tube 415 exits the lumen, the natural tendency of the tube to curve, bend or otherwise deform will allow the tube 415 to follow a curved or other shaped path within the vertebral body. Typically, because the intravertebral space is filled with relatively dense cancellous bone, the tube 415 will carve a curved path through the bone. FIG. 11A depicts an exemplary position of the needle 400 and tube 415 to access a central anterior wall of the vertebral body. FIG. 11B depicts an exemplary position of the needle 400 and tube 415 to access an inferior portion of the vertebral body 405 proximate an endplate 420.

Once the tube 415 is in a desired position, in various embodiments it many include an internal tube lumen (not shown) with an exit opening 425, and the lumen may be employed for a variety of uses. For example, the lumen may be used to withdraw material from the vertebral body, such as to sample biopsies or to sample fluid for a variety of uses, including to test for levels of metabolic wastes. The lumen may also be used to introduce material into the vertebral body, such as introducing contrast agents to improve visualization and/or to introduce therapeutic agents into the vertebral body.

In one exemplary embodiment, the tube 415 could be used to inject a contrast agent to assist with imaging of the intravertebral structures, and the same tube can be used to administer a therapeutic agent, including an angiogenic factor, into the vertebral body (which can be accomplished in any order, depending upon physician preference). Such an approach could facilitate the visualization and treatment of a target area, or a similar process may be used to verify that the therapeutic agent will remain within the targeted treatment site, and not extravasate an undesired amount into the surrounding vasculature (i.e., monitor the contrast flow, and assume the therapeutic agent is likely to follow the prior contrast flow path).

In various embodiments, the tube 415 and/or needle may be repositioned and/or moved to alter the location of the exit opening 425 in the targeted anatomical location. The location of the needle and/or tube may be monitored by the surgeon using fluoroscopic imaging and/or visual cues on tube attachments located outside of the patient's anatomy (i.e., a visible marking on the tube handle to indicate the orientation of the tip and/or the depth beyond the needle opening. If desired, the spinal needle 410 could be withdrawn almost entirely from the vertebral body and then the tube allowed to move forward and carve a curved path, which could facilitate the positioning of the exit opening 425 proximate the upper endplate 435.

If desired, the tube 415 could comprise a solid bendable structure having a relatively sharpened or rounded tip, which could be used to create one or more channels (not shown) within the cancellous bone of the vertebral body 405. In this embodiment, the tube 415 could then be removed from the spinal needle 400, and the spinal needle (or another instrument travelling through the spinal needle) could be employed to introduce a material including an angiogenic factor. Such a system could be employed to create a desired flowpath for the angiogenic factor, which may not be concurrent with the natural microvasculature of the intravertebral circulatory system. Desirably, the angiogenic factor under pressure could flow into the various channels formed in the vertebral body.

There are a variety of such commercially available for accessing and injecting bone cement or other materials into vertebral bodies pursuant to vertebroplasty and kyphoplasty procedures, including systems commercially available from Medtronic, Inc. of Minneapolis, Minn. or other manufacturers. Such systems can be utilized to access desired locations within a targeted vertebral body and/or within the intervertebral disc, if desired. Once placed in a desired position within the vertebral body, which can be verified using fluoroscopic visualization and/or visual indicators on the tool that extend outside of the patient's body, an angiogenic material and/or other compound can be injected through the hollow body of the needle and into the vertebral body in a desired manner.

In various alternative embodiments, the introduction of angiogenic materials into a targeted location within a bony structure such as a vertebra may include the desire to create a cavity or opening within the structure of the bone, which can then be filled, injected with and/or otherwise accommodate the introduced compound or implant. Because cancellous or trabecular bone can be quite dense, it may be desirous to create an opening and/or repository within the bony structure into which the material can be introduced. In some cases, for example, the injected material may include a non-flowable constituent, which has difficulty being (or cannot be) introduced against resistance. Injection into a defined cavity can have the additional advantage of ensuring placement of the material in a desired location, as opposed to potential extravasation and/or flow of the compound into the vasculature and/or elsewhere if directly introduced into unprepared bone. A wide variety of commercially-available instruments are available that can mechanically and/or pneumatically create voids and/or openings within vertebral bodies, including expandable mechanical cutting devices and inflatable bone tamps, all of which are commercially available from Medtronic or some other appropriate manufacturer. In various embodiments, once one or more cavities or other voids has been formed in the bone, such as in a location proximate to a disc endplate, an angiogenic factor can be introduced into the cavity, and desirably induce angiogenesis to ultimately improve diffusive nutrition/waste flow to/from the intervertebral disc.

FIGS. 12, 13 and 14 depict alternative exemplary embodiments of surgical access and injection tools for introduction of angiogenic materials into targeted locations within a bony structure such as a vertebra and/or within a soft tissue or connective structure such as an intervertebral disc and/or within a vascular structure such as a vein, artery or capillary. In FIG. 12, the surgical tool 500 could comprise a spinal access needle 510, the needle 510 having a handle 515, a substantially tubular rigid body 520 having a lumen (not shown) extending therethrough, and a flexible stylet 525. The tubular body 520 could have a sharped distal end 530 and a proximal fitting such as a luer lock fitting 535.

In use, the sharpened distal end 530 and tubular body 520 of the needle could be inserted into a desired target anatomy, which could include accessing a patient's vertebral body via a pedicle access (see FIGS. 24A and 24B), via an extrapedicular access (see FIGS. 22A and 22B), via a lateral access (see FIGS. 24A, 24B, 21A and 21B), or other access approaches as desired.

As best seen in FIGS. 21A through 24B, the spinal access needle 510 further includes a flexible stylet 525, which can be formed from a spring-loaded and/or deformable material such as spring steel and/or Nitinol (or other shape memory metal). Desirably, the stylet 525 can travel down an inner lumen (not shown) of the spinal access needle 5100, which desirably prevents significant deformation of the stylet (i.e., it follows the needle lumen), but when the stylet 525 exits the lumen, the natural tendency of the stylet to curve, bend or otherwise deform will allow the stylet 525 to follow a curved or other shaped path within the vertebral body. In the disclosed embodiment, the stylet is sufficiently flexible and pre-flexed to form a ring-shaped feature in the vertebral body, depending on the amount that the stylet 525 is extended from the needle tip. Of course, other designs for the stylet could be employed, including stylets of differing shapes and/or sizes, as well as hollow stylets, as desired.

Once one or more desired channels have been formed in the vertebral body by advancement and refraction of the stylet, the stylet can be removed (if desired) and a therapeutic substance or material (including materials that incorporate an angiogenic factor therein) can be introduced into the needle and vertebral body. In various embodiments, the material or therapeutic substance can be introduced under pressure so as to force some material into the channels formed therein. In various alternative embodiments, the material may be introduced before channel formation using the stylet, and then the stylet can be used to form channels within the bone with the material already resident therein.

In various alternative embodiment, the stylet may be used to create one or more channels in the intravertebral space proximate to an endplate, with the trauma created by the introduction of the stylet potentially creating an angiogenic response by the body. In some cases, typically depending upon the level of ischemia detected, this approach might have a potential to induce revascularization of the intravertebral subchondral capillary bed to some meaningful degree. Such an approach may require no introduction of an angiogenic factor, or may require only a limited amount of such angiogenic factor to be introduced as compared to treatments with little or no trauma induced to the bone.

During a typical bilateral procedure to access a targeted vertebral body, a patient lies on an operating table. The patient can lie face down on the table, or on either side, or at an oblique angle, depending upon the physician's preference. The physician initially introduces a spinal needle assembly into soft tissue in the patient's back. Under radiologic or CT monitoring, the physician advances the spinal needle assembly through soft tissue down to and into the targeted pedicle and/or vertebral body (i.e., if a lateral vertebral body access is chosen).

The physician will typically administer a local anesthetic, fir example, lidocaine, through the spinal needle assembly, or some other forms of anesthesia. The physician directs the spinal needle assembly to penetrate the cortical bone and/or cancellous bone of the pedicle or, if a lateral access is selected, through the side of the vertebral body. Preferably the depth of penetration is about 30% to 70% of the vertebral body. The physician holds the stylus and withdraws the stylet of the spinal needle assembly and access to the vertebral body is achieved.

In addition, there may be situations where an intradiscal approach to the hypoperfused endplate may be preferable, and such approaches are contemplated in the various embodiments described herein. The depth and direction of the delivery tool/needle could be monitored by the appropriate imaging modality and the proper position of the instrument be located. Injection of the desired dose at the appropriate location could then be accomplished.

If it is desirable to create a cavity or otherwise modify the interior of the vertebral body for some reason, the physician may choose to slide a guide pin instrument through the stylus and into the cortical/cancellous bone. The physician could then remove the stylus, leaving the guide pin instrument deployed within the bone.

The physician can next slide obturator instrument over the guide pin instrument, distal end first. The physician can couple the obturator instrument to a handle, which facilitates manipulation of the instrument. The physician can make a small incision in the patient's back, and then twist the handle while applying longitudinal force to the handle. In response, the obturator instrument could desirably rotate and/or penetrate soft tissue through the incision. The physician may also gently tap the handle, or otherwise apply appropriate additional longitudinal force to the handle, to advance the obturator instrument through the soft tissue along the guide pin instrument down to the cortical bone entry site. The physician can also tap the handle with an appropriate striking tool to advance the obturator instrument into the pedicle and/or a side of the vertebral body to secure its position.

The obturator instrument can include a larger outside diameter that is generally well suited for establishing a lateral access, or the obturator can have a narrower diameter if access is desired through a narrower region of the vertebral body, e.g., a pedicle (generally called a transpedicular access). In such a case, the outside diameter of the obturator instrument can be reduced to well below the diameter of the pedicle. The reduced diameter of the obturator instrument in this manner can mediate against damage or breakage of the pedicle. It should be understood that the disclosed devices are well suited for use in conjunction with other approach paths, such as pedicular, extra-pedicular, posterolateral, superior, inferior and/or anterior approaches and various intradiscal approaches (i.e., into the disc and/or through the disc and into the vertebral body and/or through the vertebral body into the disc), with varying results. The physician may then slide the handle off the obturator instrument and slide a cannula instrument over the guide pin instrument and, further, over the obturator instrument. If desired, the physician can also couple a handle to the cannula instrument, to apply appropriate twisting and longitudinal forces to rotate and advance the cannula instrument through soft tissue over the obturator instrument. When the cannula instrument contacts cortical bone, the physician can appropriately tap the handle with a striking tool to advance the end surface of the cannula into the vertebral body to secure its position.

The physician now withdraws the obturator instrument, leaving the cannula instrument in place. The physician can then slide a drill bit or instrument (i.e., cutting tool, probe, biopsy tool for taking samples, etc.) through the cannula instrument, until contact between the machined or cutting edge of the drill bit instrument and cancellous or cortical bone occurs. The physician may couple the instrument to a handle. Guided by X-ray visualization (or other non-invasive and/or partially invasive visualizing system), the physician can apply appropriate twisting and/or longitudinal forces to the handle, to rotate and advance the machined or sharp edges of the instrument to open a passage within the vertebral body.

Once vertebral body access is achieved, and/or after any cavities and/or voids have been created in the vertebral body (which, depending upon the physician's preference, may include no void creation whatsoever), the physician can introduce a therapeutic material into the targeted vertebral body (or other anatomical location). The material can desirably comprise an angiogenic material, which may form a mixture with a variety of other materials or compounds, which could include allograft tissue, autograft tissue, hydroxyapatite or other natural or synthetic bone substitute, a semi-solid slurry material (e.g., a bone slurry in a saline base), containment devices, stem cells, anti-inflammatory compounds, carriers, other compounds or devices described and/or disclosed herein and/or other medications.

After injection of the relevant material(s) have been achieved, the surgical instruments can be removed, the wound closed and/or sutured, and the patient allowed to rest and recuperate. In various embodiments, and depending upon the nature of the treatment, the disclosed procedures could possibly be performed on an out-patient basis and/or under local anesthetic. Of course, the use of general anesthetics and in-patient treatment procedures and protocols are contemplated herein as well, depending upon the patient's physical condition and age, the surgical complexity and the overall disruption to the patient's anatomy.

EXAMPLES

The following examples are for illustrative purposes only and are not intended, nor should they be interpreted, to limit the scope of the invention.

Ex. 1—Intervertebral Disc Treatment

In one exemplary embodiment, a patient with lower back pain or other anatomical issues, who has not improved with conservative care, can undergo endplate perfusion imaging as described herein that, when analyzed, demonstrates one or more lumbar discs and/or vertebral bodies that have significant loss of endplate perfusion in either the superior or inferior endplate or both. The disc (or discs) may show evidence of loss of normal hydration, or water content on routine MRI scanning and the location of the disc correlates with the patient's persistent, chronic pain. Further imaging studies could be obtained to ascertain the degree of loss of normal proteogylcan, increase in lactate and/or hydrogen with corresponding lowering of pH and a change in the diffusion characteristics of the disc using the ADC value and progressive loss of endplate integrity using such methods as ultrashort time to echo MRI could be compared to earlier images or scans of the patient and/or other more normal discs. The endplate perfusion could be analyzed in detail and identify specifics as to the anterior, posterior, cephalad, caudad, medial/lateral and/or left/right location of the perfusion deficits. One or more endplate perfusion 2D or 3D maps (which could include structural and/or colorized flow maps) could be generated for further detail. Maps prepared using different imaging modalities (i.e., MRA and MRI, for example) or identifying different anatomical characteristics (i.e., images reflecting perfusion flow overlain by images reflecting cancellous bone structure and/or metabolic waste imaging) could be compared and/or overlain, and the resulting data tabulated and/or analyzed. The surgeon could begin planning the proper placement of the angiogenic factor by injecting it alone or in associated delivery vehicles. The angiogenic factor could be FGF-1 or FGF-1 mutant or other angiogenic factors. The angiogenic factor may be formulated in a variety of vehicles and/or carriers defined for specific surgical needs.

As an example, the inferior endplate may require an angiogenic factor in an intravertebrally placed vehicle or alternatively in a vehicle that requires an anchor or some other attachment device that would allow a broad and stable surface area for delivery of the drug. Various other modifications may be required depending upon the superior or inferior endplate, superior or inferior location or left or right sided location. In addition, the level of the disc involved may require specific angiogenic formulations, vehicles, matrixes, synthetics, carriers, mutants, attachments, anchors, dosages, repeat doses, delivery devices, bone penetrating instruments, instrumented linkages, robotic delivery, image guided delivery and/or targeted delivery selections. In addition, if a portion of the cartilaginous endplate was sacrificed as part of the normal approach to gain access to the drug delivery zone and a reconstruction was required or desired, a cartilaginous endplate transplant could be performed at the same time as the angiogenic treatment or in a staged procedure. In addition, if endplate imaging showed that a preoperative defect would require reconstruction prior to the angiogenic treatment, then the endplate reconstruction could be done first and the angiogenesis performed at the same time or in a second stage.

If other regenerative intervertebral disc therapy is planned, either tissue based, cell based, gene based or protein based, or some other biologic or synthetic regenerative or tissue engineering treatment, and it was ascertained that the above diagnostic and angiogenic treatment and/or endplate reconstruction was desired prior to or during the regenerative treatment, then the above diagnostic and treatment protocol could be performed in concert with the regenerative treatment or in a staged fashion.

To monitor the amount of stress that the intervertebral disc and cartilaginous endplate withstands and thus guide postoperative endplate load bearing, micro force transducers or other devices could be positioned in strategic areas to measure the amount, location and distribution of the stress at the cartilaginous and bony endplates. These force transducers could be linked with other implantable monitoring devices that could include accelerometers, GPS and strain gauges and/or other micro mechanical and biologically compatible instruments. These may be manufactured with either synthetic or biologic material, or combinations thereof.

As previously noted, the amount of stress, loading and/or movement the disc might be subjected to could be modified by the surgical placement of supplementary spinal instrumentation, such as fusion devices (i.e., permanent and/or temporary devices), non-fusion devices and/or synthetic or biologically engineered stabilizing devices that could share load with the healing disc. In various embodiments, such devices could be modifiable in the amount of "load sharing" and/or movement they allow, if desired. In a manner similar to a crutch used by a patient after orthopaedic surgery, the patient may undergo progressively increased amounts of weight bearing following the disc repair and/or reconstructive procedure, including the application of progressive, monitored, measurable, controllable stress that could provide the correct signal for optimal vessel growth, chondrocyte productivity and matrix repair.

Ex. 2—Lumbar Segmental Artery Analysis Combined with Vertebral Body Dynamic Perfusion In various embodiments, the vertebral arterial tree and vertebral body blood flow can be simultaneously and/or sequentially evaluated for the purpose of vascular mapping of the lumbar spine. The goal of such a study can be (1) to develop a safe and reproducible technique of MRA and perfusion utilizing one injection of contrast, (2) to measure vertebral perfusion and compare intra-subject and inter-subject results with the degree of segmental artery stenosis and degenerative disc disease, (3) to begin evaluating normal controls. and/or (4) to diagnose and/or treat the patient.

In one exemplary embodiment, both the lumbar MRA and dynamic perfusion portions were contrast enhanced. Subjects were volunteers with degenerative disc disease (DDD) and low back pain and were referred from spine surgeon practices or by word of mouth. The images were acquired with a Philips Achieva 3T system. For all imaging protocols, we used 330 mm*300 mm FOV and a 6-element SENSE torso RF coil. The imaging session started with the perfusion scan following the standard calibration scans. A 3D FFE sequence with TR/TE=3.5 ms/1.5 ms, SENSE factor: 2.5 (AP), 2(RL), flip angle=30°, with dynamic scan time of 2.9 seconds was used and 7 slices in sagittal orientation with 6 mm thickness and 1.9 mm*1.9 mm pixel size were acquired. A total of 114 volumes were collected, 2 of them before contrast injection. After the dynamic scans, T1 weighted anatomical images in sagittal plane were collected using a TSE sequence with 0.5*0.5*3 mm$^3$ voxel size. Fourteen slices covered the same volume as dynamic scans. TR/TE=900 ms/10 ms, flip angle=90°. This was followed by a T2 weighted scan that had identical geometry to T1 scans and TR/TE=2940 ms/120 ms, flip angle=90°. Finally, contrast enhanced angiography scans were collected. Contrast bolus arrival was observed real-time using a single, 50 mm thick coronal slice using FFE sequence in dynamic mode, collecting images every 0.5 s. Once the contrast arrived in descending aorta, actual 3D angiography scan was started by the operator immediately. TR/TE=5.1 ms/1.78 ms, voxel size=0.8*0.8*1.5 mm$^3$, with SENSE factor=4 was used to acquire 50 coronal slices.

Segmental vessels on MRA were graded as occluded, stenotic or open. Discs were graded as per Pfirrmann. Region of interest (ROI)-averaged time course (from whole vertebra and/or end-plate) was converted into a fractional enhancement time course and analyzed using a compartmental model (Larsson, et. al. MRM 35:716-726, 1996; Workie, et. al. MRI, 1201-1210, 2004). The model fitting resulted in 6 parameters: $K^{trans\prime}$ (apparent volume transfer constant), $k_{ep}$ (rate constant), Vp' (apparent fractional plasma volume), E (extraction fraction), tlag (arrival time of tracer in the ROI) and baseline.

FIG. 1 shows Coronal MRA for a healthy control subject compared to 3 subjects with symptoms of chronic lower back pain and DDD (Sub1, Sub2, Sub3). The control was a 20-year old with normal discs and segmental vessels from L1 to L5. The arrows indicate areas of stenosis or occlusion. Sub1 showed areas of stenosis indicated by the arrows. Sub2 showed areas of occlusion indicated by the blunt arrow. Sub3 showed areas of both occlusion (left blunt arrow) and stenosis (right arrow).

Each of the three symptomatic subjects demonstrated at least one segmental vessel that was either occluded or stenotic. Subjects 1 and 3 demonstrated decreased $K_{trans}$ at the level of the vascular lesion(s) with subject 3 demonstrating an order of magnitude lower value at all vertebral levels indicating a perfusion abnormality beyond the MRA identified lesions (FIG. 1). The other perfusion parameters ($k_{ep}$, Vp and E) can be extracted from the acquired data and are helpful in the interpretation. Pixel by pixel images can be generated of any parameter (and through any slice) for visual comparison.

FIG. 2 shows the data for subject 3 of FIG. 1, in which panel A shows an abnormal MRA scan, panel B shows Grade 1 DDD, panel C shows pixilation of perfusion data and panel D shows a color bar for comparison. The red coloring at the top of the bar is maximum $K^{trans}$. Consistent with FIG. 1, the arrow in Abnormal MRA Scan (panel A of FIG. 2) shows a stenotic left L4 segmental vessel. The blunt arrow in Abnormal MRA Scan (panel A of FIG. 2) shows an occluded right L4 segmental vessel. Panels C & D of FIG. 2 show perfusion ($K_{trans}$). As shown by the color of panel C and the side arrow in panel D, sub3 has low blood flow through the vertebrae compared to the control subject shown in FIG. 3 where normal (higher) blood flow through the vertebrae is shown by the color of panel C and position of the side arrow in panel D.

FIG. 3 shows data for the control of FIG. 1, in which panel A shows a normal MRA scan, panel B shows normal discs, panel C shows pixilation of perfusion data and panel D shows a color bar for comparison. The red coloring at the top of the bar is maximum K'.

Color coded scans and/or color maps can conveniently and accurately demonstrate the disease visually and is more adaptable for clinical use (although non-color and other data sets and maps can be used, if desired). Using this technique, data can be entered into a pooled multicenter database. Subsets of patients that may have a significant vascular and resultant ischemic/hypoxic component to their disease can then be identified.

TABLE 1

$K_{trans}$ values of L3-S1 vertebral bodies for 3 subjects

| Vertebrae | Control | Sub 1 | Sub 2 | Sub 3 |
|---|---|---|---|---|
| L3 | .215 | .146 | .160 | .090 |
| L4 | .220 | .148 | .156 | .084 |

TABLE 1-continued $K_{trans}$ values of L3-S1 vertebral bodies for 3 subjects

| Vertebrae | Control | Sub 1 | Sub 2 | Sub 3 |
|---|---|---|---|---|
| L5 | .205 | .170 | .160 | .075 |
| S1 | .149 | .160 | .146 | .053 |

Table 1 shows $K_{trans}$ values at sacral (S1) and Lumbar (L3, L4, and L5) positions for the healthy control and three symptomatic subjects (sub1-3). Decreased $K_{trans}$ values are observed in all symptomatic subject vertebral levels. $K_{trans}$ for sub3 is approximately 2-3 fold lower at each vertebra compared to sub1 and sub2.

FIG. 4 shows a Max Intensity projection (MIP) (Panel A) and Axial reconstruction (Panel B) for sub3. The blunt arrow in panel A of FIG. 4 and the blunt arrow in panel B of FIG. 4 point to an occluded vessel. The left hand arrow in panel B of FIG. 4 points to a stenosis.

A method for studying the vascular anatomy and dynamics of the spine in one scanning session using a contrast agent is demonstrated. Spinal anatomy, vascular anatomy and sophisticated perfusion data can be obtained. $K_{trans}$ is the rate of transfer of contrast delivered to the interstitial tissue, while the $k_{ep}$ is the rate the delivered contrast is cleared from the interstitial tissue, or "wash out". In addition, E (the extraction fraction of contrast during its initial passage within a given volume [ROI]) is another helpful parameter. If decreased blood supply is an etiologic factor in a subset of patients with DDD, this technique provides a mechanism by which investigators can study this disease in vivo.

Newer MR techniques such as MR Spectroscopy can be added to identify metabolic abnormalities within the disc. For example, lactate, an end product of anaerobic metabolism, may be increased in the disc that obtains its nutrients from vertebral bodies with poor perfusion. FIG. 5 demonstrates 2 discs that have undergone spectroscopy. Panel A of FIG. 5 shows the L4-5 disc outlined, and panel B of FIG. 5 shows the L5-1 disc (Disc B, panel B). When water is suppressed (panel B of FIG. 6), Disc B has a higher lipid+lactate peak [(Lip+Lac)/water=0.405] compared to Disc A [(Lip+Lac)/water=0.019] (panel A of FIG. 6), indicating a higher lactate concentration. This higher lactate may be associated with anaerobic metabolism and discogenic pain. In FIG. 6, "Lip"=lipid and "Lac"=lactate.

Ex. 3—DCE-MRI and Subchondral Perfusion

In another exemplary embodiment, DCE-MRI could be performed as the last scan in a given imaging session. One exemplary protocol based on a 3D gradient-echo sequence could employ the following parameters: TR=3.4 ms, TE=1.2 ms, Flip-angle=30°, NEX=1, and 36.4 sec. temporal resolution.

Any number of dynamic frames could be taken. For example, 22 dynamic frames may be prescribed, with a contrast agent administered manually as a bolus w/a saline flush via an antecubital vein at the onset of the $3^{rd}$ dynamic frame. The overall injection time of both the contrast and saline can be less than 10 seconds. Various contrast agents may be used, including 0.1 mmol/kg of Gadopentetic acid or Magnevist commercially available from Bayer Schering Pharma of Berlin-Wedding, Germany. If desired, an identical single-frame image could be acquired 20 or more minutes later to observe any delayed gadolinium enhancement in the discs.

The generation of a contrast-induced signal enhancement map (SE-map) of the relevant data and a subsequent analyses can be performed. If desired, the contrast-induced signal enhancement in DCEMRI can be normalized into percentage enhancement by first subtracting the baseline (which can be the mean of 2 pre-contrast dynamic frames) from all subsequent post-contrast time frames (i.e., from the $3^{rd}$ to the last dynamic frames) and then dividing the differences by the baseline. This operation can be carried out either in a pixel-by-pixel basis for creation of an enhancement map or in a region-of-interest (ROI)-averaged sense for enhancement time-course. FIGS. 20A and 20B demonstrate midsagittal sections through lumbar spines with normal discs (FIG. 20A) and abnormal discs (FIG. 20B). The T2 scan can be used to indicate the area analyzed by the pixel-by-pixel created color enhancement map of the vertebral body perfusion. The graph shows time course data from ROI's. Rectangles at the endplates represent ROI's drawn and/or derived (i.e., by a computer modeling program). In this example, the normal discs (FIG. 20A) can have greater amount of pixels than the abnormal discs (FIG. 20B). In addition, the time to peak, peak enhancement and washout are similar between endplates. The abnormal discs show heterogeneity.

Various aspects of the data can be examined, either alone or in various combinations, including spatial maps of signal enhancement at one or more fixed time points and an ROI-averaged temporal characteristic in the time course data. Spatial mapping can yield results and/or quantities reflecting an effective capillary perfusion in the endplates. FIG. 16 demonstrates a color map of a mid-sagittal section of the DCE-MRI of a lumbar spine. The scale displays red as highest perfusion. The lumbar discs 350 show no perfusion and the vertebral endplates, especially the superior endplates 360, show increased perfusion as compared to the vertebral body and inferior endplates.

Other parameters derived from the temporal characteristic can provide complementary information regarding changes in the capillary structure. For the temporal analysis, the volume-averaged signal enhancement time course can be generated. The enhancement time course can be initially analyzed in a semi-quantitative manner, assessing the parameters such as the maximum enhancement value (%), the time-to-peak (sec), and the clearance rate (%/sec), which in this example could be defined as the slope of the straight line between the $4^{th}$ and the last ($22^{nd}$) frame. Other quantitative analyses based on a compartmental model, shape-based fitting and/or nonlinear pharmacokinetic models could be utilized.

Other Joints, Organs and Tissues

The various embodiments described herein, including the analysis of image data, diagnosis of ischemic disease and treatments thereof using various tools, techniques and surgical methods can be applied to any joint in a human or animal body, including, without limitation, a spine, an elbow, a shoulder, a wrist, a hand, a finger, a jaw, a hip, a knee, an ankle, a foot, or a toe joint. In a similar manner, various alternative embodiments and/or modifications thereof could be used for the imaging, analysis, diagnosis and/or treatment of soft tissue structures and/or other organs, including the heart, heart tissue grafts and/or heart transplants.

In various alternative exemplary embodiments, methods of diagnosing a condition responsible for a degenerative joint condition that could include one or more of the following steps:

a) assessing a patient by one or more of the following steps:
 (i) obtaining image data of one or more joint structures of the patient;
 (ii) identifying one or more regions of interest within the image data;
 (iii) analyzing the one or more regions of interest to identify one or more areas of intraosseous hypoperfusion proximate to one or more areas of osteochondral tissues of the joint; and
 (iv) diagnosing the patient with said intraosseous hypoperfusion proximate to said osteochondral tissue of the joint.

In various alternative exemplary embodiments, methods of diagnosing a condition responsible for a degenerative tissue condition that could include one or more of the following steps:

a) assessing a patient by one or more of the following steps:
 (i) obtaining image data of one or more tissue structures of the patient;
 (ii) identifying one or more regions of interest within the image data;
 (iii) analyzing the one or more regions of interest to identify one or more areas of hypoperfusion within the tissue structures; and
 (iv) diagnosing the patient with said hypoperfusion within the tissue structures of the patient.

Of course, once a candidate is identified using one or more of these methods, a suitable treatment regime can be performed on the patient, such as the various treatments described herein.

HEADINGS

The headings provided herein are merely for the reader's convenience, and should not be construed as limiting the scope of the various disclosures or sections thereunder, nor should they preclude the application of such disclosures to various other embodiments or sections described herein.

INCORPORATION BY REFERENCE

The entire disclosure of each of the publications, patent documents, and other references referred to herein is incorporated herein by reference in its entirety for all purposes to the same extent as if each individual source were individually denoted as being incorporated by reference.

EQUIVALENTS

Although the invention has been described and illustrated with a certain degree of particularity, it is understood that the disclosure has been made only by way of example, and that numerous changes in the conditions and order of steps can be resorted to by those skilled in the art without departing from the spirit and scope of the invention. The invention may be embodied in other specific forms without departing from the spirit or essential characteristics thereof. The foregoing embodiments are therefore to be considered in all respects illustrative rather than limiting on the invention described herein. Scope of the invention is thus intended to include all changes that come within the meaning and range of equivalency of the claims provided herein.

What is claimed is:

1. A method of diagnosing and treating a recipient site of a patient at least a day prior to the recipient site receiving a surgically implanted tissue graft, comprising the steps of:
 imaging a patient to generate image data;
 obtaining image data of the patient, the image data including at least a portion of a disc of the patient proximal to the recipient site and metabolic abnormalities within the disc;
 quantifying localized perfusion of at least the portion of the disc of the patient and metabolic abnormalities within the disc to identify at least one hypoperfused region and the metabolic abnormalities within the disc by diffusion weighted imaging and Apparent Diffusion Coefficient;
 introducing a first amount of a compound comprising FGF-1 into the at least one hypoperfused region; and
 introducing a first therapeutically effective amount of at least one member of the group consisting of embryonic stem cells, adult stem cells, stem cells and progenitor cells into the at least one hypoperfused region, wherein the introduction of the compound comprising FGF-1and the introduction of the at least one of the embryonic stem cells, adult stem cells, stem cells and progenitor cells induce growth of at least one member of the group consisting of capillaries, arterioles, venules, microvasculature and blood vessels within at least a portion of the at least one hypoperfused region before the tissue graft is introduced to the recipient site.

2. The method of claim 1, wherein the step of introducing the compound comprising FGF-1 into the at least one hypoperfused region comprises injecting the compound comprising FGF-1 into the at least one hypoperfused region.

3. The method of claim 2, wherein the step of injecting the compound comprising FGF-1 into the at least one hypoperfused region is performed via a percutaneous route.

4. The method of claim 1, wherein the step of introducing the therapeutically effective amount of at least one member of the group consisting of embryonic stem cells, adult stem cells, stem cells and progenitor cells into the at least one hypoperfused region comprises injecting the therapeutically effective amount of at least one member of the group consisting of embryonic stem cells, adult stem cells, stem cells and progenitor cells into the at least one hypoperfused region.

5. The method of claim 4, wherein the step of injecting the therapeutically effective amount of at least one member of the group consisting of embryonic stem cells, adult stem cells, stem cells and progenitor cells into the at least one hypoperfused region is performed via a percutaneous route.

6. The method of claim 1, wherein the step of introducing the compound comprising FGF-I into the at least one hypoperfused region precedes the step of introducing the therapeutically effective amount of at least one member of the group consisting of embryonic stem cells, adult stem cells, stem cells and progenitor cells into the at least one hypoperfused region.

7. The method of claim 1, wherein the step of introducing the compound comprising FGF-1 into the at least one hypoperfused region occurs during a first surgical procedure and the step of introducing the therapeutically effective amount of at least one member of the group consisting of embryonic stem cells, adult stem cells, stem cells and progenitor cells into the at least one hypoperfused region occurs during a second surgical procedure.

8. The method of claim 1, wherein the recipient site comprises at least a portion of an organ of the patient.

9. The method of claim 1, wherein the recipient site comprises a nonhealing ischemic wound of the patient.

10. The method of claim 9, wherein the recipient site comprises a diabetic foot ulcer of the patient.

11. The method of claim 1, wherein the recipient site comprises a nonhealing open fracture in a bone of the patient.

12. The method of claim 11, wherein the recipient site comprises a nonhealing open tibial fracture of the patient.

13. The method of claim 1, further comprising the steps of:
- surgically implanting the tissue graft proximate to the recipient site, and
- introducing a second amount of the compound comprising FGF-1 and a second therapeutically effective amount of at least one member of the group consisting of embryonic stem cells, adult stem cells, stem cells and progenitor cells into the at least one hypoperfused region after the tissue graft has been surgically implanted.

14. The method of claim 1, further comprising the steps of
- surgically implanting the tissue graft proximate to the recipient site, and
- introducing a second amount of the compound comprising FGF-1 and a second therapeutically effective amount of at least one member of the group consisting of embryonic stem cells, adult stem cells, stem cells and progenitor cells into the at least one hypoperfused region concurrently with the tissue graft being surgically implanted.

15. The method of claim 1, further comprising the step of imaging the at least one hypoperfused region and analyzing the image data to determine if induced growth of blood vessels and angiogenesis has occurred within the at least one hypoperfused region prior to surgically implanting the tissue graft proximate to the recipient site.

* * * * *